United States Patent
Whittaker et al.

(10) Patent No.: US 9,527,853 B2
(45) Date of Patent: Dec. 27, 2016

(54) FUSED TRIAZOLE DERIVATIVES AS GAMMA SECRETASE MODULATORS

(71) Applicant: Ares Trading S.A., Aubonne (CH)

(72) Inventors: Ben Whittaker, Bedfordshire (GB); Chris Steele, Essex (GB); David Hardick, Stretham (GB); Dale Mitchell, Essex (GB); Vincent Pomel, Groisy (FR); Anna Quattropani, Rolle (CH); Dirk Beher, Gland (CH)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 14/406,386

(22) PCT Filed: Jun. 14, 2013

(86) PCT No.: PCT/EP2013/001774
§ 371 (c)(1),
(2) Date: Dec. 8, 2014

(87) PCT Pub. No.: WO2014/012614
PCT Pub. Date: Jan. 23, 2014

(65) Prior Publication Data
US 2015/0183790 A1 Jul. 2, 2015

Related U.S. Application Data

(60) Provisional application No. 61/672,436, filed on Jul. 17, 2012.

(30) Foreign Application Priority Data

Jul. 17, 2012 (EP) ..................... 12176726

(51) Int. Cl.
| | |
|---|---|
| C07D 401/00 | (2006.01) |
| C07D 419/00 | (2006.01) |
| C07D 487/00 | (2006.01) |
| C07D 249/16 | (2006.01) |
| C07D 403/00 | (2006.01) |
| A61K 31/535 | (2006.01) |
| A61K 31/41 | (2006.01) |
| A61K 31/415 | (2006.01) |
| C07D 487/04 | (2006.01) |
| C07D 471/04 | (2006.01) |
| C07D 498/04 | (2006.01) |
| A61K 31/4192 | (2006.01) |
| A61K 31/437 | (2006.01) |
| A61K 31/4439 | (2006.01) |
| A61K 31/444 | (2006.01) |
| A61K 31/5383 | (2006.01) |
| A61K 45/06 | (2006.01) |

(52) U.S. Cl.
CPC ......... *C07D 487/04* (2013.01); *A61K 31/4192* (2013.01); *A61K 31/437* (2013.01); *A61K 31/444* (2013.01); *A61K 31/4439* (2013.01); *A61K 31/5383* (2013.01); *A61K 45/06* (2013.01); *C07D 471/04* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 2002/0128319 A1 | 9/2002 | Koo | |
| 2012/0059030 A1* | 3/2012 | Koike | C07D 471/04 514/303 |

FOREIGN PATENT DOCUMENTS

| | | |
|---|---|---|
| EP | 1992618 A1 | 11/2008 |
| EP | 2455380 A1 | 5/2012 |
| WO | 2004110350 A2 | 12/2004 |
| WO | 2009032277 A1 | 3/2009 |
| WO | 2009073777 A1 | 6/2009 |
| WO | 2010083141 A1 | 7/2010 |
| WO | 2010098487 A1 | 9/2010 |
| WO | 2010098495 A1 | 9/2010 |
| WO | 2011086098 A1 | 7/2011 |

OTHER PUBLICATIONS

Chowdhury, C. et al. Expedient and Rapid Synthesis of 1,2,3-Triazolo[5,1-c]morpholines through Palladium-Copper Catalysis. J. Org. Chem. 2009, vol. 74, p. 3613.*
Dunn, PJ. et al. Green Chemistry Principle #8. ACS What is Green Chemistry. Accessed from ACS Website on Jan. 8, 2016.*
Abarca, "Triazolopyridines 20. Hydrogenation Reactions#", Tetrahedron, 1999, 55: 12881-12884.
Beher, "γ-Secretase Modulation and its Promise for Alzheimer's Disease: a Rationale for Drug Discovery", Curr Topics Med Chem, 2008, 8: 34-37.
Chowhudry, "Expedient and Rapid Synthesis of 1,2,3-Triazolo[5,1-c]morpholines through Palladium-Copper Catalysis", J. Org. Chem, 2009, 74(9): 3612-3615.

(Continued)

Primary Examiner — Rita Desai
Assistant Examiner — Ben S Michelson
(74) Attorney, Agent, or Firm — Dwight D. Kim; EMD Serono Research and Development Institute

(57) ABSTRACT

The present invention provides fused bicyclic triazole derivatives of Formula (I) useful as gamma secretase modulators (GSM), for the treatment of Alzheimer's disease and related diseases.

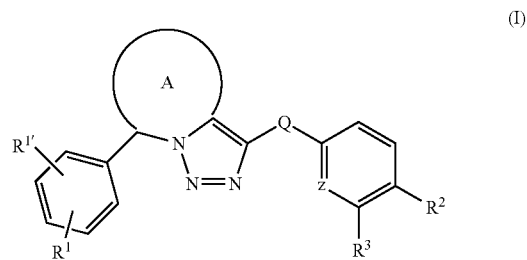

12 Claims, No Drawings

(56) References Cited

OTHER PUBLICATIONS

Chuprakov, "Rh-Catalyzed Transannulation of Pyridotriazoles with Alkynes and Nitriles", Chem. Int. Ed. 2007, 46(25): 4757-4759.
De Strooper, "Aph-1, Pen-2, and Nicastrin with Presenilin Generate an Active y-Secretase Complex", Neuron, 2003, 38: 9-12.
Eriksen, "NSAIDs and enantiomers of flurbiprofen target γ-secretase and lower Aβ42 in vivo", J. Clin. Invest., (2003), 112(3): 440-449.
Green, "Effect of Tarenflurbil on Cognitive Decline and Activities of DailyLiving in Patients With Mild Alzheimer Disease: A Randomized Controlled Trial", JAMA, 2009, 302(23): 2557-2564.
Greene and Wuts, "Protective Groups in Organic Synthesis", Wiley Interscience, 3rd Edition, 1999.
Haapasalo, "The Many Substrates of Presenilin/γ-Secretase", J Alzheimers Dis., 2011, 25(1): 3-28.
Hardy, "Has the Amyloid Cascade Hypothesis for Alzheimer's Disease been Proved?" Current Alzheimer Research, 2006, 3: 71-73.
Higuchi and Stella, "Pro-drugs as Novel Delivery Systems", vol. 14 of the A.C.S. Symposium Series, American Chemical Society, (1975).
Kocienski Philip J., "Protecting Groups", Georg Thieme Verlag Stuttgart, New York, 1994.
Larner, "Secretases as therapeutics targets in Alzheimer's disease: patents 2000-2004", Expert Opin. Ther. Patents, 2004,14(10): 1403-1420.
Lübbers, "Aminothiazoles as y-secretase modulators", Bioorg. Med. Chem. Lett., 2011, 21: 6554-6558.
Marjaux, "γ-Secretase inhibitors: still in the running as Alzheimer's therapeutics", Drug Discovery Today: Therapeutic Strategies, 2004, 1(1): 1-6.
Peretto, "Synthesis and Biological Activity of Flurbiprofen Analogues as Selective Inhibitors of β-Amyloid1-42 Secretion", J. Med. Chem., 2005, 48: 5705-5720.
Pettersson, "Design and synthesis of dihydrobenzofuran amides as orally bioavailable, centrally active y-secretase modulators", Bioorg. Med. Chem. Lett, 2012, 22: 2906-2911.
Roche, "Bioreversible Carriers in Drug Design: Theory and Application", Pergamon Press (New York), 1987, pp. 14-21.
Schor, "What the Halted Phase III y-Secretase Inhibitor Trial May (or May Not) Be Telling Us", Ann Neurol, 2011, 69: 237-239.
Steiner, "Uncovering y-Secretase", Current Alzheimer Research, 2004, 1: 175-181.
Tanzi, "Twenty Years of the Alzheimer's Disease Amyloid Hypothesis: A Genetic Perspective", Cell, 2005, 120: 545-555.
Tyle, "Iontophoretic Devices for Drug Delivery", Pharmaceutical Research, 1986, 3(6): 318-319.
Wilcock, "Efficacy and safety of tarenflurbil in mild to moderate Alzheimer's disease: a randomised phase II trial", Lancet Neurol, 2008, 7: 483-493.
Wong, "Chronic Treatment with the y-Secretase Inhibitor LY-411,575 Inhibits β-Amyloid Peptide Production and Alters Lymphopoiesis, and Intestinal Cell Differentiation", J. Biol. Chem., 2004, 279: 12876-12882.
Yoshida, "Study of biodegradable copoly (L-lactic acid/glycolic acid) formulations with controlled release of Z-100 for application in radiation therapy", Int. J. Pharm., 1995, 115: 61-67.
Extended EP Search Report dated Sep. 26, 2012.

* cited by examiner

FUSED TRIAZOLE DERIVATIVES AS GAMMA SECRETASE MODULATORS

RELATED APPLICATIONS

The present application is a U.S. national stage application of PCT International Application PCT/EP2013/001774, filed on Jun. 14, 2013, which claims the benefit of U.S. Provisional Application U.S. Ser. No. 61/672,436, filed on Jul. 17, 2012, and European application EP 12176726.3, filed on Jul. 17, 2012. The entire contents of the aforementioned applications are incorporated herein by reference.

The present invention provides fused bicyclic triazole derivatives useful as gamma secretase modulators (GSM). The invention further relates to processes for preparing such compounds, pharmaceutical compositions comprising said compounds and their use in the treatment of amyloidosis and neurodegenerative diseases that include, but are not limited to, Alzheimer's disease and Down's Syndrome.

BACKGROUND OF THE INVENTION

Alzheimer's disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. At present, there are no effective treatments for AD and treatment is limited to the use of symptomatic agents such as the cholinesterase inhibitor, donepezil (Aricept®, Pfizer). The total net cost related to AD in the U.S. exceeds $100 billion annually.

AD is characterised pathologically by the presence of specific lesions in the limbic and cortical regions of the brain. These include intracellular neurofibrillary tangles consisting of hyperphosphorylated tau protein and the extracellular deposition of fibrillar aggregates of amyloid-beta peptides in the form of amyloid plaques (senile plaques). The major components of amyloid plaques are amyloid-beta (A-beta, Abeta or Aβ) peptides of various lengths (39-42 amino acids). A variant thereof, which is the Aβ1-42 (Abeta1-42, Aβ42) peptide, is believed to be the major pathogenic species in AD brain and can act as a seed for amyloid plaque formation. Another variant is the Aβ1-40 (Abeta1-40, Aβ40) peptide.

The identification of mutations in the beta-Amyloid Precursor Protein (beta-APP, β-APP or APP), Presenilin-1 (PS-1) and Presenilin-2 (PS-2) genes that increase Aβ production and lead to early-onset familial forms of AD have given strong support to the "amyloid cascade hypothesis" of AD (Hardy, 2006 Curr Alzheimer Res. 3(1):71-73; Tanzi and Bertram, 2005 Cell 120, 545) and therapeutic approaches targeting Aβ production. There is emerging data on the role of Aβ peptides in other diseases including, but not limited to Down's syndrome (DS), mild cognitive impairment (MCI), cerebral amyloid angiopathy (CAA), inclusion body myositis (IBM) and age-related macular degeneration. Hence, Aβ lowering agents could be beneficial for the treatment of diverse pathologies in which Aβ peptides are implicated.

Aβ peptides are generated following proteolytic processing of APP. The generation of Aβ peptides is regulated by at least two proteolytic activities referred to as β-site APP cleaving enzyme 1 (BACE-1) and γ-secretase. APP is initially cleaved by BACE-1 at the N-terminus (Met-Asp bond) of the Aβ domain leading to the secretion of soluble APPβ (sAPPβ) and the retention of a 12 kDa membrane-bound carboxy terminal fragment (CTFβ). The latter is subsequently cleaved by γ-secretase to generate Aβ peptides of varying length and an APP intracellular domain (AICD).

It has now become clear that the γ-secretase activity cannot be ascribed to a single protein, but is in fact associated with an assembly of different proteins. The γ-secretase activity resides within a multiprotein complex containing at least four components: a presenilin (PS) heterodimer, nicastrin, anterior pharynx-defective 1 (Aph-1) and presenilin enhancer 2 (Pen-2). The PS heterodimer consists of the amino- and carboxy terminal fragments generated by endoproteolysis of PS and the two aspartates in the catalytic site are at the interface of this heterodimer. It has recently been suggested that nicastrin serves as a γ-secretase-substrate receptor. The functions of the other members of γ-secretase are unknown, but they are all required for activity (De Strooper, 2003 Neuron 38: 9-12; Steiner, 2004. Curr Alzheimer Research 1(3): 175-181). In addition to cleaving APP, γ-secretase is implicated in the intramembrane proteolysis of a number of other proteins including Notch (Haapasalo & Kovacs, 2011 J. Alz. Dis. 25: 3-28).

Due to its pivotal role in the generation of Aβ peptides, γ-secretase is a prime target for the treatment of AD. Various strategies have been proposed for targeting γ-secretase ranging from targeting the catalytic site directly (γ-secretase inhibitors), developing substrate-specific inhibitors (selective γ-secretase inhibitors) and developing modulators of γ-secretase activity (GSMs) (Beher, 2008 Curr Top Med Chem. 8: 34-37, Marjaux et al, 2004. Drug Discovery Today: Therapeutic Strategies, Volume 1, 1-6). Accordingly, a variety of compounds were described that have secretases as targets (Lamer, 2004. Secretases as therapeutics targets in AD: patents 2000-2004. Expert Opin. Ther. Patents 14, 1403-1420). However, due to the fundamental role γ-secretase plays in the intramembrane proteolysis of other proteins, the development of γ-secretase inhibitors was hindered by mechanism-based toxicities associated with inhibition of Notch signalling (Wong et al, 2004 J. Biol. Chem. 279: 12876-12882; Schor, 2011 Ann Neurol. 69: 237-239).

The development of GSMs that have no effect on Notch processing and therefore, should be safer and better tolerated than γ-secretase inhibitors is preferable. Indeed, this finding was supported by biochemical studies in which an effect of certain Non-Steroidal Anti-Inflammatory Drugs (NSAIDs) on γ-secretase was shown (US 2002/0128319; Eriksen (2003) J. Clin. Invest. 1 12, 440). Specifically, these drugs were shown to shift γ-secretase cleavage of APP away from the amyloidogenic Aβ42 site towards cleavage at the Aβ37 and Aβ38 sites, such that the decrease in Aβ42 was accompanied by an increase in the shorter, less amyloidogenic Aβ peptides. No effect on Notch processing was observed. Potential limitations for the use of NSAIDs to prevent or treat AD include their inhibition of cyclooxygenase (COX) enzymes, which can lead to unwanted side effects, and their low CNS penetration (Peretto et al, 2005, J. Med. Chem. 48, 5705-5720). NSAID derivatives such as R-flurbiprofen (Flurizan™) that are devoid of COX inhibitory activity but retain the Aβ42 lowering activity were subsequently identified and progressed to clinical trials (Wilcock et al, 2008 Lancet Neurol. 7: 483-493). However, R-flurbiprofen (Flurizan™) failed to show efficacy in a Phase 3 clinical trial (Green et al, 2009 JAMA 302: 2557-2564) due to its weak potency and poor brain penetration. Other patent literature on GSMs include WO-2009/032277 which relates to heterocyclic compounds useful as γ-secretase modulators and WO-2010/083141, WO-2011/086098 which relate to bicyclic compounds for the reduction of beta-amyloid production.

There is a strong need for novel compounds which modulate γ-secretase activity thereby opening new avenues for the treatment of AD. It is an object of the present invention to overcome or ameliorate at least one of the disadvantages of the prior art, or to provide a useful alternative. It is accordingly an object of the present invention to provide such novel compounds.

DETAILED DESCRIPTION

The present invention provides compounds of Formula (I)

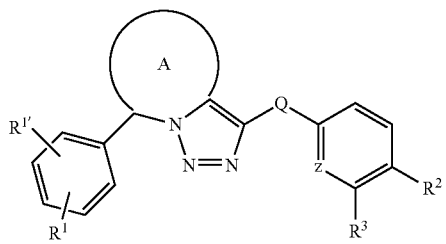

(I)

Wherein
A denotes a 5- to 7-membered saturated carbocyclic ring wherein 1 —CH$_2$— group may be replaced by an oxygen atom.
R$^1$R$^{1'}$ are independently from one another selected from halogen, CF$_3$, C$_1$-C$_6$-alkyl optionally substituted with one to 3 Hal, C$_1$-C$_6$-alkoxy, CN, C$_1$-C$_6$-alkyl sulfonyl and amine.
Q is selected from a double bond, —NR$^4$—, —(CH$_2$)NR$^4$CO—, —NR$^4$CO— or —CONR$^4$—, and —CONR$^4$—
Z is CH or N,
R$^2$ is a 5- to 6-membered unsaturated or aromatic heterocyclic ring containing 1 to 3 heteroatoms independently selected from O, N or S and which may be substituted with 1 to 3 groups independently selected from C$_1$-C$_6$-alkyl, C$_1$-C$_6$ alkoxy,
R$^3$ is selected from H, C$_1$-C$_6$-alkoxy, CN, and halogen,
R$^4$ denotes H or C$_1$-C$_6$-alkyl,
and pharmaceutically acceptable derivatives, solvates, tautomers, salts, hydrates and stereoisomers thereof, including mixtures thereof in all ratios.
In Formula (I), the group

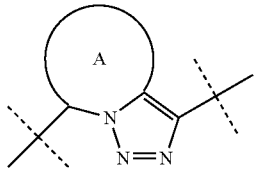

preferably denotes one of the following groups:

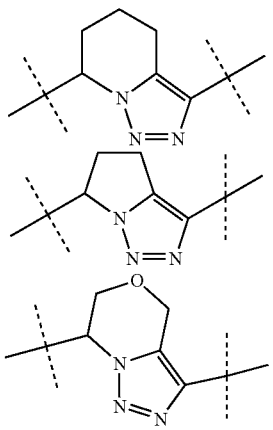

The groups R$^1$ and R$^{1'}$ are preferably selected from Hal and CF$_3$.
In Formula (I), R$^2$ preferably denotes one of the following groups: methylpyridine, methylimidazole and methylpyrazole.
Q preferably denotes a group selected from —NH—, —(CH$_2$)NHCO—, —NHCO— or —CONH—, and —CONH—,
In particular, the present invention also encompasses the compounds of Formula (I')

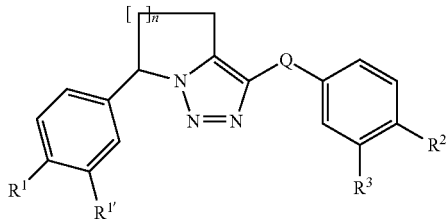

(I')

Wherein R$^1$, R$^{1'}$, R$^2$, R$^3$ and Q are as above defined and wherein n is 1 or 2.
More preferably, in Formulae (I) and (I'), R$^1$ denotes Hal or CF$_3$, and R$^{1'}$ is H or Hal.
In Formulae (I) and (I'), Q most preferably denotes NH, —CONH—, CON(CH$_3$)— or —NHCO—
Preferred compounds are selected from the following group:

| Example No | Structure |
|---|---|
| 1 | 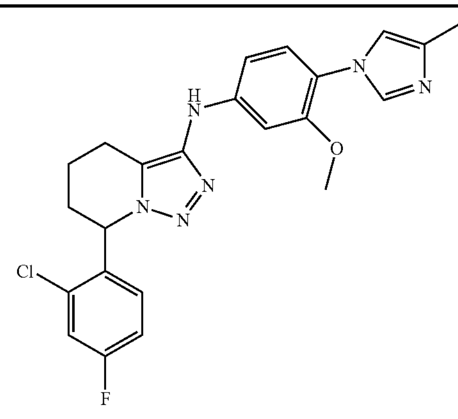 |

-continued
| Example No | Structure |
|---|---|
| 2 | 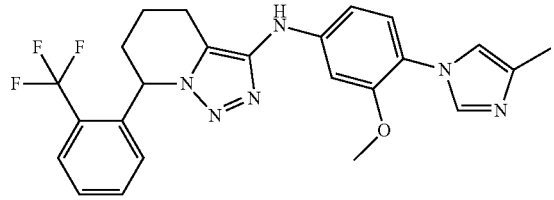 [SMILES: COc1cc(Nc2nnn3c2CCCC3c2ccccc2C(F)(F)F)ccc1-n1cnc(C)c1] |
| 3 | 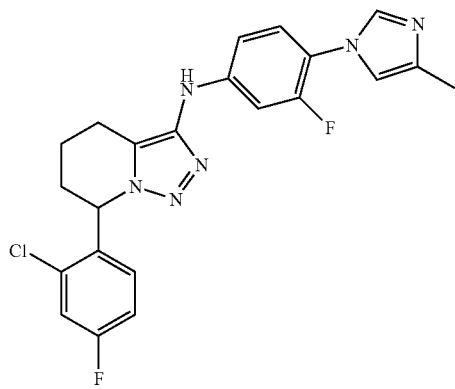 [SMILES: Cc1cn(-c2ccc(Nc3nnn4c3CCCC4c3ccc(F)cc3Cl)cc2F)cn1] |
| 4 | 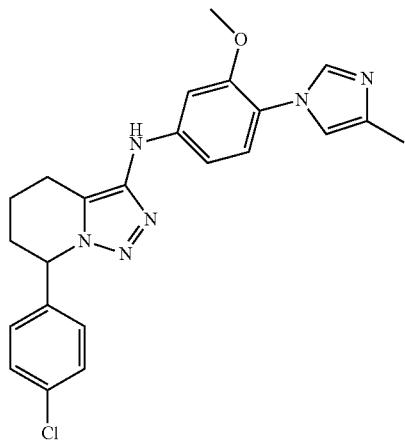 |
| 5 | 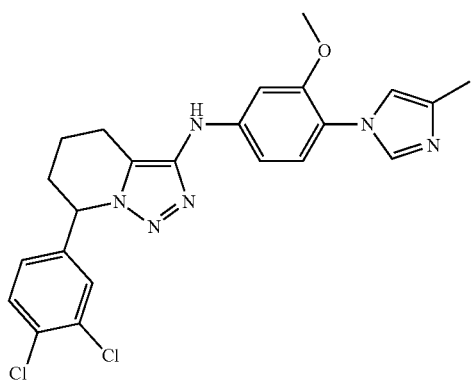 [SMILES: COc1cc(Nc2nnn3c2CCCC3c2ccc(Cl)c(Cl)c2)ccc1-n1cnc(C)c1] |

-continued
| Example No | Structure |
|---|---|
| 6 | 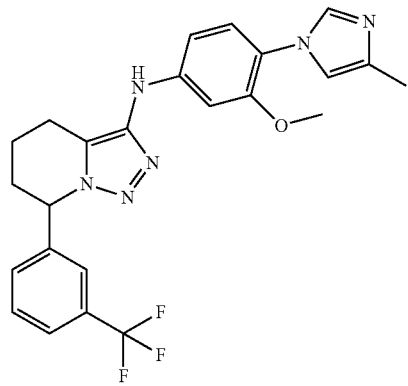 [SMILES: COc1cc(Nc2nnn3c2CCCC3c2cccc(C(F)(F)F)c2)ccc1-n1cnc(C)c1] |
| 7 | 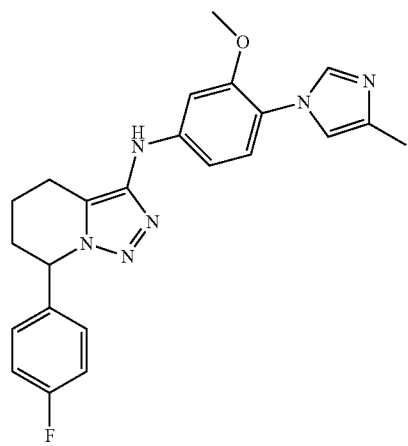 [SMILES: COc1cc(Nc2nnn3c2CCCC3c2ccc(F)cc2)ccc1-n1cnc(C)c1] |
| 8 | 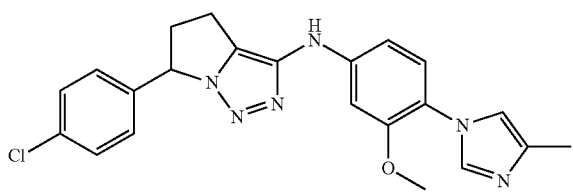 [SMILES: COc1cc(Nc2nnn3c2CCC3c2ccc(Cl)cc2)ccc1-n1cnc(C)c1] |
| 9 | 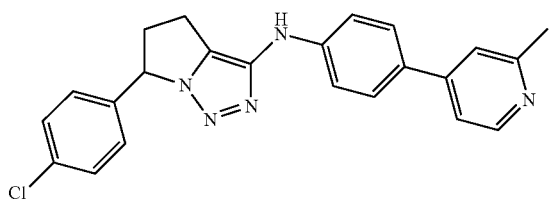 [SMILES: Cc1cc(-c2ccc(Nc3nnn4c3CCC4c3ccc(Cl)cc3)cc2)ccn1] |
| 10 | 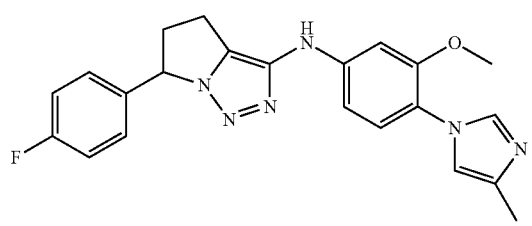 [SMILES: COc1cc(Nc2nnn3c2CCC3c2ccc(F)cc2)ccc1-n1cnc(C)c1] |

-continued
| Example No | Structure |
|---|---|
| 11 | 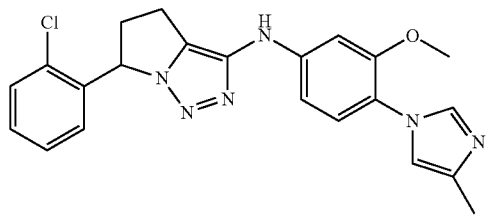 [SMILES: COc1cc(Nc2nnn3c2CCC3c2ccccc2Cl)ccc1-n1cnc(C)c1] |
| 12 | 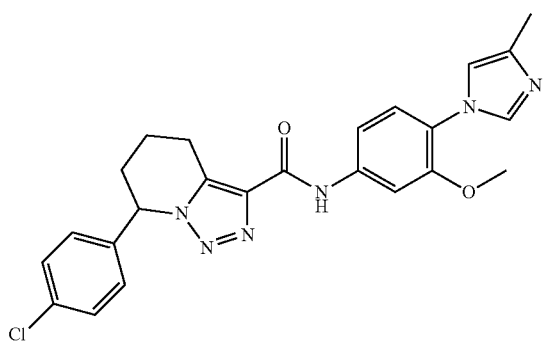 [SMILES: COc1cc(NC(=O)c2nnn3c2CCCC3c2ccc(Cl)cc2)ccc1-n1cnc(C)c1] |
| 13 | 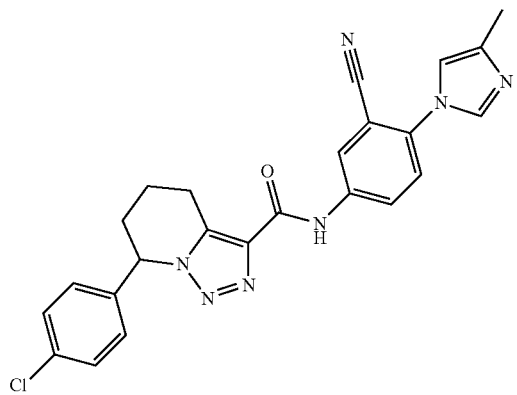 [SMILES: Cc1cn(-c2ccc(NC(=O)c3nnn4c3CCCC4c3ccc(Cl)cc3)cc2C#N)cn1] |
| 14 | 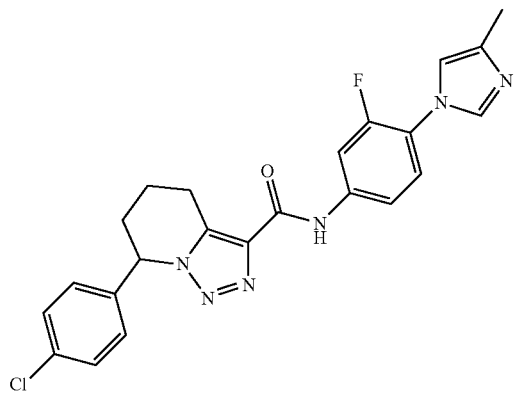 [SMILES: Cc1cn(-c2ccc(NC(=O)c3nnn4c3CCCC4c3ccc(Cl)cc3)cc2F)cn1] |

-continued
| Example No | Structure |
|---|---|
| 15 | 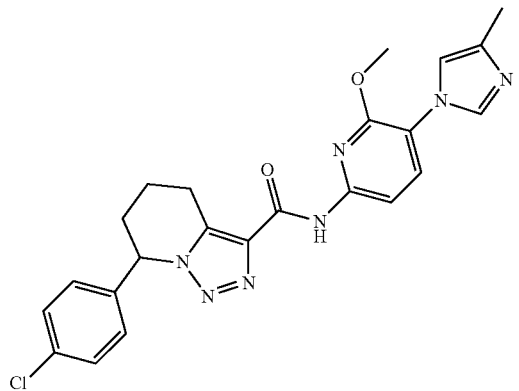 [SMILES: COc1nc(NC(=O)c2nnn3c2CCCC3c2ccc(Cl)cc2)ccc1-n1cnc(C)c1] |
| 16 | 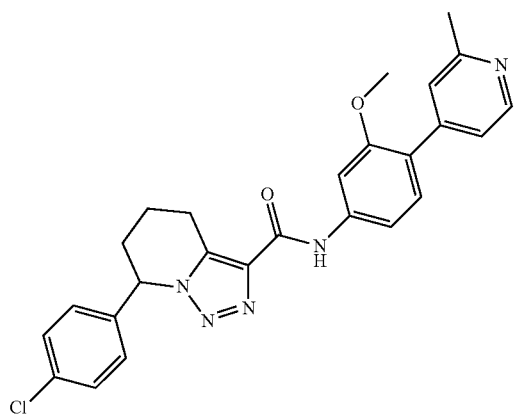 [SMILES: COc1cc(NC(=O)c2nnn3c2CCCC3c2ccc(Cl)cc2)ccc1-c1ccnc(C)c1] |
| 17 | 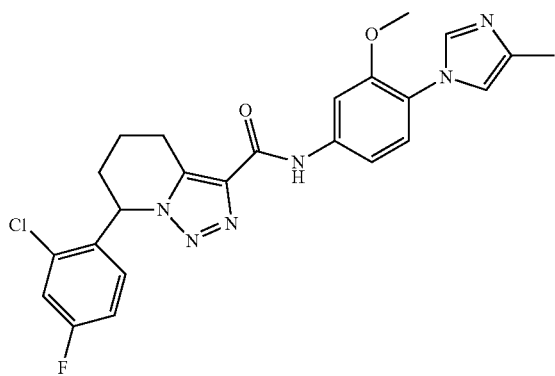 [SMILES: COc1cc(NC(=O)c2nnn3c2CCCC3c2ccc(F)cc2Cl)ccc1-n1cnc(C)c1] |
| 18 | 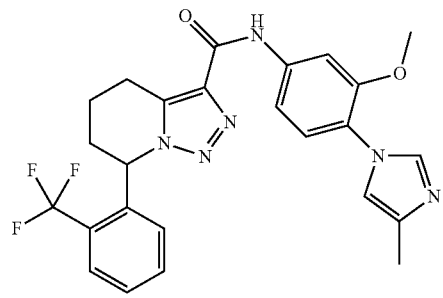 [SMILES: COc1cc(NC(=O)c2nnn3c2CCCC3c2ccccc2C(F)(F)F)ccc1-n1cnc(C)c1] |

| Example No | Structure |
|---|---|
| 19 | 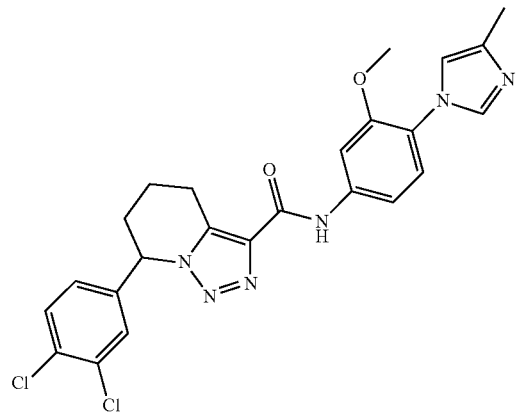 [SMILES: COc1cc(NC(=O)c2nnn3c2CCCC3c2ccc(Cl)c(Cl)c2)ccc1-n1cnc(C)c1] |
| 20 | 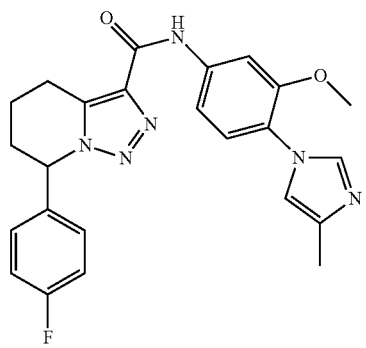 [SMILES: COc1cc(NC(=O)c2nnn3c2CCCC3c2ccc(F)cc2)ccc1-n1cnc(C)c1] |
| 21 | 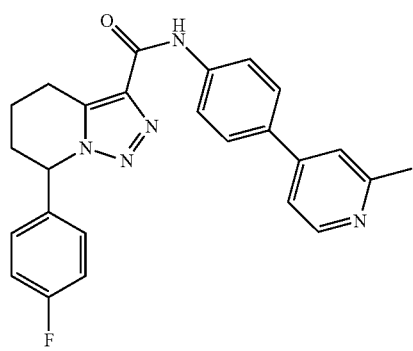 [SMILES: Cc1cc(-c2ccc(NC(=O)c3nnn4c3CCCC4c3ccc(F)cc3)cc2)ccn1] |
| 22 | 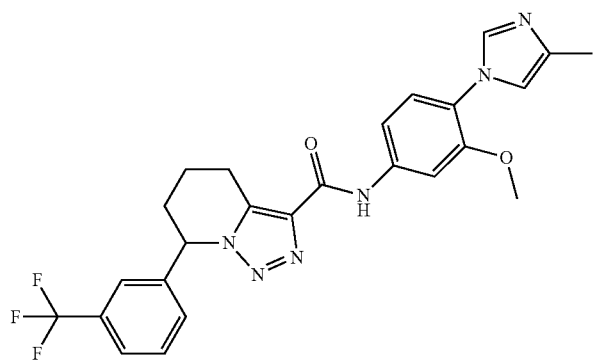 [SMILES: COc1cc(NC(=O)c2nnn3c2CCCC3c2cccc(C(F)(F)F)c2)ccc1-n1cnc(C)c1] |

| Example No | Structure |
|---|---|
| 23 | 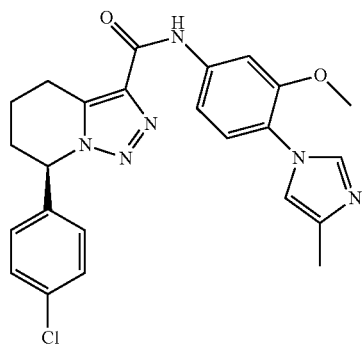 [SMILES: COc1cc(NC(=O)c2nnn3c2CCC[C@@H]3c2ccc(Cl)cc2)ccc1-n1cnc(C)c1] |
| 24 | 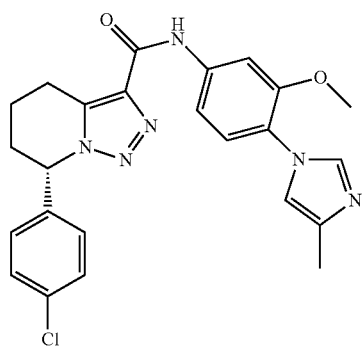 [SMILES: COc1cc(NC(=O)c2nnn3c2CCC[C@H]3c2ccc(Cl)cc2)ccc1-n1cnc(C)c1] |
| 25 | 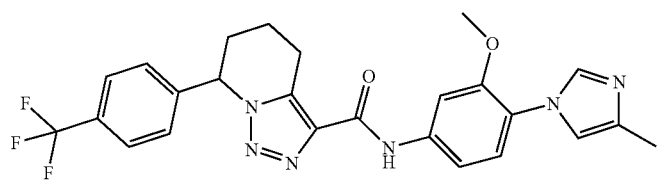 [SMILES: COc1cc(NC(=O)c2nnn3c2CCCC3c2ccc(C(F)(F)F)cc2)ccc1-n1cnc(C)c1] |
| 26 | 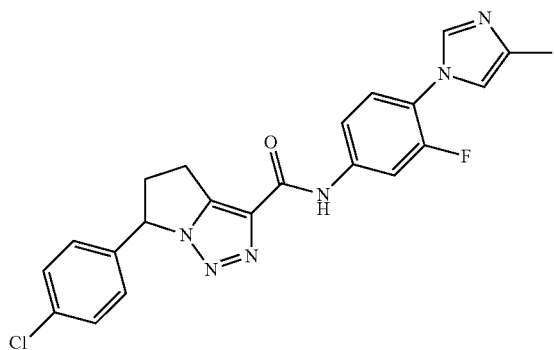 [SMILES: Cc1cn(-c2ccc(NC(=O)c3nnn4c3CCC4c3ccc(Cl)cc3)cc2F)cn1] |
| 27 | 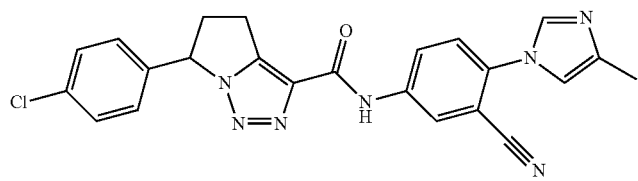 [SMILES: Cc1cn(-c2ccc(NC(=O)c3nnn4c3CCC4c3ccc(Cl)cc3)cc2C#N)cn1] |

-continued
| Example No | Structure |
|---|---|
| 28 | 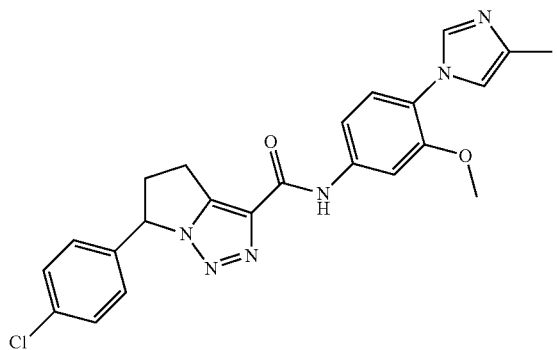 [SMILES: COc1cc(NC(=O)c2nnn3c2CCC3c2ccc(Cl)cc2)ccc1-n1cnc(C)c1] |
| 29 | 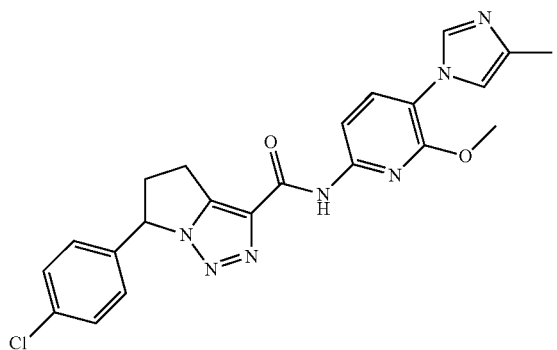 [SMILES: COc1nc(NC(=O)c2nnn3c2CCC3c2ccc(Cl)cc2)ccc1-n1cnc(C)c1] |
| 30 | 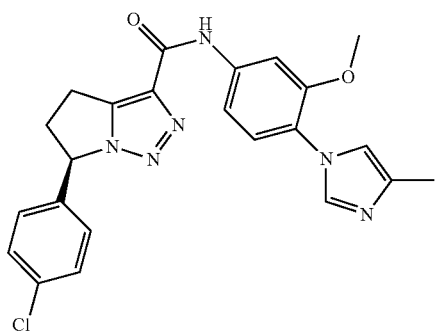 [SMILES: COc1cc(NC(=O)c2nnn3c2CC[C@@H]3c2ccc(Cl)cc2)ccc1-n1cnc(C)c1] |
| 31 | 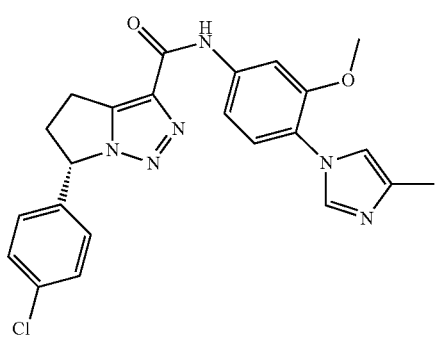 [SMILES: COc1cc(NC(=O)c2nnn3c2CC[C@H]3c2ccc(Cl)cc2)ccc1-n1cnc(C)c1] |

| Example No | Structure |
| --- | --- |
| 32 | 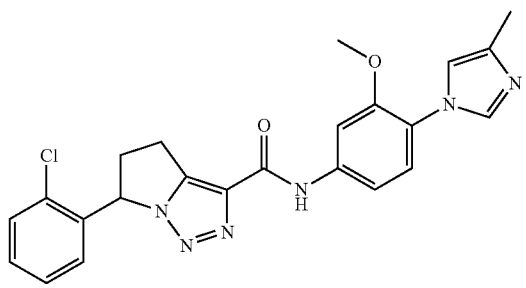 [SMILES: COc1cc(NC(=O)c2nnn3c2CCC3c2ccccc2Cl)ccc1-n1cnc(C)c1] |
| 33 | 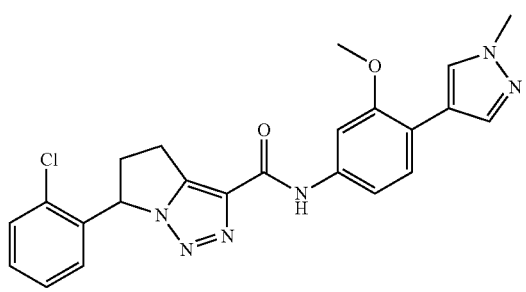 [SMILES: COc1cc(NC(=O)c2nnn3c2CCC3c2ccccc2Cl)ccc1-c1cnn(C)c1] |
| 34 | 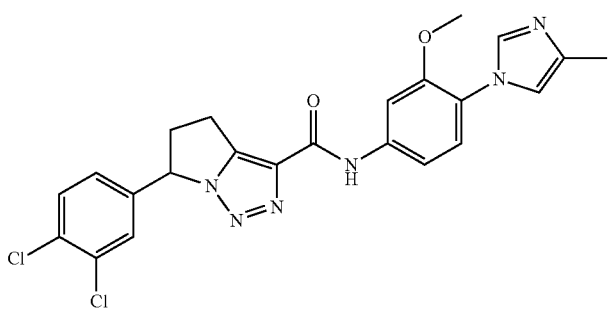 [SMILES: COc1cc(NC(=O)c2nnn3c2CCC3c2ccc(Cl)c(Cl)c2)ccc1-n1cnc(C)c1] |
| 35 | 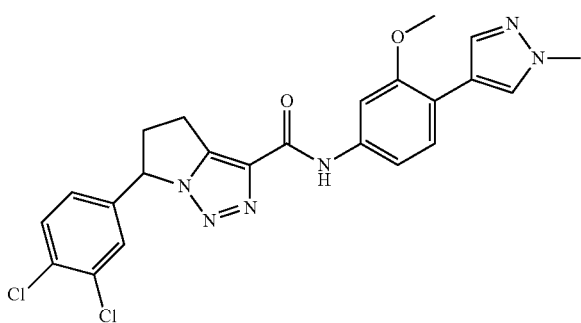 [SMILES: COc1cc(NC(=O)c2nnn3c2CCC3c2ccc(Cl)c(Cl)c2)ccc1-c1cnn(C)c1] |
| 36 | 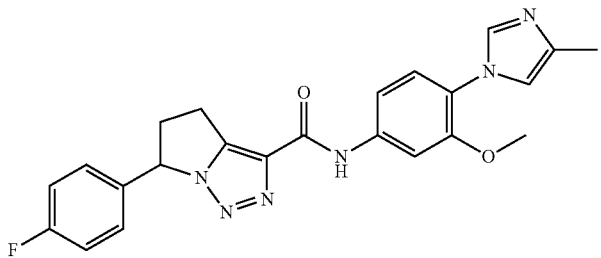 [SMILES: COc1cc(NC(=O)c2nnn3c2CCC3c2ccc(F)cc2)ccc1-n1cnc(C)c1] |

-continued

| Example No | Structure |
|---|---|
| 37 | 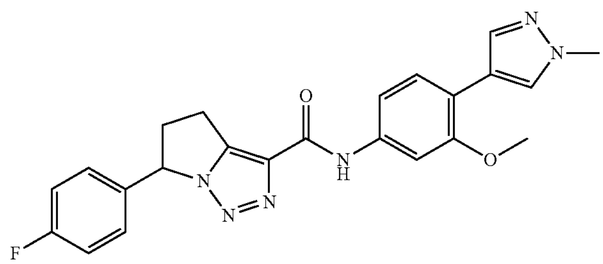 [SMILES: COc1cc(NC(=O)c2nnn3c2CCC3c2ccc(F)cc2)ccc1-c1cnn(C)c1] |
| 38 | 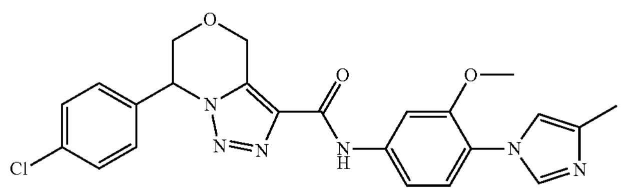 [SMILES: COc1cc(NC(=O)c2nnn3c2COCC3c2ccc(Cl)cc2)ccc1-n1cnc(C)c1] |
| 39 | 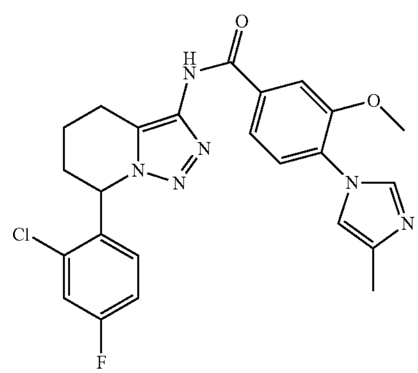 [SMILES: COc1cc(C(=O)Nc2nnn3c2CCCC3c2ccc(F)cc2Cl)ccc1-n1cnc(C)c1] |
| 40 | 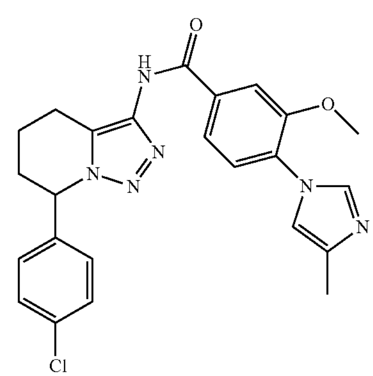 [SMILES: COc1cc(C(=O)Nc2nnn3c2CCCC3c2ccc(Cl)cc2)ccc1-n1cnc(C)c1] |
| 41 | 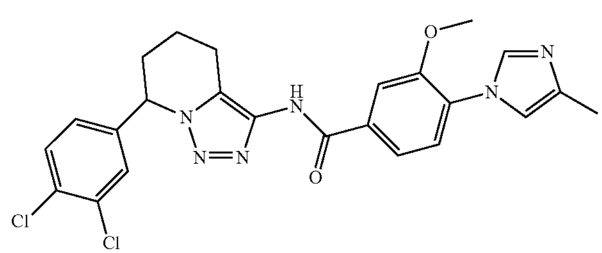 [SMILES: COc1cc(C(=O)Nc2nnn3c2CCCC3c2ccc(Cl)c(Cl)c2)ccc1-n1cnc(C)c1] |

-continued
| Example No | Structure |
|---|---|
| 42 | 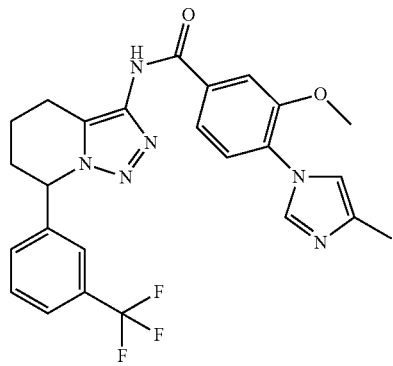 [SMILES: COc1cc(C(=O)Nc2nnn3c2CCCC3c2cccc(C(F)(F)F)c2)ccc1-n1cnc(C)c1] |
| 43 | 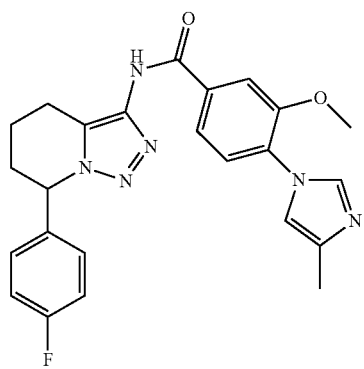 [SMILES: COc1cc(C(=O)Nc2nnn3c2CCCC3c2ccc(F)cc2)ccc1-n1cnc(C)c1] |
| 44 | 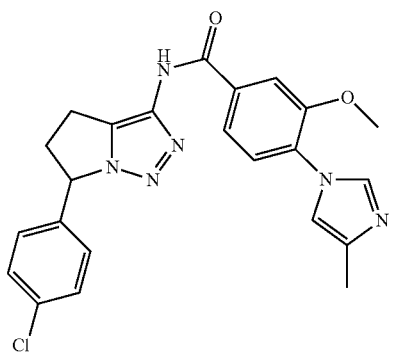 [SMILES: COc1cc(C(=O)Nc2nnn3c2CCC3c2ccc(Cl)cc2)ccc1-n1cnc(C)c1] |
| 45 | 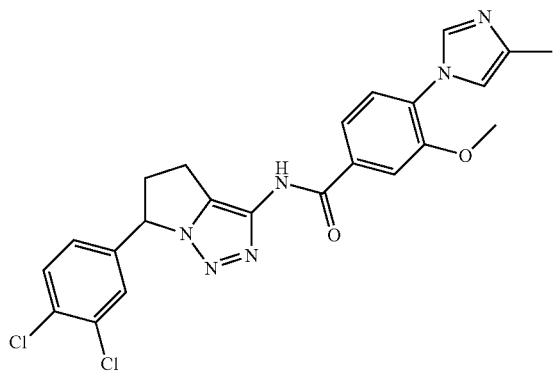 [SMILES: COc1cc(C(=O)Nc2nnn3c2CCC3c2ccc(Cl)c(Cl)c2)ccc1-n1cnc(C)c1] |

| Example No | Structure |
|---|---|
| 46 | 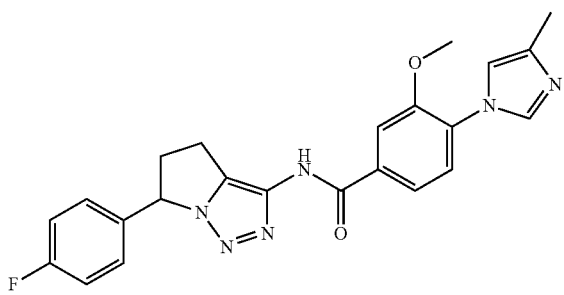 [SMILES: COc1cc(C(=O)Nc2nnn3c2CCC3c2ccc(F)cc2)ccc1-n1cnc(C)c1] |
| 47 | 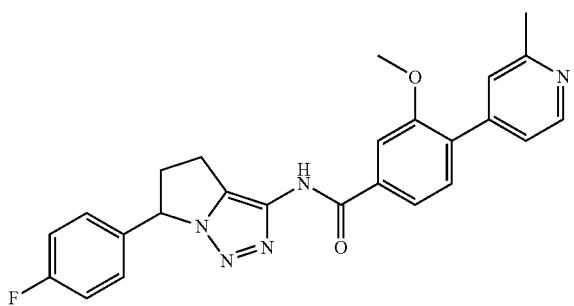 [SMILES: COc1cc(C(=O)Nc2nnn3c2CCC3c2ccc(F)cc2)ccc1-c1ccnc(C)c1] |
| 48 | 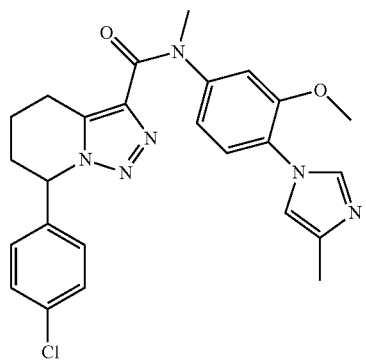 [SMILES: COc1cc(N(C)C(=O)c2nnn3c2CCCC3c2ccc(Cl)cc2)ccc1-n1cnc(C)c1] |

The following abbreviations refer respectively to the definitions below:

aq (aqueous), h (hour), g (gram), L (liter), mg (milligram), MHz (Megahertz), μM (micromolar), min (minute), mmol (millimole), mM (millimolar), eq (equivalent), mL (milliliter), μL (microliter), ACN (acetonitrile), BOC (tert-butoxycarbonyl), CDCl$_3$ (deuterated chloroform), CD$_3$OD (deuterated methanol), CH$_3$CN (acetonitrile), DCM (dichloromethane), dba (dibenzylideneacetone), DIPEA (di-isopropylethylamine), DMF (dimethylformamide), DMSO (dimethylsulfoxide), DMSO-d$_6$ (deuterated dimethylsulfoxide), DPPA (diphenylphosphoryl azide), ESI (Electro-spray ionization), EtOAc (ethyl acetate), Et$_2$O (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MeOH (methanol), MgSO$_4$ (magnesium sulfate), MS (mass spectrometry), MTBE (methyl tert-butyl ether), MW (microwave), NaHCO$_3$ (sodium bicarbonate), NaBH$_4$ (sodium borohydride), NMM (N-methyl morpholine), NMR (Nuclear Magnetic Resonance), Py (pyridine), Rt (retention time), TEA (triethylamine), TFA (trifluoroacetic acid), THF (tetrahydrofuran), TLC (Thin Layer Chromatography), UV (Ultraviolet).

In general, the fused triazole compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Depending on the nature of $R^1$, $R^{1'}$, $R^2$, $R^3$, A, Q and Z, different synthetic strategies may be selected for the synthesis of compounds of Formula (I). In the process illustrated in the following schemes, $R^1$, $R^{1'}$, $R^2$, $R^3$, A, Q and Z are as above-defined in the description unless otherwise mentioned.

When compounds of Formula (I) are obtained as mixture of enantiomers, they can be separated by conventional methods such as chiral HPLC column, such as but not limited to the methods described below in the examples.

Compounds of Formula (I), wherein $R^1$, $R^{1'}$, $R^2$, $R^3$, A, Q and Z are defined as above, can be prepared from the ester of Formula (II), wherein $R^1$ and A are defined as above and R is a small alkyl group, such as but not limited to Me, Et, tBu (Scheme 1). Manipulation of the triazole ester (II) to the corresponding amine (III), wherein $R^1$ and A are defined as above, can be achieved by conversion of the ester to the corresponding carboxamide and then treatment of this amide with bromine in aqueous sodium hydroxide at temperatures between 25° C. and 80° C. Alternatively, treatment of the carboxylic acid (IV) resulting from ester (II) with DPPA in refluxing tert-butanol will provide the carbamate ester that can be deprotected with a suitable acid such as HCl or TFA in a solvent such as dioxan or DCM. The ester (II) and the amine (III) can be used to prepare the amide and amino linked final compounds of Formula (I) reported herein. Typically, the ester (II) can be converted into the carboxylic acid (IV) that can be reacted with a range of amines (XVIII), wherein $R^2$, $R^3$ and Z are defined as above and D is an amino group, using a typical uronium coupling agent, such as HATU, in a solvent such as DMF or DCM at 25° C. Alternatively, the amine (III) can be reacted with an appropriate aromatic halide (XVIII), wherein $R^2$, $R^3$ and Z are defined as above and D is a halide or sulfonate ester, with Pd catalysis in a solvent such as dioxan at temperatures between 50° C. and 100° C. Amine (III) can also be derivatised with a range of carboxylic acids (XVIII), wherein $R^2$, $R^3$ and Z are defined as above and D is carboxylic acid, using the typical uronium coupling conditions described herein.

Scheme 1

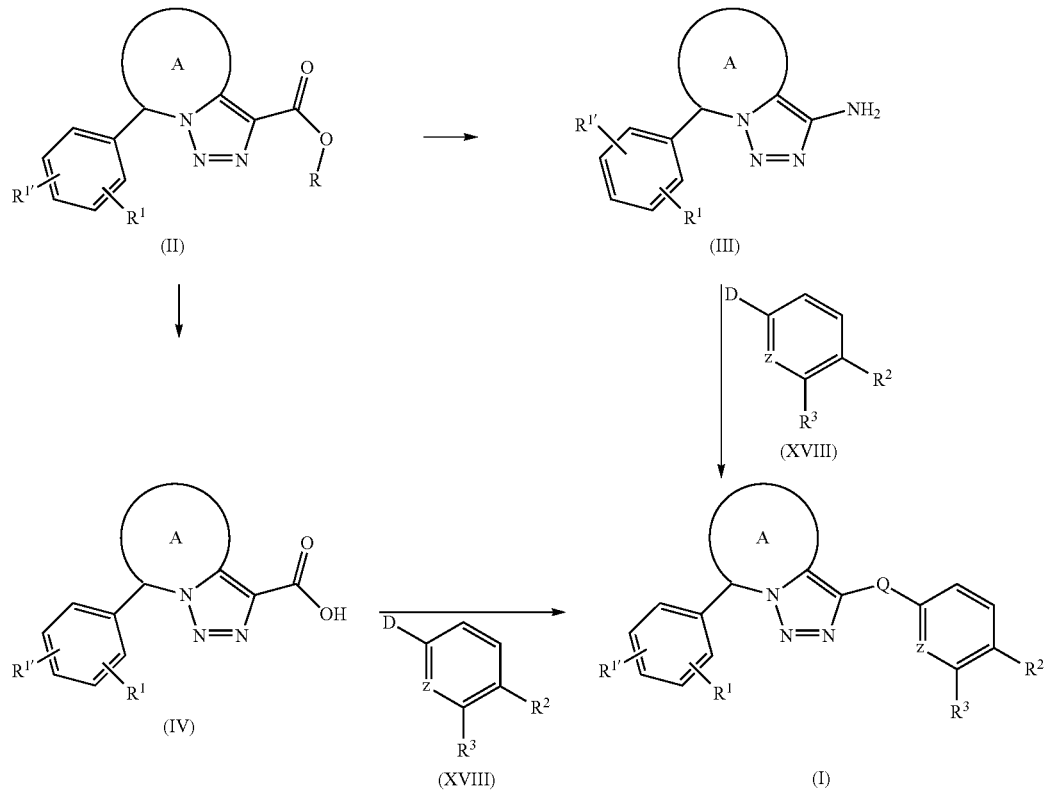

The method for preparing amine derivatives of Formula (III) selected below:
7-(3,4-dichlorophenyl)-4,5,6,7-tetrahydro-[1,2,3]triazolo[1,5-c]pyridin-3-amine
7-(4-chlorophenyl)-4,5,6,7-tetrahydro-[1,2,3]triazolo[1,5-c]pyridin-3-amine
7-(4-fluorophenyl)-4,5,6,7-tetrahydro-[1,2,3]triazolo[1,5-a]pyridin-3-amine
7-[3-(trifluoromethyl)phenyl]-4,5,6,7-tetrahydro-[1,2,3]triazolo[1,5-a]pyridin-3-amine
7-[2-(trifluoromethyl)phenyl]-4,5,6,7-tetrahydro-[1,2,3]triazolo[1,5-c]pyridin-3-amine
7-(2-chloro-4-fluorophenyl)-4,5,6,7-tetrahydro-[1,2,3]triazolo[1,5-a]pyridin-3-amine
6-(4-chlorophenyl)-5,6-dihydro-4H-pyrrolo[1,2-c][1,2,3]triazol-3-amine
6-(2-chlorophenyl)-5,6-dihydro-4H-pyrrolo[1,2-c][1,2,3]triazol-3-amine 6-(3,4-dichlorophenyl)-5,6-dihydro-4H-pyrrolo[1,2-c][1,2,3]triazol-3-amine
6-(4-fluorophenyl)-5,6-dihydro-4H-pyrrolo[1,2-c][1,2,3]triazol-3-amine
is more particularly described in the examples.

The method for preparing carboxylic acid derivatives of Formula (IV) selected below:
7-(3,4-dichlorophenyl)-4,5,6,7-tetrahydro-[1,2,3]triazolo[1,5-a]pyridine-3-carboxylic acid
7-(4-chlorophenyl)-4,5,6,7-tetrahydro-[1,2,3]triazolo[1,5-a]pyridine-3-carboxylic acid
7-(2-chloro-4-fluorophenyl)-4,5,6,7-tetrahydro-[1,2,3]triazolo[1,5-a]pyridine-3-carboxylic acid
7-[2-(trifluoromethyl)phenyl]-4,5,6,7-tetrahydro-[1,2,3]triazolo[1,5-a]pyridine-3-carboxylic acid
7-(4-fluorophenyl)-4,5,6,7-tetrahydro[1,2,3]triazolo[1,5-a]pyridine-3-carboxylic acid
7-[3-(trifluoromethyl)phenyl]-4,5,6,7-tetrahydro[1,2,3]triazolo[1,5-a]pyridine-3-carboxylic acid
7-[4-(trifluoromethyl)phenyl]-4,5,6,7-tetrahydro[1,2,3]triazolo[1,5-a]pyridine-3-carboxylic acid
7-(4-chlorophenyl)-6,7-dihydro-4H [1,2,3]triazolo[5,1-c][1,4]oxazine-3-carboxylic acid
6-(4-fluorophenyl)-5,6-dihydro-4H-pyrrolo[1,2-c][1,2,3]triazole-3-carboxylic acid
6-(4-chlorophenyl)-5,6-dihydro-4H-pyrrolo[1,2-c][1,2,3]triazole-3-carboxylic acid
6-(2-chlorophenyl)-5,6-dihydro-4H-pyrrolo[1,2-c][1,2,3]triazole-3-carboxylic acid
6-(3,4-dichlorophenyl)-5,6-dihydro-4H-pyrrolo[1,2-c][1,2,3]triazole-3-carboxylic acid to Me, Et, tBu, can be prepared according to Scheme 2. Starting materials can be a suitably substituted alkyne alcohol (V) that is protected with an appropriate ether protecting group PG, such as tert-butyldimethylsilyl, tetrahydropyranyl or alkyl and wherein n=1-3. Acylation of the alkyne can be achieved with a base, such as butyllithium or lithium diisopropylamide, in a solvent such as THF or diethyl ether at temperatures between −78° C. and 0° C. A suitable acylating agent can include, amongst others, ethylchloroformate or di(tertbutyloxycarbonyl), thereby describing the R substituent. Removal of the protecting group PG according to standard conditions and then oxidation of the resultant alcohol with, for example, Dess-Martin periodinane, or pyridinium chlorochromate in DCM between 0° C. and 25° C. yields isolation of the aldehyde (VI). Reaction of the aldehyde with a suitably substituted phenyllithium, or phenyl Grignard reagent, can be achieved in THF or diethyl ether at temperatures from −78° C. to 0° C. Substitution of the phenyl group includes, but is not limited to, halogen, alkoxy, fluoroalkyl, fluoroalkoxy. Bromination of the resultant alcohol (VII) can be accomplished with reagents such as phosphorus tribromide in diethyl ether or DCM, or carbon tetrabromide/triphenyl phosphine in similar solvents and at temperatures between 0° C. and 25° C. Cyclisation to the triazole (IIa) can be achieved by treatment of (VII) with sodium azide in a solvent such as DMF or DMSO at temperatures between 40° C. and 100° C.

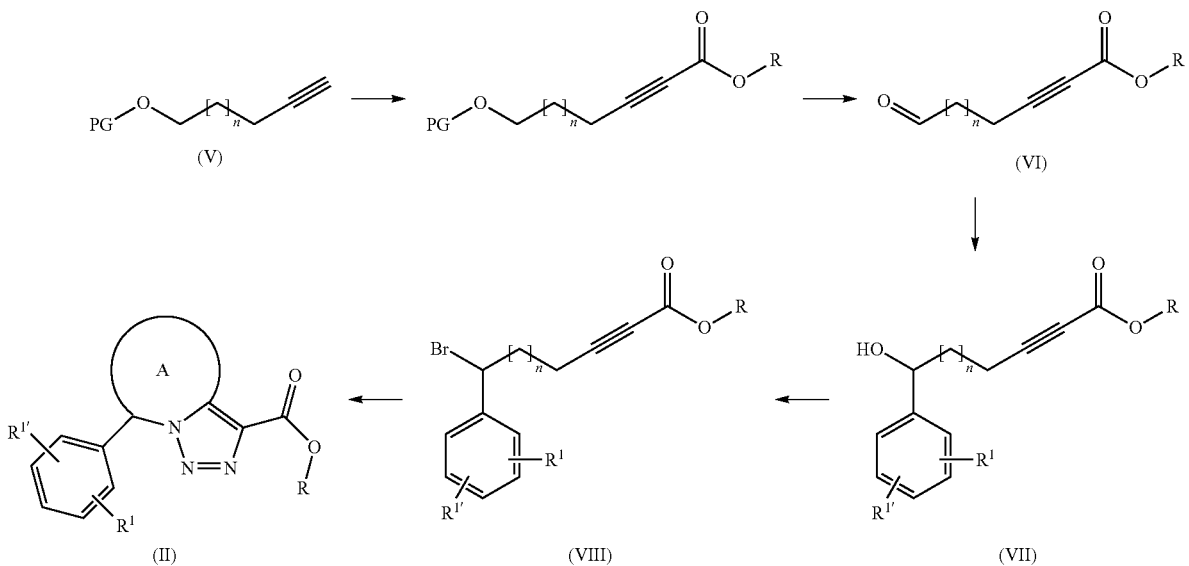

Scheme 2 is more particularly described in the examples.

Intermediates (XVIII), wherein $R^2$, $R^3$ and Z are define as above and D can be COOR, COOH, $NH_2$ or an halogen, are either commercially available or can be prepared according to reported literature (e.g. Pettersson, M. et al. Bioorg. Med. Chem. Lett. 2012, 22, 2906-2911, Lübbers, T. et al. Bioorg. Med. Chem. Lett. 2011, 21, 6554-6558).

Ester of Formula (II), wherein $R^1$ and A are defined as above and R is a small alkyl group, such as but not limited Optionally, the ring A can be substituted at alternative positions with substituents or heteroatoms that would be reflected in the protected alkyne alcohol (V). As illustration, ester of formula (IIa), wherein A denotes a 6-membered saturated carbocyclic ring with one —$CH_2$— group replaced by an oxygen atom, can be prepared according to Scheme 3. Epoxide (IX) can be opened with an azide group as nucleophile, such as but not limited to sodium azide. The resulting alcohol (X) can be alkylated with a propargyl group, yielding intermediate (XI). This intermediate is first acylated under similar conditions as described above, using a suitable acylating agent such as but not limited to ethylchloroformate or di(tertbutyloxycarbonyl), thereby describing the R substituent. Cyclization into triazole ester (IIa) is then observed at room temperature.

Scheme 3

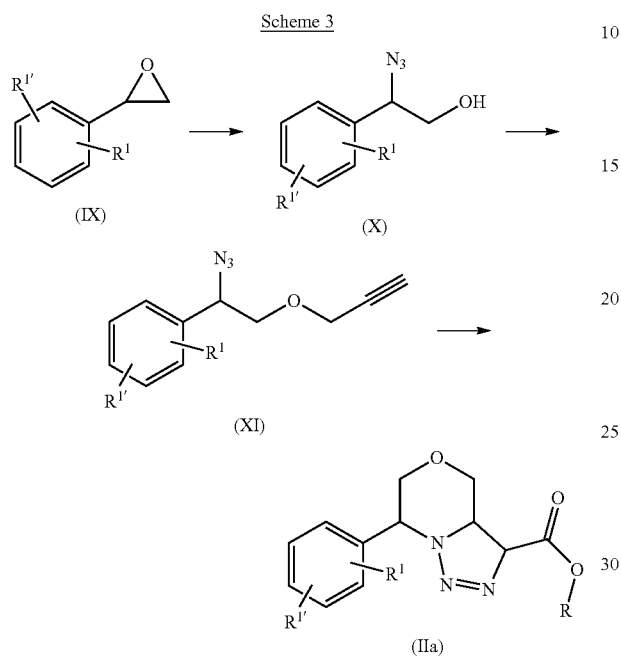

A further variation to the synthesis of ester of Formula (II) can be achieved as described in Scheme 4. A suitably substituted lactam (XII), prepared by those methods described in the prior art, or obtained commercially, can be converted into (XIII) with trimethyloxonium tetrafluoroborate in a solvent such as DCM or diethyl ether between 0° C. and 25° C. $R^1$ is described as above and the value of n can be 1 to 3. Substitution of the methoxy group can be achieved with a suitable nitroalkyl acetate, which thereby defines the nature of R group. Subsequent conversion of (XIV) into the triazole (IIb) can be accomplished in two stages—firstly reduction of the nitro group with a suitable metal in an acidic solvent e.g. zinc in acetic or hydrochloric acid, followed by treatment with tert-butylnitrite in an acidic solvent e.g. TFA. The triazole ester (IIb) can then be manipulated in the same way as that described herein.

Scheme 3

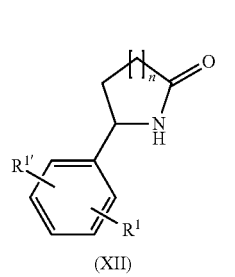

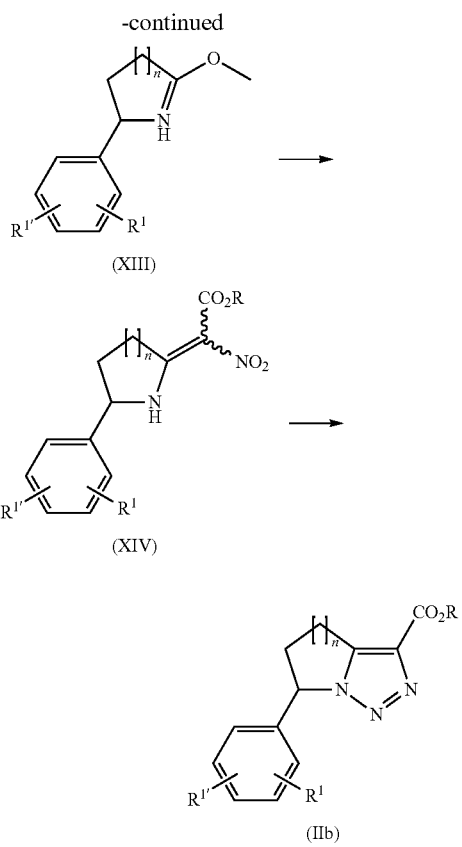

Alternatively, ester of Formula (IIc), wherein A is a six membered ring and $R^1$ is defined as above, can be prepared as described in Scheme 4. 2-Bromo-6-methyl pyridine can be transformed into ester (XV), using an appropriate base, such as lithium diisopropylamide, in a solvent such as THF or diethyl ether at temperatures between −78° C. and 0° C., followed by the addition of a suitable acylating agent. It can be selected from, amongst others, ethylchloroformate or di(tertbutyloxycarbonyl), thereby describing the R substituent. Subsequent conversion of (XV) into the triazole (XVI) can be accomplished with p-acetamidobenzenesulfonyl azide in the presence of a base such as but not limited to DBU (Chuprakov, S.; Hwang, F. W.; Gevorgyan, V. *Angew. Chem. Int. Ed.* 2007, 46, 4757-59). The resulting imidazopyridine (XVI) is then coupled with an aryl, wherein $R^1$ is defined as above. Ester of Formula (IIc) is obtained after reduction of intermediate (XVII) (Abarca, B. et al. *Tetrahedron* 1999, 55, 12881).

Scheme 4

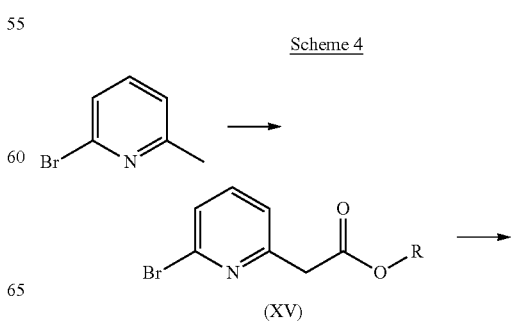

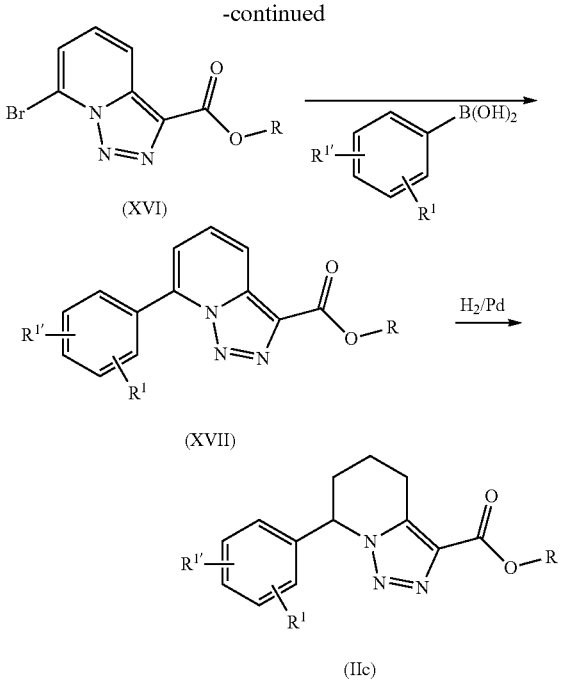

The method for preparing esters derivatives of Formula (II) selected below:
tert-butyl 7-(3,4-dichlorophenyl)-4,5,6,7-tetrahydro-[1,2,3]triazolo[1,5-a]pyridine-3-carboxylate
tert-butyl 7-(4-chlorophenyl)-4,5,6,7-tetrahydro-[1,2,3]triazolo[1,5-a]pyridine-3-carboxylate
tert-butyl 7-(2-chlorophenyl)-4,5,6,7-tetrahydro-[1,2,3]triazolo[1,5-a]pyridine-3-carboxylate
tert-butyl 7-[2-(trifluoromethyl)phenyl]-4,5,6,7-tetrahydro-[1,2,3]triazolo[1,5-a]pyridine-3-carboxylate
tert-butyl 7-(4-fluorophenyl)-4,5,6,7-tetrahydro[1,2,3]triazolo[1,5-a]pyridine-3-carboxylate
tert-butyl 7-[3-(trifluoromethyl)phenyl]-4,5,6,7-tetrahydro[1,2,3]triazolo[1,5-a]pyridine-3-carboxylate
tert-butyl 7-[4-(trifluoromethyl)phenyl]-4,5,6,7-tetrahydro[1,2,3]triazolo[1,5-a]pyridine-3-carboxylate
tert-butyl 7-(4-chlorophenyl)-6,7-dihydro-4H-[1,2,3]triazolo[5,1-c][1,4]oxazine-3-carboxylate
ethyl 6-(4-fluorophenyl)-5,6-dihydro-4H-pyrrolo[1,2-c][1,2,3]triazole-3-carboxylate
ethyl 6-(4-chlorophenyl)-5,6-dihydro-4H-pyrrolo[1,2-c][1,2,3]triazole-3-carboxylate
ethyl 6-(2-chlorophenyl)-5,6-dihydro-4H-pyrrolo[1,2-c][1,2,3]triazole-3-carboxylate
ethyl 6-(3,4-dichlorophenyl)-5,6-dihydro-4H-pyrrolo[1,2-c][1,2,3]triazole-3-carboxylate
is more particularly described in the examples.

Ester derivatives of Formula (II) are obtained as mixture of enantiomers and can be separated by chiral HPLC column, such as but not limited to the methods described below in the examples.

Compounds of this invention can be isolated in association with solvent molecules by crystallization from evaporation of an appropriate solvent. The pharmaceutically acceptable acid addition salts of the compounds of formula (I), and related formulae which contain a basic center may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I), and related formulae, which contain an acid center, with a suitable base. Both types of salts may be formed or interconverted using ion-exchange resin techniques.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

General Methods

All NMRs were obtained at 400 MHz on a Bruker instrument.

The MS data were obtained either with an LC/MS Waters ZMD (ESI) or a Micromass ZQ, single quadrapole LC-MS (ESCI).

IUPAC names were generated using the Cambridgesoft Chemistry Cartridge software.

All reactions involving air- or moisture-sensitive reagents were performed under a nitrogen atmosphere using dried solvents and glassware.

HPLC methods (retention times refer to compounds purified by the following methods).

Method A: Column:—Waters Xterra MS 5 μm C18, 100×4.6 mm, eluting with ACN/10 mM ammonium bicarbonate (95% ACN after 4 min) and a flow rate of 2 mL/min.

Method B: Column:—Phenomenex Luna 5 μm C18 (2), 100×4.6 mm, eluting with ACN/water/0.1% formic acid (100% ACN after 3.5 mM) and a flow rate of 2 mL/min.

Method C: Column:—Phenomenex, Gemini NX, 3 μm C18, 150×4.6 mm, eluting with ACN/10 mM ammonium bicarbonate (100% ACN after 9 min) and a flow rate of 1 mL/min.

Method D: Column:—Supelco, Ascentis® Express C18 or Hichrom Halo C18, 2.7 μm C18, 150×4.6 mm, eluting with ACN/water/0.1% formic acid (100% ACN after 9 min) with a flow rate of 1 mL/min.

Method E: Column:—Hichrom ACE 3 C18-AR mixed mode column, 2.7 μm C18, 100×4.6 mm, eluting with ACN/water/0.1% formic acid (100% ACN after 12 min) with a flow rate of 1 mL/min.

Method F: Column:—Chiralpak IC, 250×4.6 mm×5 μm, eluting with 50/50 EtOH (0.1% formic acid)/heptane with a flow rate of 1 mL/min.

Method G: Column:—Chiralpak IB, 250×4 6 mm×5 μm, eluting with 50/50 IPA/MeOH (50/50/0.1% formic acid)/heptane with a flow rate of 4 mL/min.

Method H: Column:—X-Bridge C8, 50×4.6 mm×3.5 μm; eluting with 0.1% TFA in H₂O, and 0.1% TFA in ACN with a flow rate of 2.0 mL/min.

Method I: Chiralpak IC (Daicel), 250×20 mm; eluting with heptane (ethanol with 0.1% diethylamine) in a ratio 20/80, at flow rate of 10 ml/min, with detection UV at 254 nm.

Analytical methods (a-i) are referred to in the tables of data outlined in the document below.

The mass directed preparative HPLC purifications were carried out with a Waters Fractionlynx preparative HPLC system (2525 pump, 2996/2998 UV/VIS detector, 2767 liquid handler). The Waters 2767 liquid handler acted as both auto-sampler and fraction collector.

The column used for the preparative purification of the compounds was a Waters Sunfire OBD Phenomenex Luna Phenyl Hexyl or Waters Xbridge Phenyl at 10 um 19×150 mm.

Appropriate focused gradients were selected based on acetonitrile and methanol solvent systems under either acidic or basic conditions. The standard gradient used was 5% ACN to 20% over 1 min, hold 1 min, to 80% ACN over 5 min, hold 4 min Followed by 1 min 100% ACN and 1.5 min re-equilibration at initial conditions. A flow rate of 20 mL/min was used.

Synthesis of Intermediates-1

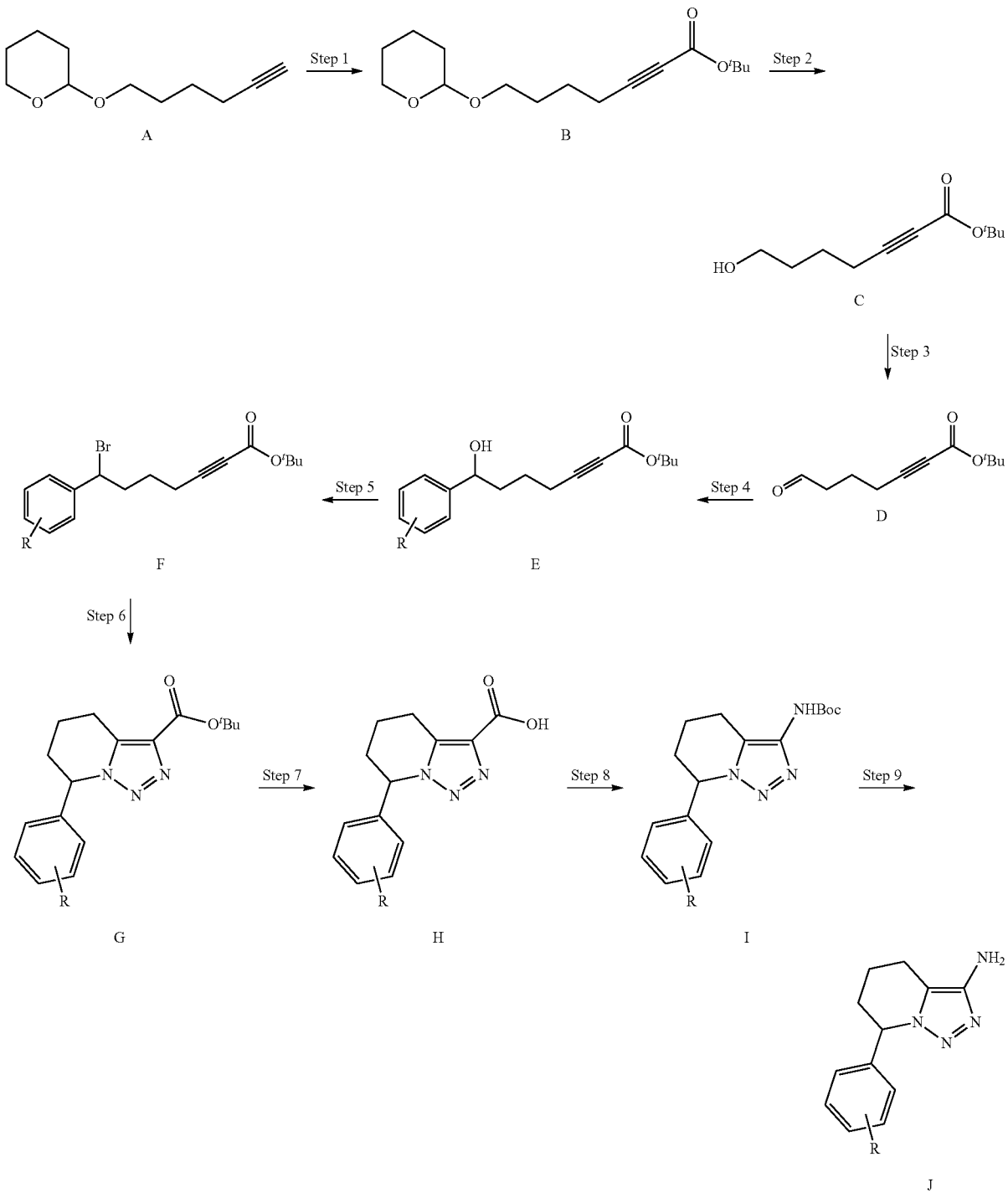

Step 1: tert-butyl 7-(tetrahydro-2H-pyran-2-yloxy)hept-2-ynoate B 2-(Hex-5-ynyloxy)tetrahydro-2H-pyran A (16 g, 87.9 mmol, described in EP1144368) was dissolved in THF (120 mL) and cooled to −78° C. under a nitrogen atmosphere. n-Butyl lithium (1.6 M in hexane, 60 mL, 96 mmol) was added dropwise over 45 minutes maintaining an internal temperature below −65° C. The mixture was then stirred for 1.5 hours at −78° C. A solution of di-tert-butyl dicarbonate (21 g, 96 mmol) in THF (40 mL) was added slowly at −78° C. Once addition was complete, the mixture was allowed to warm to 25° C. slowly over 2 hours. The mixture was then cooled to 0° C., quenched with saturated aqueous NH$_4$Cl solution, and extracted with Et$_2$O. The combined organic phases were dried (MgSO$_4$), filtered and evaporated under vacuum to give tert-butyl 7-(tetrahydro-2H-pyran-2-yloxy)hept-2-ynoate B (23.7 g, 87 mmol, 99%) as a yellow oil. $^1$H NMR δ (ppm)(CHCl$_3$-d): 4.57 (1H, d, J=4.25 Hz), 3.90-3.82 (1H, m), 3.80-3.71 (1H, m), 3.53-3.46 (1H, m), 3.44-3.37 (1H, m), 2.35 (2H, t, J=6.56 Hz), 2.06-1.28 (19H, m).

Step 2: tert-butyl 7-hydroxyhept-2-ynoate C tert-Butyl 7-(tetrahydro-2H-pyran-2-yloxy)hept-2-ynoate B (23.7 g 87 mmol) was dissolved in MeOH (175 mL) and water (17.5 mL) was added followed by p-toluene sulfonic acid (2 g 10.5 mmol). The mixture was stirred at 25° C. for 22 hours. Reaction progress was followed by TLC. Once the reaction was deemed complete, the mixture was treated with aqueous NaHCO$_3$ solution (4 g NaHCO$_3$ in 20 mL water) and stirred for 10 minutes before being concentrated in vacuo to remove the majority of the MeOH. The resultant slurry was extracted with Et$_2$O (×2) and the combined organic extracts were washed with brine, dried (MgSO$_4$), filtered and evaporated under vacuum to give 17 g of a crude oil. The crude product was purified by column chromatography using gradient elution of 0-50% EtOAc in iso-hexane to give pure tert-butyl 7-hydroxyhept-2-ynoate C (10 g, 53.4 mmol, 62%) as a colourless liquid. $^1$H NMR δ (ppm)(CHCl$_3$-d): 3.67 (2H, t, J=5.40 Hz), 2.38-2.33 (2H, m), 1.70-1.65 (4H, m), 1.49 (9H, s), 1.35 (1H, t, J=5.33 Hz).

Step 3: tert-butyl 7-oxohept-2-ynoate D

A solution of oxalyl chloride (12.8 g, 100 mmol, 8.66 mL) in DCM (225 mL) was cooled to −78° C. in a three-neck round bottom flask under a nitrogen atmosphere. A solution of DMSO (9.45 g, 120 mmol, 8.6 mL) in DCM (5 mL) was added dropwise via dropping funnel and the mixture was stirred for 15 minutes. A solution of tert-butyl 7-hydroxyhept-2-ynoate C (10 g, 50 mmol) in DCM (20 mL) was added dropwise, maintaining a temperature of −78° C., to give a white suspension which was stirred for a further 15 minutes. Triethylamine was then added slowly and the mixture was stirred for 15 minutes at −78° C. before slowly warming to 25° C. and then stirring for a further 30 minutes. The reaction mixture was poured onto water and the organic phase was separated. The organic phase was then washed with aqueous 1N HCl solution, then brine, dried (MgSO$_4$), and evaporated under vacuum to give tert-butyl 7-oxohept-2-ynoate D (10 g, 50 mmol, quant.) as a pale yellow oil. $^1$H NMR δ (ppm)(CHCl$_3$-d): 9.80 (1H, s), 2.66-2.59 (2H, m), 2.39 (2H, t, J=6.92 Hz), 1.90 (2H, p, J=7.05 Hz), 1.49 (9H, s).

Step 4: Intermediate E tert-Butyl 7-oxohept-2-ynoate D (6 g, 30 mmol) was dissolved in THF (40 mL) and the solution was cooled to −78° C. under a nitrogen atmosphere. A solution of suitably substituted phenyl Grignard reagent (36 mmoL) was added dropwise maintaining an internal temperature below −65° C. The mixture was then stirred for 2 hours at −78° C. and then allowed to warm slowly to 25° C. and stirred for a further 1 hour. The reaction was quenched with saturated aqueous NH$_4$Cl solution, and extracted with EtOAc (×2). The combined organic phases were washed with brine, dried (MgSO$_4$), filtered and evaporated under vacuum to give a crude product which was purified by column chromatography using gradient elution of 0-40% EtOAc in iso-hexane to afford pure alcohol E. For example, tert-butyl 7-(3,4-dichlorophenyl)-7-hydroxyhept-2-ynoate (3.35 g, 32%) was isolated as a yellow oil. $^1$H NMR δ (ppm)(CHCl$_3$-d): 7.48-7.39 (2H, m), 7.21-7.15 (1H, m), 4.77-4.60 (1H, m), 2.35 (2H, t, J=6.98 Hz), 1.99 (1H, d, J=3.59 Hz), 1.86-1.79 (2H, m), 1.75-1.50 (2H, m), 1.49 (9H, s).

Step 5: Intermediate F

Alcohol E (9.7 mmol) was dissolved in dry Et$_2$O (150 mL) and carbon tetrabromide (6.46 g, 19 mmol) was added. The mixture was cooled in a salt-ice bath and then solid triphenylphosphine (5.11 g, 19 mmol) was added portionwise. A white precipitate formed and the reaction was stirred for 2 hours. The solid precipitate was removed by filtration and the mother liquor was evaporated to dryness under vacuum (using minimal heating). The crude residue was purified by column chromatography using gradient elution of 0-15% EtOAc in iso-hexane to afford pure bromide F. For example, tert-butyl 7-bromo-7-(3,4-dichlorophenyl)hept-2-ynoate (0.73 g, 19%) was isolated as a colourless oil. $^1$H NMR δ (ppm)(CHCl$_3$-d): 7.49 (1H, d, J=2.19 Hz), 7.43 (1H, d, J=8.31 Hz), 7.26-7.21 (1H, m), 4.86 (1H, dd, J=8.47, 6.50 Hz), 2.40-2.14 (4H, m), 1.87-1.73 (1H, m), 1.66-1.52 (1H, m), 1.49 (9H, s). LC/MS 407 (MH$^+$).

Step 6: Intermediate G

Bromide F (1.7 mmol) was dissolved in DMF (10 mL) and sodium azide (0.116 g, 1.7 mmol) was added. The mixture was heated at 40° C. overnight. The reaction mixture was concentrated under vacuum (Caution: Mixture not evaporated to complete dryness in case of any residual azide still present). The residue was dissolved in water and extracted with 9:1 EtOAc:iso-hexane (×2). The organic phases were combined, dried (MgSO$_4$), filtered and evaporated to dryness under vacuum to give a crude product which was purified by column chromatography using gradient elution of 0-50% EtOAc in iso-hexane to afford pure tetrahydro-triazolopyridine G. For example, tert-butyl 7-(3,4-dichlorophenyl)-4,5,6,7-tetrahydro-[1,2,3]triazolo[1,5-a]pyridine-3-carboxylate was isolated as a colourless oil (0.555 g, 66%). $^1$H NMR δ (ppm)(CHCl$_3$-d): 7.40 (1H, d, J=8.34 Hz), 7.03 (1H, d, J=2.22 Hz), 6.75 (1H, dd, J=8.35, 2.24 Hz), 5.74 (1H, t, J=5.34 Hz), 3.23 (1H, dt, J=18.37, 5.71 Hz), 3.11 (1H, dt, J=18.42, 7.27 Hz), 2.43-2.33 (1H, m), 2.21-2.09 (1H, m), 1.92-1.77 (2H, m), 1.64 (8H, s). LC/MS 369 (MH$^+$).

Step 7: Intermediate H

Tetrahydro-triazolopyridine G (1.7 mmol) was dissolved in DCM (20 mL) and trifluoroacetic acid (1.30 mL, 17 mmol) was added dropwise. The mixture was stirred overnight at 25° C. The solvent was removed under vacuum and the crude residue was triturated with Et$_2$O to afford triazolo carboxylic acid H as a solid which was collected by vacuum filtration. For example, 7-(3,4-dichlorophenyl)-4,5,6,7-tetrahydro-[1,2,3]triazolo[1,5-a]pyridine-3-carboxylic acid (0.45 g, 83%) was isolated as an off white solid. $^1$H NMR δ (ppm)(DMSO-d$^6$): 7.67-7.60 (1H, m), 7.49 (1H, d, J=2.12 Hz), 7.10 (1H, dd, J=8.37, 2.15 Hz), 5.82 (1H, t, J=6.20 Hz), 3.10 (2H, t, J=6.34 Hz), 2.39-2.29 (1H, m), 2.12-2.01 (1H, m), 1.80 (2H, d, J=7.16 Hz). LC/MS 313 (MH$^+$).

Step 8: Intermediate I

To a solution of triazolo carboxylic acid H (1.44 mmol) and triethylamine (0.24 mL, 1.72 mmol) in dry tert-butanol (15 mL) was added diphenylphosphoryl azide (0.38 mL, 1.72 mmol). The reaction mixture was heated at 85° C. overnight. The reaction mixture was evaporated under reduced pressure and the residue was loaded directly onto silica and purified by column chromatography using gradient elution of 0-50% EtOAc in iso-hexane to afford pure triazolo tert-butyl carbamate I. For example, tert-butyl 7-(3,4-dichlorophenyl)-4,5,6,7-tetrahydro-[1,2,3]triazolo[1,5-a]pyridin-3-ylcarbamate (0.117 g, 21%) was isolated as a colourless foam. $^1$H NMR δ (ppm)(CHCl$_3$-d): 7.44-7.37 (1H, m), 7.12 (1H, s), 6.82 (1H, dd, J=8.33, 2.21 Hz), 6.62 (1H, s), 5.58 (1H, t, J=5.86 Hz), 3.04-2.87 (2H, m), 2.43-2.33 (1H, m), 2.14-2.03 (1H, m), 1.92-1.78 (2H, m), 1.51 (9H, s). LC/MS 384 (MH$^+$).

Step 9: Intermediate J

Triazolo tert-butyl carbamate I (0.26 mmol) was dissolved in 4M HCl in dioxane (4 mL) and the mixture was stirred overnight at 25° C. The solvent was removed under vacuum and the crude residue was triturated with Et$_2$O to afford a solid which was collected by vacuum filtration. The solid was dissolved in DCM and washed with saturated aqueous NaHCO$_3$ solution. The organic phase was collected, dried (MgSO$_4$), filtered, and evaporated to dryness under vacuum to afford triazolo amine J. For example, 7-(4-chlorophenyl)-4,5,6,7-tetrahydro-[1,2,3]triazolo[1,5-a]pyridin-3-amine (0.135 g, 37%) was isolated as an off-white solid. $^1$H NMR δ (ppm)(CHCl$_3$-d): 7.31-7.26 (2H, m), 6.92-6.85 (2H, m), 5.60 (1H, t, J=5.56 Hz), 3.48 (2H, br s), 2.81-2.64 (2H, m), 2.38-2.28 (1H, m), 2.13-2.03 (1H, m), 1.90-1.79 (2H, m). LC/MS 249 (MH$^+$).

Synthesis of Intermediates-2

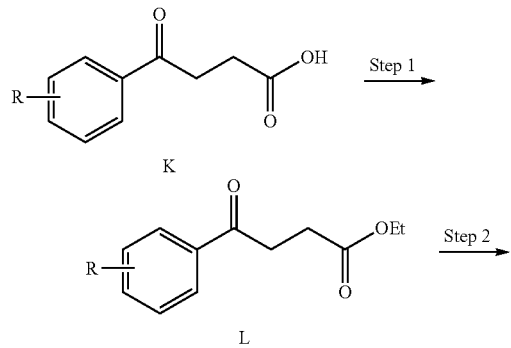

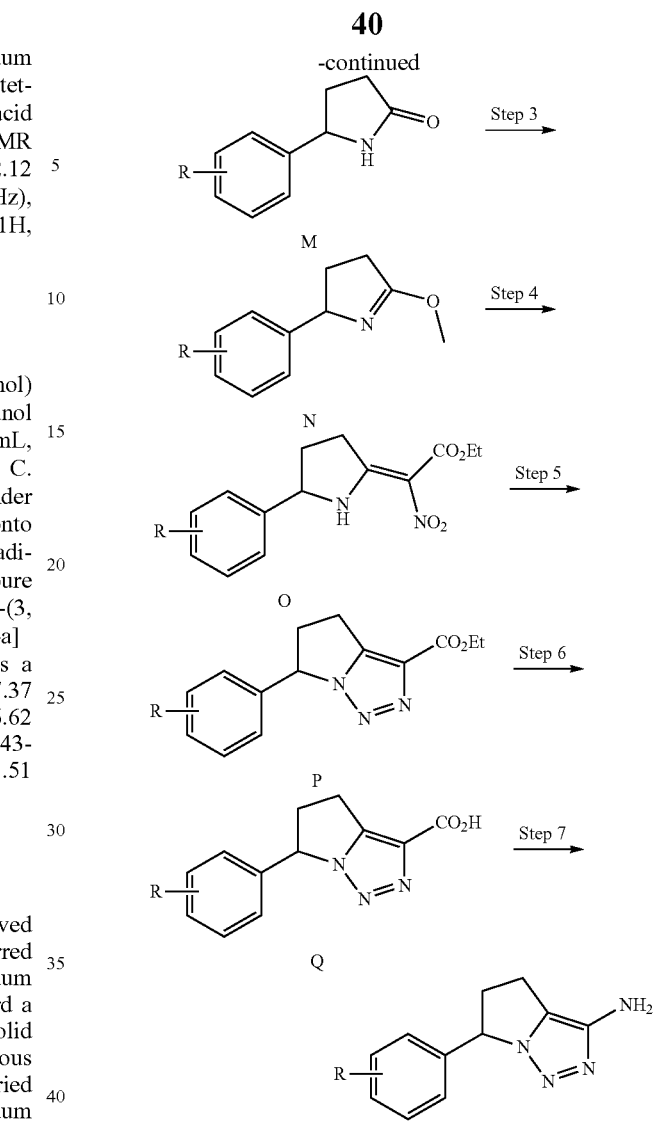

Step 1: Intermediate L

To a suitably substituted phenyl-4-oxobutanoic acid K (84.71 mmol) in DCM (180 mL) was added triethylamine (10.3 g, 0.102 mol) and cooled to 0° C. Ethyl chloroformate (12.9 g, 0.118 mol) was added dropwise, with stirring, over 15 minutes, followed by DMAP (2.1 g, 16.9 mmol), after 18 hours at 25° C. the reaction mixture was extracted with of water (3×50 mL). The organic phase was washed with brine, dried (MgSO$_4$) and concentrated down under reduced pressure to afford the phenyl 4-oxobutanoate ester L. For example, ethyl 4-(4-chlorophenyl)-4-oxobutanoate was isolated in 89% yield. $^1$H NMR δ (ppm)(CHCl$_3$-d): 7.92 (2H, d), 7.45 (2H, d), 4.18 (2H, q), 3.28 (2H, d), 2.76 (2H, d), 1.28 (3H, t). LC/MS (M+H)+241.

Step 2: Intermediate M

To phenyl 4-oxobutanoate ester L (81.9 mmol) in MeOH (450 mL) was added ammonium acetate (63.1 g, 0.819 mol). The reaction mixture was stirred at 25° C. for 1 hour. Sodium cyanoborohydride (5.14 g, 81.9 mmol) was added to the reaction and stirred at reflux. After 18 hours the reaction was cooled and then concentrated under reduced pressure. The residue was dissolved in ethyl acetate (100 mL) and washed with water (3×50 mL). The organic phase was dried (MgSO$_4$) and concentrated down under reduced pressure. The residue was purified by chromatography (silica, EtOAc/MeOH) to afford pure pyrrolidin-2-one M. For example, 5-(4-chlorophenyl)pyrrolidin-2-one was isolated in 60% yield. $^1$H NMR δ (ppm)(CHCl$_3$-d): 7.34 (2H, d), 7.25 (2H, d), 6.15 (1H, bs), 4.74 (2H, t), 2.62-2.50 (1H, m), 2.50-2.35 (2H, m), 1.98-1.89 (1H, m). LC/MS (M+H)+196.

Step 3: Intermediate N

To a stirred suspension of pyrrolidin-2-one M (51.3 mmol) and potassium carbonate (205 mmol) in dichloromethane (450 mL) was added trimethyloxonium tetrafluoroborate (102 mmol). The reaction mixture was stirred for 18 hours at 25° C. The reaction was quenched with saturated aqueous NaHCO$_3$ and extracted with ethyl acetate (3×100 mL), organic phase was washed with brine, dried (MgSO$_4$) and concentrated down under reduced pressure to afford 3,4-dihydro-2H-pyrrole N. For example, 2-(4-chlorophenyl)-5-methoxy-3,4-dihydro-2H-pyrrole in 93% yield. $^1$H NMR δ (ppm)(CHCl$_3$-d): 7.29 (2H, d), 7.22 (2H, d), 4.94 (1H, t), 3.90 (3H, s), 2.60-2.55 (3H, m), 1.84-1.79 (1H, M).

Step 4: Intermediate O 3,4-dihydro-2H-pyrrole N (23.9 mmol) was suspended in nitroethyl acetate (94 mmol) and heated at 65° C. After 7 hours the reaction was cooled and then concentrated under reduced pressure. The residue was purified by chromatography (silica, iso-hexane/EtOAc) to afford pure nitro ester O. For example, ethyl 2-(5-(4-chlorophenyl)pyrrolidin-2-ylidene)-2-nitroacetate in 46% yield. $^1$H NMR δ (ppm) (CHCl$_3$-d): 9.82 (0.4H, bs), 9.53 (0.6H, bs), 7.37 (2H, d), 7.21 (2H, d), 5.09-5.02 (1H, m), 4.36-4.27 (2H, m), 3.46-3.16 (2H, m), 2.64-2.58 (1H, m), 2.04-1.31 (1H, m), 1.35 (3H, m)—Product is a 1:1 mixture of E and Z isomers.

Step 5: Intermediate P

To nitro ester O (16 mmol) in acetic acid (50 mL) at 5° C. was added zinc dust (98 mmol) and stirred at 25° C. for 1 hour, the reaction was filtered and the combined filtrates stirred and cooled to 5° C., treated with TFA (57 mmol) followed by t-butyl nitrite (53 mmol), allowed to warm to 25° C. and stirred for 2 hours. The mixture was treated with water (50 ml) and concentrated down under reduced pressure. The residue was purified by chromatography (silica, EtOAc/MeOH) to afford pure dihydro-4H-pyrrolo-triazole P. For example, ethyl 6-(4-chlorophenyl)-5,6-dihydro-4H-pyrrolo[1,2-c][1,2,3]triazole-3-carboxylate in 55% yield. $^1$H NMR δ (ppm)(CHCl$_3$-d): 7.32 (2H, d), 7.08 (2H, d), 5.68 (1H, q), 4.39 (2H, q), 3.38-3.12 (3H, m), 2.78-2.70 (1H, m), 1.41 (3H, t).

Step 6: Intermediate Q

To a dihydro-4H-pyrrolo-triazole P (3.6 mmol) in dioxane (15 mL) and MeOH (5 ml) was added lithium hydroxide (4.6 mmol) in water (5 mL) and stirred at 25° C. for 18 hours, the reaction was concentrated down under reduced pressure. The residue was dissolved in water (20 mL) and adjusted to pH 7 with aq HCl and filtered to afford the triazolo carboxylic acid Q. For example, 6-(2-chlorophenyl)-5,6-dihydro-4H-pyrrolo[1,2-c][1,2,3]triazole-3-carboxylic acid was isolated as an off-white solid in 73% yield. $^1$H NMR δ (ppm)(DMSOd$_6$): 13.20 (1H, bs), 7.58 (1H, d), 7.45-7.01 (2H, m), 6.98-6.91 (1H, m), 6.20-6.11 (1H, m), 3.40-3.30 (1H, m), 3.20-3.09 (2H, m), 2.70-2.58 (1H, m).

Step 7: Intermediate R

Triazolo carboxylic acid Q was converted into triazolo amine R using the protocols previously described for the conversion of triazolo carboxylic acid H into triazolo amine J. For example, 6-(4-fluorophenyl)-5,6-dihydro-4H-pyrrolo[1,2-c][1,2,3]triazol-3-amine was isolated as colourless oil in 50% yield. $^1$H NMR δ (ppm)(CHCl$_3$-d): 7.15-6.98 (4H, m), 5.51-5.47 (1H, q), 3.97 (2H, bs), 3.19-3.10 (1H, m), 2.90-2.77 (2H, m), 2.61-2.50 (1H, m).

Synthesis of Intermediates-3

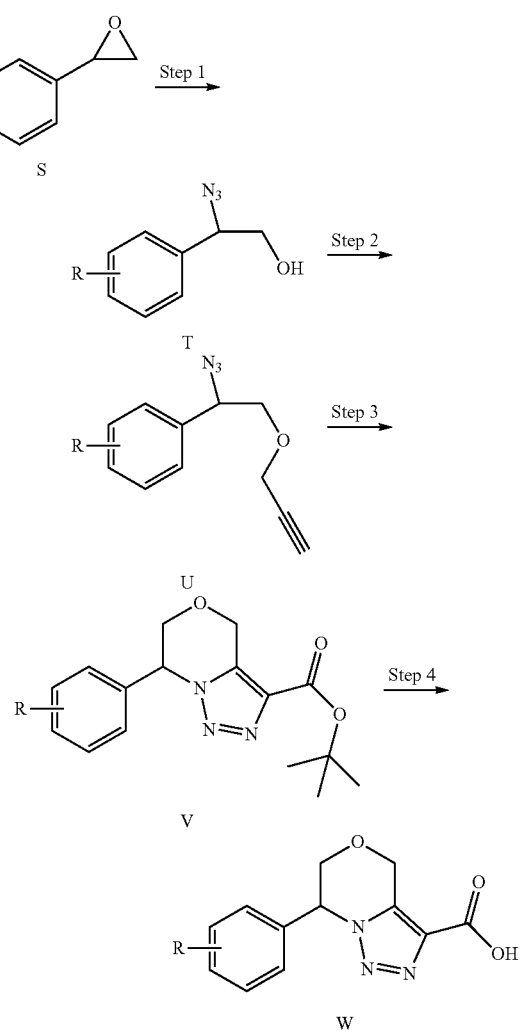

Step 1: Intermediate T

To an appropriately substituted phenyloxirane S (22.64 mmol) in distilled water (120 mL) was added sodium azide (4.41 g, 68.1 mmol). The reaction mixture was heated for 5 hours at 70° C. and after cooling to 25° C. was diluted with water (20 mL) and DCM (150 mL). The organic phase was separated, dried with magnesium sulfate and evaporated to dryness to yield a crude product that was purified by flash column chromatography (60-120 mesh silica gel; eluent: 20% EtOAc in pet ether), affording Intermediate T. For example, using 4-chlorophenyloxirane, 2-azido-2-(4-chlorophenyl)ethanol was obtained as a white powder (4.2 g, 94%). $^1$H NMR (CDCl$_3$, 300 MHz) δ 7.40 (d, J=7 Hz, 2H), 7.30 (d, J=7 Hz, 2H), 4.71 (dd, J=7, 3 Hz, 1H), 3.78-3.73 (m, 2H), 1.90 (t, J=7.5 Hz, 1H). HPLC (Method H) Rt 3.48 min (Purity: 99.9%).

Step 2: Intermediate U

To an ice-cooled suspension of sodium hydride (57-63% oil dispersion, 447 mg, 11.2 mmol in anhydrous THF (10 mL) was added dropwise a THF solution (10 mL) of an appropriately substituted azido alcohol T (8.6 mmol). The reaction mixture was stirred at 0° C. for 30 minutes before introducing a THF solution (5 mL) of 18-crown-6 ether (2.95 g, 11.2 mmol) and 3-bromo-propyne (2.05 g, 17.2 mmol). The reaction mixture was stirred for 30 minutes at 0° C. and slowly warmed to 25° C. for 18 hours. The reaction mixture was quenched with water and extracted with EtOAc. The organic phase was dried with magnesium sulfate and evaporated to dryness to yield a crude that was purified by flash column chromatography (60-120 mesh silica gel; eluent: 5% EtOAc in petroleum ether), affording Intermediate U. For example, 1-(1-azido-2-(prop-2-ynyloxy)ethyl)-4-chlorobenzene was obtained as a white oil (2.1 g, 98%). $^1$H NMR (CDCl$_3$, 400 MHz) δ 7.40-7.37 (m, 2H), 7.35-7.30 (m, 2H), 4.76-4.72 (m, 1H), 4.26-4.24 (m, 2H), 3.76-3.71 (m, 2H), 2.49 (t, J=7 Hz, 1H). HPLC (Method H) Rt 4.76 min (Purity: 96.2%).

Step 3: Intermediate V

To a solution in dry THF (150 mL) at −70° C. under nitrogen was added a suitably substituted azido alkyne U (9.34 mmol) followed by n-butyl lithium (2.5 M, 4.1 mL, 10.3 mmol). The reaction mixture was stirred for 30 minutes at this temperature before adding dropwise a THF solution (15 mL) of BOC anhydride (3.05 g, 14 mmol). The reaction mixture was allowed to warm to 25° C. overnight and then quenched into an ice-water solution (100 mL) followed by extraction of the resulting mixture with Et$_2$O (2×50 mL). The extracts were combined, washed with brine and dried over anhydrous sodium sulfate. After removal of the solvents, the crude product was purified by flash column chromatography (60-120 mesh silica gel; eluent: 50% EtOAc in pet ether), affording Intermediate V. For example, tert-butyl 7-(4-chlorophenyl)-6,7-dihydro-4H-[1,2,3]triazolo[5,1-c][1,4]oxazine-3-carboxylate was obtained as a white oil (0.37 g, 12%). $^1$H NMR (CDCl$_3$, 300 MHz) δ 7.34 (d, J=7.5 Hz, 2H), 7.08 (d, J=7.5 Hz, 2H), 5.64 (t, J=7.5 Hz, 1H), 5.26 (d, J=12 Hz, 1H), 5.12 (d, J=12 Hz, 1H), 4.26 (dd, T=7, 2 Hz, 1H), 4.10 (dd, J=7, 2 Hz, 1H), 1.63 (s, 9H). LC/MS 336.2 (M+H)$^+$. HPLC (Method H) Rt 4.44 min (Purity: 95.9%).

Step 4: Intermediate W

HCl/dioxane (4 M, 10 mL) was added to an appropriately substituted tert-butyl ester (1.10 mmol) and the reaction was left to stir for 12 hours at room temperature. Upon completion of the reaction, the organic solvent was removed under vacuum and the residue was dissolved in a mixture of DCM (20 mL) and saturated sodium hydrogenon carbonate (10 mL). The organic phase was separated, dried with magnesium sulfate and evaporated to dryness to yield Intermediate W as crude product. For example 7-(4-chlorophenyl)-6,7-dihydro-4H [1,2,3]triazolo[5,1-c][1,4]oxazine-3-carboxylic acid was obtained as a brown oil (220 mg, 71%) that was pure enough to use without further purification. $^1$H NMR (CDCl$_3$, 300 MHz) δ 7.34 (d, J=7 Hz, 2H), 7.20 (d, J=7 Hz, 2H), 5.50 (t, J=7.5 Hz, 1H), 5.30-5.20 (m, 2H), 4.20-4.10 (m, 2H). LC/MS 280.1 (M+H)$^+$. HPLC (Method H) Rt (2.97 min (Purity: 94.2%).

Synthesis of Intermediates-4

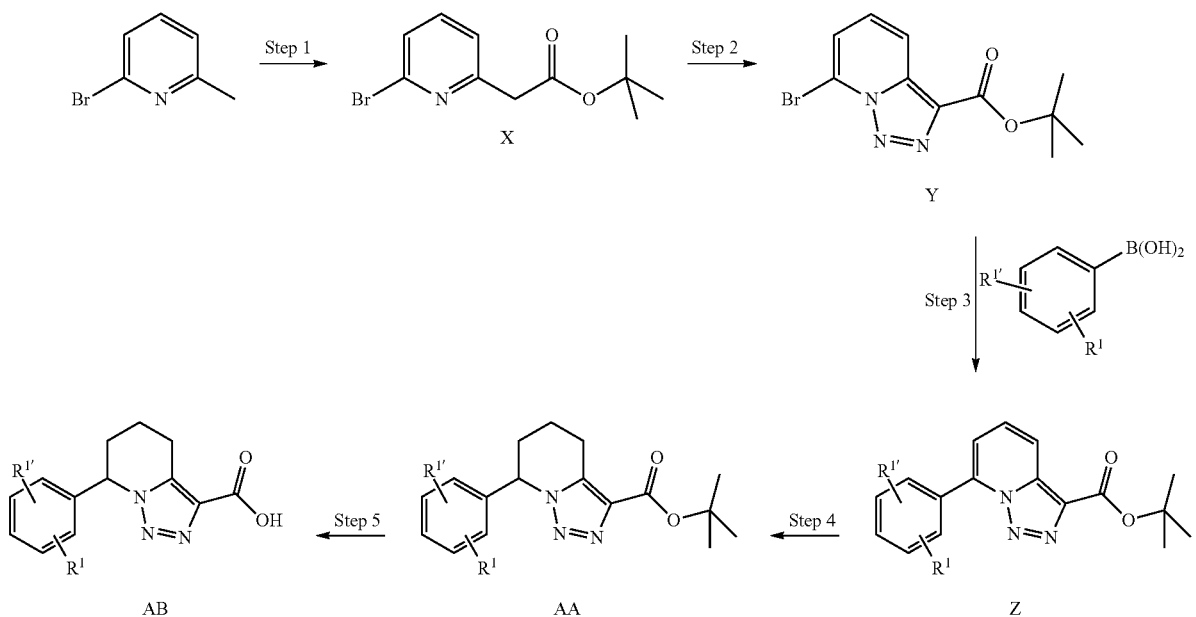

Step 1: (6-Bromo-pyridin-2-yl)-acetic acid tert-butyl ester (X)

Diisopropylamine (19.6 mL, 0.14 mol) was dissolved in THF (200 mL) and cooled down to −70° C. where a commercial solution of n-Butyl lithium was added dropwise (79 mL, 1.6 M in Hexane, 0.13 mol). After 20 minutes, the mixture was gradually warmed to −10° C. and then again cooled at −70° C. To this solution, 2-Bromo-6-methyl pyridine (20 g, 0.11 mol) in THF (100 mL) was added and the resulting mixture stirred for 30 minutes at this temperature. Boc anhydride (27.7 g, 0.13 mol) in THF (50 mL) was added and the reaction left for 2 hours at −70° C. and then slowly warmed to room temperature over a period of 4 hours. The reaction mixture was quenched with water and extracted with EtOAc (3×200 mL). The combined organic layer was washed with water, brine and dried over sodium sulphate. The organic solvent was removed under reduced pressure and the crude material purified by flash column chromatography using silica gel (60-120 mesh silica gel; eluent: 10% EtOAc in pet ether) as eluent to afford the titled compound (15 g, 48%) as a pale yellow liquid. $^1$H NMR (DMSO-d6, 400 MHz) δ 7.73-7.69 (t, J=7.7 Hz, 1H), 7.54-7.52 (d, J=7.8 Hz, 1H), 7.38-7.36 (d, J=7.5 Hz, 1H), 3.73 (s, 2H), 1.44 (s, 9H).

Step 2: 7-Bromo-[1,2,3]triazolo[1,5-a]pyridine-3-carboxylic acid tert-butyl ester (Y)

To a solution of (6-bromo-pyridin-2-yl)-acetic acid tert-butyl ester (40 g, 0.15 mol) in MeCN (10 mL) was added DBU (78.5 g, 0.52 mol) at 0° C. under N2 atmosphere. To this cold solution, 4-acetamido benzenesulfonylazide (52.9 g, 0.22 mol) was added portion-wise. The reaction mixture was stirred at 0° C. for 2 hours and slowly warmed to room temperature over a period of 2 hours. The reaction mixture was quenched with water (10 mL) and extracted with EtOAc (3×300 mL). The combined organic layer was washed with water, brine and dried over sodium sulphate. Organic solvent was removed under reduced pressure and the crude material purified by flash column chromatography using silica gel (60-120 mesh silica gel; eluent: 10% EtOAc in pet ether) to afford the titled compound (15 g, 34%) as a white solid. $^1$H NMR (DMSO-d6, 400 MHz) δ 8.17-8.15 (d, J=8.6 Hz, 1H), 7.76-7.74 (d, J=7.1 Hz, 1H), 7.67-7.63 (m, 1H), 1.60 (s, 9H. LC/MS (Method A): 298.2 (M+H)$^+$. HPLC (Method A) Rt 4.06 min (Purity: 98.1%).

Step 3: Intermediate Z

7-Bromo-[1,2,3]triazolo[1,5-a]pyridine-3-carboxylic acid tert-butyl ester (4.5 g, 0.015 mol) and suitably substituted phenylboronic acid (0.017 mol) were dissolved in a mixture of dioxane and water (80 mL:20 mL). Sodium carbonate (1.6 g, 0.020 mol) and bis(triphenylphospine)palladium (II) chloride (0.53 g, 0.7 mmol) were added under inert atmosphere and the reaction mixture heated at 80° C. for 5 hours. Upon completion of the reaction, the reaction mixture was cooled down to room temperature and filtered through a Celite pad. The filtrate was concentrated under reduced pressure and the resulting residue diluted with EtOAc (200 mL) and washed with water (2×100 mL), brine and dried over sodium sulphate. Organic solvent was removed under reduced pressure and the crude material purified by flash column chromatography using silica gel (60-120 mesh silica gel; eluent: 20% EtOAc in pet ether) to afford Intermediate Z. For example, tert-Butyl 7-(4-fluorophenyl)[1,2,3]triazolo[1,5-a]pyridine-3-carboxylate was obtained as a white solid (3 g, 61%). $^1$H NMR (DMSO-d$_6$, 400 MHz) δ 8.17-8.15 (d, J=8.6 Hz, 1H), 7.76-7.74 (d, J=7.1 Hz, 1H), 7.67-7.63 (m, 1H), 1.60 (s, 9H. LC/MS (Method A): 298.2 (M+H)$^+$. HPLC (Method A) Rt 4.06 min (Purity: 98.1%).

Alternatively, tert-Butyl 7-[3-(trifluoromethyl)phenyl][1,2,3]triazolo[1,5-a]pyridine-3-carboxylate was obtained as a white solid (66%). $^1$H NMR (DMSO-d$_6$, 400 MHz) δ 8.38 (s, 1H), 8.30-8.28 (d, J=7.8 Hz, 1H), 8.22-8.20 (dd, J=1.0 Hz, 8.8 Hz, 1H), 7.98-7.96 (d, J=7.9 Hz, 1H), 7.88-7.82 (m, 1H), 7.62-7.60 (m, 1H), 1.62 (s, 9H).

Step 4: Intermediate AA

To a solution of Intermediate Z (9.2 mmol) in EtOAc (70 mL) was added acetic acid (19.4 g, 0.139 mol) and Pd/C (3 g, 10% w/w). This mixture was hydrogenated under a pressure of 30 Kg/cm$^2$ for 48 h. The solution was passed through a celite pad and the filtrate concentrated under reduced pressure. The crude material was purified by flash column chromatography using silica gel (60-120 mesh silica gel; eluent: 20% EtOAc in pet ether) to afford Intermediate AA. For example, tert-Butyl 7-(4-fluorophenyl)-4,5,6,7-tetrahydro[1,2,3]triazolo[1,5-a]pyridine-3-carboxylate was obtained as a white solid (1.5 g, 51%). $^1$H NMR (CDCl$_3$, 400 MHz) δ 7.04-7.0 (m, 2H), 6.90-6.86 (m, 2H), 5.81-5.78 (t, 1H), 3.26-3.20 (m, 1H), 3.14-3.05 (m, 1H), 2.40-2.33 (m, 1H), 2.18-2.13 (m, 1H), 1.89-1.86 (m, 2H), 1.56 (s, 9H).

Alternatively, tert-Butyl 7-[3-(trifluoromethyl)phenyl]-4,5,6,7-tetrahydro[1,2,3]triazolo[1,5-a]pyridine-3-carboxylate was obtained as a white solid (82%). $^1$H NMR (DMSO-d$_6$, 400 MHz) δ 7.71-7.61 (d, J=7.8 HZ, 1H), 7.61-7.57 (m, 2H), 7.36-7.34 (d, J=7.8 Hz, 1H), 5.90-5.87 (m, 1H), 3.11-3.08 (m, 2H), 2.34-2.32 (m, 1H), 2.10-2.06 (m, 1H), 1.85-1.77 (m, 2H), 1.54 (s, 9H).

Step 5: Intermediate AB

Intermediate AA (0.005 mol) was dissolved in dioxane (20 mL). A commercial solution of HCl in dioxane (4 M, 20 mL) was added slowly and the reaction mixture stirred at room temperature for 12 hours. Upon completion of the reaction (TLC: CHCl$_3$: MeOH (9:1), R$_f$-0.7), the organic solvent was evaporated under reduced pressure. The crude material was slurred with diethyl ether and filtered to afford Intermediate AB. For example, 7-(4-fluorophenyl)-4,5,6,7-tetrahydr[1,2,3]triazolo[1,5-a]pyridine-3-carboxylic acid was obtained as an off white solid (1.0 g, 82%). $^1$H NMR (CDCl$_3$, 400 MHz) δ 12.9 (s, 1H), 7.21-7.11 (m, 4H), 5.82-5.79 (t, J=11.9 Hz, 1H), 3.10-3.07 (m, 2H), 2.30-2.23 (m, 1H), 2.05-2.0 (m, 1H), 1.80-1.75 (m, 2H). LC/MS (Method A): 263.2 (M+H)$^+$. HPLC (Method A) Rt 3.20 min (Purity: 99.4%).

Alternatively, 7-[3-(trifluoromethyl)phenyl]-4,5,6,7-tetrahydro[1,2,3]triazolo[1,5-a]pyridine-3-carboxylic acid was obtained as a white solid (62%). $^1$H NMR (DMSO-d$_6$, 400 MHz) δ 7.71-7.69 (d, J=7.8 Hz, 1H), 7.62-7.58 (m, 2H), 7.37-7.35 (d, J=7.9 Hz, 1H), 5.92-5.88 (t, J=6.7 Hz, 1H), 3.12-3.09 (m, 2H), 2.38-2.33 (m, 1H), 2.11-2.06 (m, 1H), 1.82-1.78 (m, 2H). LC/MS (Method A): 313.1 (M+H)$^+$. HPLC (Method A) Rt 3.90 min (Purity: 99.3%).

General Methods

General Method A:

A carousel tube was charged with a suitably substituted aryl halide (0.247 mmol), a suitably substituted triazolo amine J (0.247 mmol), Pd$_2$dba$_3$ (11 mg, 0.012 mmol), Xantphos (21 mg, 0.037 mmol) and Cs$_2$CO$_3$ (80 mg, 0.247 mmol). Dioxane (3 mL) was added and nitrogen was bubbled through the mixture for 5 minutes. The carousel tube was sealed and the reaction was stirred at 110° C. overnight. The reaction mixture was allowed to cool to 25° C. and then partitioned between DCM (30 mL) and water (25 mL). The organic phase was collected and the aqueous phase was extracted with DCM (2×30 mL). The combined organic extracts were dried (MgSO$_4$), filtered, and evaporated to dryness under vacuum. The crude residue was dissolved in DMSO and purified by preparative HPLC.

The following compounds were prepared from intermediate J

| Ex | Structure | Rt | MS | NMR |
|---|---|---|---|---|
| 1 | 7-(2-chloro-4-fluorophenyl)-N-(3-methoxy-4-(4-methyl-1H-imidazol-1-yl)phenyl)-4,5,6,7-tetrahydro-[1,2,3]triazolo[1,5-a]pyridin-3-amine<br>Off-white solid | 9.93$^c$ | 453 | $^1$H NMR δ (ppm)(CHCl$_3$-d): 7.65 (1 H, d, J = 1.36 Hz), 7.20 (1 H, dd, J = 8.27, 2.60 Hz), 7.07 (1 H, d, J = 8.45 Hz), 6.93 (1 H, td, J = 8.25, 2.63 Hz), 6.82 (1 H, s), 6.67 (1 H, d, J = 2.36 Hz), 6.51 (1 H, dd, J = 8.72, 5.74 Hz), 6.39 (1 H, dd, J = 8.45, 2.38 Hz), 6.06 (1 H, t, J = 5.68 Hz), 3.77 (3 H, s), 2.88-2.70 (2 H, m), 2.47-2.35 (1 H, m), 2.45-2.04 (4 H, m), 1.93-1.85 (2 H, m). NH not observed |
| 2 | N-(3-methoxy-4-(4-methyl-1H-imidazol-1-yl)phenyl)-7-(2-(trifluoromethyl)phenyl)-4,5,6,7-tetrahydro-[1,2,3]triazolo[1,5-a]pyridin-3-amine<br>Off-white solid | 3.81$^a$ | 469 | $^1$H NMR δ (ppm)(CHCl$_3$-d): 7.76 (1 H, d, J = 7.74 Hz), 7.56 (1 H, d, J = 1.31 Hz), 7.53-7.40 (2 H, m), 7.07 (1 H, d, J = 8.43 Hz), 6.84-6.78 (2 H, m), 6.70 (1 H, d, J = 2.37 Hz), 6.37 (1 H, dd, J = 8.44, 2.38 Hz), 6.03 (1 H, t, J = 6.47 Hz), 5.97 (1 H, s), 3.76 (3 H, s), 2.88-2.78 (2 H, m), 2.56-2.47 (1 H, m), 2.29 (3 H, s), 2.12-1.99 (2 H, m), 1.94-1.82 (1 H, m). |
| 3 | 7-(2-chloro-4-fluorophenyl)-N-(3-fluoro-4-(4-methyl-1H-imidazol-1-yl)phenyl)-4,5,6,7-tetrahydro-[1,2,3]triazolo[1,5-a]pyridin-3-amine<br>Off-white solid | 3.59$^a$ | 441 | $^1$H NMR δ (ppm)(CHCl$_3$-d): 7.59 (1 H, s), 7.24-7.14 (2 H, m), 6.94 (1 H, td, J = 8.25, 2.61 Hz), 6.87 (1 H, s), 6.74-6.64 (2 H, m), 6.50 (1 H, dd, J = 8.72, 5.74 Hz), 6.12-6.01 (2 H, m), 2.87-2.68 (2 H, m), 2.47-2.36 (1 H, m), 2.35-2.13 (4 H, m), 1.92-1.85 (2 H, m). |

| Ex | Structure | Rt | MS | NMR |
|---|---|---|---|---|
| 4 | 7-(4-chlorophenyl)-N-(3-methoxy-4-(4-methyl-1H-imidazol-1-yl)phenyl)-4,5,6,7-tetrahydro-[1,2,3]triazolo[1,5-a]pyridin-3-amine<br>Beige solid | 2.73[b] | 435 | ¹H NMR δ (ppm)(DMSO-d₆): 8.24 (1 H, s), 7.57 (1 H, d, J = 1.33 Hz), 7.45 (2 H, d, J = 8.34 Hz), 7.14-7.08 (3 H, m), 6.96 (1 H, s), 6.89 (1 H, d, J = 2.30 Hz), 6.66 (1 H, dd, J = 8.53, 2.29 Hz), 5.77 (1 H, t, J = 5.91 Hz), 3.74 (3 H, s), 2.80-2.70 (2 H, m), 2.39-2.31 (1 H, m), 2.13 (3 H, s), 2.11-2.01 (1 H, m), 1.78 (2 H, s). |
| 5 | 7-(3,4-dichlorophenyl)-N-(3-methoxy-4-(4-methyl-1H-imidazol-1-yl)phenyl)-4,5,6,7-tetrahydro-[1,2,3]triazolo[1,5-a]pyridin-3-amine<br>Pale yellow solid | 3.33[a] | 469 | ¹H NMR δ (ppm)(CHCl₃-d): 7.56 (1 H, d, J = 1.32 Hz), 7.47-7.40 (1 H, m), 7.10-7.06 (2 H, m), 6.87 (1 H, dd, J = 8.32, 2.20 Hz), 6.82 (1 H, s), 6.67 (1 H, d, J = 2.38 Hz), 6.38 (1 H, dd, J = 8.44, 2.39 Hz), 5.75 (1 H, s), 5.67 (1 H, t, J = 5.69 Hz), 3.78 (3 H, s), 2.86-2.70 (2 H, m), 2.48-2.38 (1 H, m), 2.29 (3 H, s), 2.21-2.11 (1 H, m), 1.93-1.86 (2 H, m) |
| 6 | N-(3-methoxy-4-(4-methyl-1H-imidazol-1-yl)phenyl)-7-(3-(trifluoromethyl)phenyl)-4,5,6,7-tetrahydro-[1,2,3]triazolo[1,5-a]pyridin-3-amine<br>Brown solid | 9.93[c] | 469 | ¹H NMR (400 MHz, CHCl₃-d): δ 7.60 (d, J = 7.92 Hz, 1 H); 7.56 (d, J = 1.32 Hz, 1 H); 7.50 (t, J = 7.81 Hz, 1 H); 7.18 (d, J = 7.83 Hz, 1 H); 7.08 (d, J = 8.42 Hz, 1 H); 6.82 (s, 1 H); 6.67 (d, J = 2.37 Hz, 1 H); 6.39 (dd, J = 8.43, 2.39 Hz, 1 H); 5.81-5.75 (m, 2 H); 3.77 (s, 3 H); 2.88-2.71 (m, 2 H); 2.52-2.42 (m, 1 H); 2.29 (d, J = 0.98 Hz, 3 H); 2.24-2.13 (m, 1 H); 1.94-1.86 (m, 2 H). |

| Ex | Structure | Rt | MS | NMR |
|---|---|---|---|---|
| 7 | 7-(4-fluorophenyl)-N-(3-methoxy-4-(4-methyl-1H-imidazol-1-yl)phenyl)-4,5,6,7-tetrahydro-[1,2,3]triazolo[1,5-a]pyridin-3-amine<br>White solid | 2.63[b] | 419 | $^1$H NMR (400 MHz, DMSO-d$^6$): δ 8.25-8.20 (m, 1 H); 7.57 (d, J = 1.33 Hz, 1 H); 7.26-7.06 (m, 5 H); 6.96 (s, 1 H); 6.89 (d, J = 2.33 Hz, 1 H); 6.65 (dd, J = 8.53, 2.33 Hz, 1 H); 5.75 (t, J = 5.94 Hz, 1 H); 3.74 (s, 3 H); 2.83-2.69 (m, 2 H); 2.39-2.28 (m, 1 H); 2.13 (s, 3 H); 2.12-2.00 (m, 1 H); 1.82-1.75 (m, 2 H). |

General Method B:

A carousel tube was charged with a suitably substituted aryl halide (0.247 mmol), a suitably substituted triazolo amine J (0.247 mmol), Pd$_2$dba$_3$ (11 mg, 0.012 mmol), Xantphos (21 mg, 0.037 mmol) and Cs$_2$CO$_3$ (80 mg, 0.247 mmol). Dioxane (3 mL) was added and nitrogen was bubbled through the mixture for 5 minutes. The carousel tube was sealed and the reaction was stirred at 70° C. overnight. The reaction mixture was allowed to cool to 25° C. and then partitioned between DCM (30 mL) and water (25 mL). The organic phase was collected and the aqueous phase was extracted with DCM (2×30 mL). The combined organic extracts were dried (MgSO$_4$), filtered, and evaporated to dryness under vacuum. The crude residue was dissolved in DMSO and purified by preparative HPLC.

The following compounds were prepared from intermediate R

| Ex | Structure | Rt | MS | NMR |
|---|---|---|---|---|
| 8 | 6-(4-chlorophenyl)-N-(3-methoxy-4-(4-methyl-1H-imidazol-1-yl)phenyl)-5,6-dihydro-4H-pyrrolo[1,2-c][1,2,3]triazol-3-amine<br>Pale yellow solid | 3.62[a] | 421 | $^1$H NMR δ (ppm)(CHCl$_3$-d): 7.65 (1 H, d, J = 1.34 Hz), 7.40-7.35 (2 H, m), 7.16-7.07 (3 H, m), 6.83 (1 H, s), 6.65 (1 H, d, J = 2.38 Hz), 6.45 (1 H, dd, J = 8.45, 2.37 Hz), 6.06 (1 H, s), 5.65 (1 H, dd, J = 8.14, 5.63 Hz), 3.80 (3 H, s), 3.31-3.24 (1 H, m), 2.99-2.91 (2 H, m), 2.76-2.71 (1 H, m), 2.30 (3 H, s). |
| 9 | 6-(4-chlorophenyl)-N-(4-(2-methylpyridin-4-yl)phenyl)-5,6-dihydro-4H-pyrrolo[1,2-c][1,2,3]triazol-3-amine<br>Brown solid | 9.98[c] | 402 | $^1$H NMR δ (ppm)(CHCl$_3$-d): 8.49 (1 H, d, J = 5.30 Hz), 7.61-7.53 (2 H, m), 7.42-7.33 (2 H, m), 7.34 (1 H, s), 7.29 (1 H, dd, J = 5.42, 1.82 Hz), 7.14 (2 H, d, J = 8.31 Hz), 7.00-6.92 (2 H, m), 6.13 (1 H, s), 5.65 (1 H, dd, J = 8.16, 5.59 Hz), 3.32-3.23 (1 H, m), 2.99-2.90 (2 H, m), 2.76-2.67 (1 H, m), 2.63-2.59 (3 H, m). |

| Ex | Structure | Rt | MS | NMR |
|---|---|---|---|---|
| 10 | 6-(4-fluorophenyl)-N-(3-methoxy-4-(4-methyl-1H-imidazol-1-yl)phenyl)-5,6-dihydro-4H-pyrrolo[1,2-c][1,2,3]triazol-3-amine<br>Off white solid | 3.39<sup>a</sup> | 405 | ¹H NMR δ (ppm)(CDCl₃): 7.57 (1H, s), 7.26-7.16 (2H, m), 7.11-7.06 (3H, m), 6.82 (1H, s), 6.78 (1H, d), 6.52 (1H, s), 6.45 (1H, dd), 5.65 (1H, q), 3.77 (3H, s), 3.29-3.22 (1H, m), 2.99-2.93 (2H, m), 2.78-2.71 (1H, m), 2.29 (3H, s) |
| 11 | 6-(2-chlorophenyl)-N-(3-methoxy-4-(4-methyl-1H-imidazol-1-yl)phenyl)-5,6-dihydro-4H-pyrrolo[1,2-c][1,2,3]triazol-3-amine<br>Brown gum | 2.67<sup>b</sup> | 421 | ¹H NMR δ (ppm)(CDCl₃): 7.57 (1H, s), 7.47 (1H, d), 7.32-7.22 (2H, m), 7.11 (1H, d), 6.83 (1H, s), 6.70 (2H, m), 6.47 (1H, d), 6.14 (1H, s), 6.06 (1H, q), 3.77 (3H, s), 3.41-3.34 (1H, m), 2.94-2.91 (2H, m), 2.74-2.70 (1H, m), 2.30 (3H, s) |

General Method C:

To a suitably substituted triazolo carboxylic acid H (0.224 mmol) in DMF (1 mL) was added a suitably substituted aniline (0.224 mmol), HATU (O-(7-Azabenzotriazol-1-yl)-N,N,N',N'-tetramethyluronium hexafluorophosphate) (0.246 mmol) followed by diisopropylethylamine (0.673 mmol) and stirred at 25° C. for 18 hours. The reaction mixture was purified directly by preparative HPLC to afford pure amide.

The following compounds were prepared from intermediate H

| Ex | Structure | Rt | MS | NMR |
|---|---|---|---|---|
| 12 | 7-(4-chlorophenyl)-N-(3-methoxy-4-(4-methyl-1H-imidazol-1-yl)phenyl)-4,5,6,7-tetrahydro-[1,2,3]triazolo[1,5-a]pyridine-3-carboxamide<br>Off white solid | 10.27<sup>c</sup> | 463 | ¹H NMR δ (ppm)(CHCl₃-d): 9.07 (1 H, s), 7.75 (1 H, s), 7.66 (1 H, s), 7.35 (2 H, d, J = 8.12 Hz), 7.23 (1 H, d, J = 8.47 Hz), 7.15 (1 H, dd, J = 8.49, 2.17 Hz), 6.94-6.87 (3 H, m), 5.76 (1 H, t, J = 5.49 Hz), 3.90 (3 H, s), 3.42-3.22 (2 H, m), 2.48-2.38 (1 H, m), 2.30 (3 H, s), 2.23-2.13 (1 H, m), 1.92 (2 H, t, J = 6.35 Hz). |

-continued

| Ex | Structure | Rt | MS | NMR |
|----|-----------|-----|-----|------|
| 13 | 7-(4-chlorophenyl)-N-(3-cyano-4-(4-methyl-1H-imidazol-1-yl)phenyl)-4,5,6,7-tetrahydro-[1,2,3]triazolo[1,5-a]pyridine-3-carboxamide<br>Yellow solid | 2.97[b] | 458 | $^1$H NMR δ (ppm)(CHCl$_3$-d): 9.18 (1 H, s), 8.36 (1 H, d, J = 2.49 Hz), 7.90 (1 H, dd, J = 8.77, 2.52 Hz), 7.73 (1 H, d, J = 1.54 Hz), 7.44-7.31 (3 H, m), 7.05 (1 H, s), 6.93 (2 H, d, J = 8.15 Hz), 5.76 (1 H, t, J = 5.55 Hz), 3.40-3.22 (2 H, m), 2.49-2.39 (1 H, m), 2.32 (3 H, s), 2.23-2.14 (1 H, m), 1.94 (2 H, d, J = 7.30 Hz). |
| 14 | 7-(4-chlorophenyl)-N-(3-fluoro-4-(4-methyl-1H-imidazol-1-yl)phenyl)-4,5,6,7-tetrahydro-[1,2,3]triazolo[1,5-a]pyridine-3-carboxamide<br>Yellow solid | 2.87[b] | 451 | $^1$H NMR δ (ppm)(CHCl$_3$-d): 9.09 (1 H, s), 7.93 (1 H, dd, J = 12.62, 2.25 Hz), 7.70 (1 H, s), 7.42-7.30 (4 H, m), 6.93 (3 H, t, J = 9.60 Hz), 5.76 (1 H, t, J = 5.54 Hz), 3.40-3.21 (2 H, m), 2.49-2.39 (1 H, m), 2.31 (3 H, s), 2.22-2.13 (1 H, m), 1.92 (2 H, t, J = 6.30 Hz). |
| 15 | 7-(4-chlorophenyl)-N-(6-methoxy-5-(4-methyl-1H-imidazol-1-yl)pyridin-2-yl)-4,5,6,7-tetrahydro-[1,2,3]triazolo[1,5-a]pyridine-3-carboxamide<br>Off-white solid | 10.14[e] | 464 | $^1$H NMR δ (ppm)(CHCl$_3$-d): 9.47 (1 H, s), 7.97 (1 H, d, J = 8.26 Hz), 7.70 (1 H, d, J = 1.49 Hz), 7.58 (1 H, d, J = 8.27 Hz), 7.38-7.31 (2 H, m), 6.91 (3 H, d, J = 8.93 Hz), 5.79 (1 H, t, J = 5.38 Hz), 3.97 (3 H, s), 3.37 (1 H, dt, J = 18.43, 5.82 Hz), 3.26 (1 H, dt, J = 18.43, 7.06 Hz), 2.49-2.38 (1 H, m), 2.30 (3 H, s), 2.24-2.14 (1 H, m), 1.96-1.88 (2 H, m). |

| Ex | Structure | Rt | MS | NMR |
|---|---|---|---|---|
| 16 | 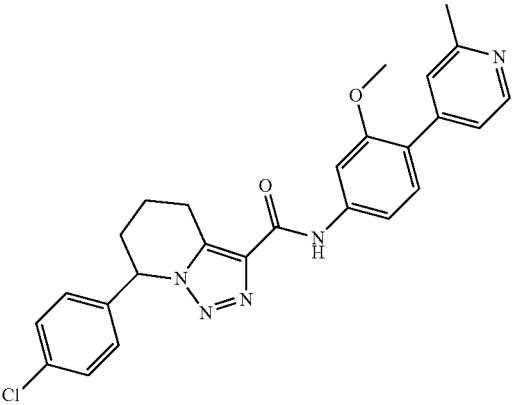 [SMILES: COc1cc(NC(=O)c2nnn3c2CCCC3c2ccc(Cl)cc2)ccc1-c1ccnc(C)c1]<br>7-(4-chlorophenyl)-N-(3-methoxy-4-(2-methylpyridin-4-yl)phenyl)-4,5,6,7-tetrahydro-[1,2,3]triazolo[1,5-a]pyridine-3-carboxamide<br>Pale yellow solid | 4.24[a] | 474 | $^1$H NMR δ (ppm)(CHCl$_3$-d): 9.08 (1 H, s), 8.50 (1 H, d, J = 5.18 Hz), 7.69 (1 H, d, J = 2.02 Hz), 7.37-7.26 (5 H, m), 7.20 (1 H, dd, J = 8.25, 2.07 Hz), 6.92 (2 H, d, J = 8.16 Hz), 5.77 (1 H, t, J = 5.47 Hz), 3.90 (3 H, s), 3.43-3.23 (2 H, m), 2.60 (3 H, s), 2.48-2.37 (1 H, m), 2.21-2.12 (1 H, m), 1.92 (2 H, t, J = 6.30 Hz). |
| 17 | 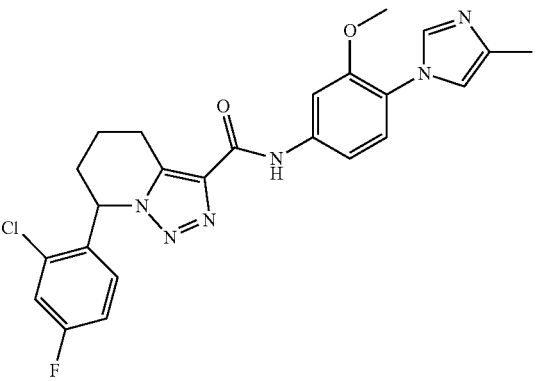 [SMILES: COc1cc(NC(=O)c2nnn3c2CCCC3c2ccc(F)cc2Cl)ccc1-n1cnc(C)c1]<br>7-(2-chloro-4-fluorophenyl)-N-(3-methoxy-4-(4-methyl-1H-imidazol-1-yl)phenyl)-4,5,6,7-tetrahydro-[1,2,3]triazolo[1,5-a]pyridine-3-carboxamide<br>Off white solid | 10.35[c] | 481 | $^1$H NMR δ (ppm)(CHCl$_3$-d): 9.07 (1 H, s), 7.75 (1 H, d, J = 2.17 Hz), 7.66 (1 H, d, J = 1.34 Hz), 7.27-7.18 (2 H, m), 7.15 (1 H, dd, J = 8.48, 2.22 Hz), 7.00-6.87 (2 H, m), 6.43 (1 H, dd, J = 8.76, 5.67 Hz), 6.14 (1 H, t, J = 5.46 Hz), 3.90 (3 H, s), 3.41 (1 H, dt, J = 18.33, 5.75 Hz), 3.27 (1 H, dt, J = 18.43, 7.15 Hz), 2.46-2.35 (1 H, m), 2.30 (3 H, s), 2.01-1.83 (2 H, m). |
| 18 | 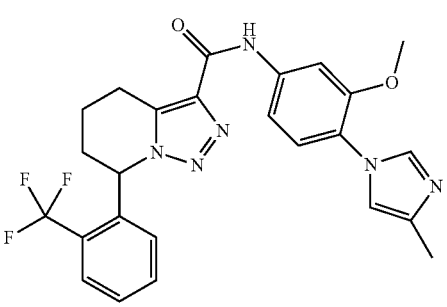 [SMILES: COc1cc(NC(=O)c2nnn3c2CCCC3c2ccccc2C(F)(F)F)ccc1-n1cnc(C)c1]<br>N-(3-methoxy-4-(4-methyl-1H imidazol-1-yl)phenyl)-7-(2-(trifluoromethyl)phenyl)-4,5,6,7-tetrahydro-[1,2,3]triazolo[1,5-a]pyridine-3-carboxamide<br>Pale brown solid | 3.53[a] | 497 | $^1$H NMR δ (ppm)(CHCl$_3$-d): 9.10 (1 H, s), 8.20 (1 H, d, J = 1.48 Hz), 7.84 (1 H, d, J = 2.15 Hz), 7.80-7.75 (1 H, m), 7.54-7.43 (2 H, m), 7.30 (1 H, d, J = 8.52 Hz), 7.17 (1 H, dd, J = 8.55, 2.17 Hz), 7.01 (1 H, s), 6.74 (1 H, d, J = 7.56 Hz), 6.09 (1 H, t, J = 6.30 Hz), 3.99-3.88 (3 H, m), 3.46-3.25 (2 H, m), 2.58-2.49 (1 H, m), 2.40 (3 H, s), 2.17-2.04 (2 H, m), 2.07-1.84 (1 H, m). |

| Ex | Structure | Rt | MS | NMR |
|---|---|---|---|---|
| 19 | 7-(3,4-dichlorophenyl)-N-(3-methoxy-4-(4-methyl-1H-imidazol-1-yl)phenyl)-4,5,6,7-tetrahydro-[1,2,3]triazolo[1,5-a]pyridine-3-carboxamide<br>Off white solid | 10.53[c] | 497 | $^1$H NMR δ (ppm)(CHCl$_3$-d): 9.05 (1 H, s), 7.74 (1 H, d, J = 2.18 Hz), 7.66 (1 H, d, J = 1.33 Hz), 7.48-7.42 (1 H, m), 7.23 (1 H, d, J = 8.44 Hz), 7.15 (1 H, dd, J = 8.46, 2.21 Hz), 7.10 (1 H, d, J = 2.21 Hz), 6.90 (1 H, t, J = 1.21 Hz), 6.83 (1 H, dd, J = 8.34, 2.24 Hz), 5.73 (1 H, t, J = 5.65 Hz), 3.90 (3 H, s), 3.41-3.24 (2 H, m), 2.50-2.40 (1 H, m), 2.30 (3 H, d, J = 0.99 Hz), 2.22-2.13 (1 H, m), 1.97-1.88 (2 H, m). |
| 20 | 7-(4-fluorophenyl)-N-(3-methoxy-4-(4-methyl-1H-imidazol-1-yl)phenyl)-4,5,6,7-tetrahydro-[1,2,3]triazolo[1,5-a]pyridine-3-carboxamide<br>White solid | 2.76[b] | 447 | $^1$H NMR δ (ppm)(CHCl$_3$-d): 9.06 (1 H, s), 7.75 (1 H, d, J = 2.15 Hz), 7.66 (1 H, d, J = 1.33 Hz), 7.23 (1 H, d, J = 8.44 Hz), 7.14 (1 H, dd, J = 8.46, 2.19 Hz), 7.11-7.02 (2 H, m), 6.97 (2 H, dd, J = 8.47, 5.11 Hz), 6.90 (1 H, s), 5.77 (1 H, t, J = 5.59 Hz), 3.90 (3 H, s), 3.41-3.22 (2 H, m), 2.43 (1 H, ddt, J = 14.18, 8.59, 4.69 Hz), 2.30 (3 H, s), 2.23-2.13 (1 H, m), 2.00-1.84 (2 H, m). |
| 21 | 7-(4-fluorophenyl)-N-(4-(2-methylpyridin-4-yl)phenyl)-4,5,6,7-tetrahydro-[1,2,3]triazolo[1,5-a]pyridine-3-carboxamide<br>Beige solid | 9.69[e] | 428 | $^1$H NMR δ (ppm)(CHCl$_3$-d): 9.08 (1 H, s), 8.54 (1 H, d, J = 5.26 Hz), 7.86-7.78 (2 H, m), 7.70-7.62 (2 H, m), 7.39 (1 H, s), 7.33 (1 H, dd, J = 5.41, 1.78 Hz), 7.10-7.02 (2 H, m), 7.01-6.90 (2 H, m), 5.79-5.72 (1 H, m), 3.41-3.22 (2 H, m), 2.75-2.48 (3 H, m), 2.48-2.37 (1 H, m), 2.23-2.13 (1 H, m), 1.98-1.88 (2 H, m). |

| Ex | Structure | Rt | MS | NMR |
|---|---|---|---|---|
| 22 | N-(3-methoxy-4-(4-methyl-1H-imidazol-1-yl)phenyl)-7-(3-(trifluoromethyl)phenyl)-4,5,6,7-tetrahydro-[1,2,3]triazolo[1,5-a]pyridine-3-carboxamide<br>Beige solid | 2.91[b] | 497 | $^1$H NMR δ (ppm)(CHCl$_3$-d): 9.09 (1 H, s), 7.75 (1 H, d, J = 2.17 Hz), 7.66 (1 H, d, J = 1.34 Hz), 7.62 (1 H, d, J = 7.91 Hz), 7.54-7.47 (1 H, m), 7.32 (1 H, s), 7.23 (1 H, d, J = 8.44 Hz), 7.16 (1 H, dd, J = 8.47, 2.19 Hz), 7.12 (1 H, d, J = 7.85 Hz), 6.90 (1 H, s), 5.83 (1 H, t, J = 5.70 Hz), 3.90 (3 H, s), 3.41-3.28 (2 H, m), 2.54-2.44 (1 H, m), 2.30 (3 H, d, J = 1.01 Hz), 2.27-2.17 (1 H, m), 1.95 (2 H, p, J = 6.10 Hz). |
| 23 | (R)-7-(4-chlorophenyl)-N-(3-methoxy-4-(4-methyl-1H-imidazol-1-yl)phenyl)-4,5,6,7-tetrahydro-[1,2,3]triazolo[1,5-a]pyridine-3-carboxamide<br>White solid | 2.83[b]<br>23.18[f]<br>37.2[i] | 463 | $^1$H NMR δ (ppm)(CHCl$_3$-d): 9.07 (1 H, s), 7.75 (1 H, s), 7.66 (1 H, s), 7.35 (2 H, d, J = 8.12 Hz), 7.23 (1 H, d, J = 8.47 Hz), 7.15 (1 H, dd, J = 8.49, 2.17 Hz), 6.94-6.87 (3 H, m), 5.76 (1 H, t, J = 5.49 Hz), 3.90 (3 H, s), 3.42-3.22 (2 H, m), 2.48-2.38 (1 H, m), 2.30 (3 H, s), 2.23-2.13 (1 H, m), 1.92 (2 H, t, J = 6.35 Hz).<br>[α]$_D^{25}$ = −8.2 (c 2.81, CHCl$_3$) |
| 24 | (S)-7-(4-chlorophenyl)-N-(3-methoxy-4-(4-methyl-1H-imidazol-1-yl)phenyl)-4,5,6,7-tetrahydro-[1,2,3]triazolo[1,5-a]pyridine-3-carboxamide<br>White solid | 2.83[b]<br>18.28[f]<br>22.7[i] | 463 | $^1$H NMR δ (ppm)(CHCl$_3$-d): 9.07 (1 H, s), 7.75 (1 H, s), 7.66 (1 H, s), 7.35 (2 H, d, J = 8.12 Hz), 7.23 (1 H, d, J = 8.47 Hz), 7.15 (1 H, dd, J = 8.49, 2.17 Hz), 6.94-6.87 (3 H, m), 5.76 (1 H, t, J = 5.49 Hz), 3.90 (3 H, s), 3.42-3.22 (2 H, m), 2.48-2.38 (1 H, m), 2.30 (3 H, s), 2.23-2.13 (1 H, m), 1.92 (2 H, t, J = 6.35 Hz). |

| Ex | Structure | Rt | MS | NMR |
|---|---|---|---|---|
| 25 | 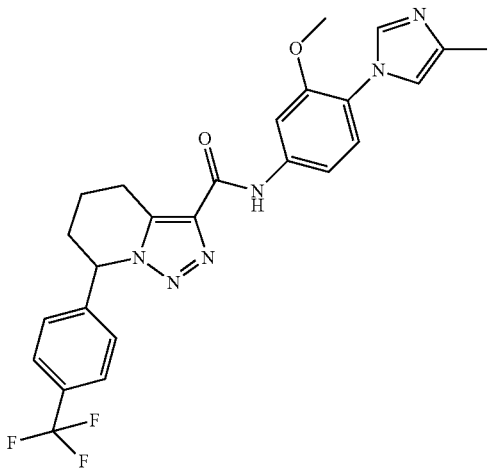 [SMILES: COc1cc(NC(=O)c2nnn3c2CCCC3c2ccc(C(F)(F)F)cc2)ccc1-n1cnc(C)c1]<br>N-(3-methoxy-4-(4-methyl-1H-imidazol-1-yl)phenyl)-7-(4-(trifluoromethyl)phenyl)-4,5,6,7-tetrahydro-[1,2,3]triazolo[1,5-a]pyridine-3-carboxamide<br>White solid | 10.33$^c$ | 497 | $^1$H NMR (400 MHz, CHCl$_3$-d): δ 9.08 (s, 1 H); 7.83 (d, J = 1.39 Hz, 1 H); 7.78 (d, J = 2.18 Hz, 1 H); 7.64 (d, J = 8.09 Hz, 2 H); 7.24 (s, 1 H); 7.16 (dd, J = 8.47, 2.20 Hz, 1 H); 7.10 (d, J = 8.05 Hz, 2 H); 6.93 (s, 1 H); 5.85 (t, J = 5.55 Hz, 1 H); 3.91 (s, 3 H); 3.44-3.23 (m, 2 H); 2.53-2.42 (m, 1 H); 2.33 (d, J = 1.03 Hz, 3 H); 2.26-2.16 (m, 1 H); 1.98-1.88 (m, 2 H). |

The following compounds were prepared from intermediate Q

| Ex | Structure | Rt | MS | NMR |
|---|---|---|---|---|
| 26 | 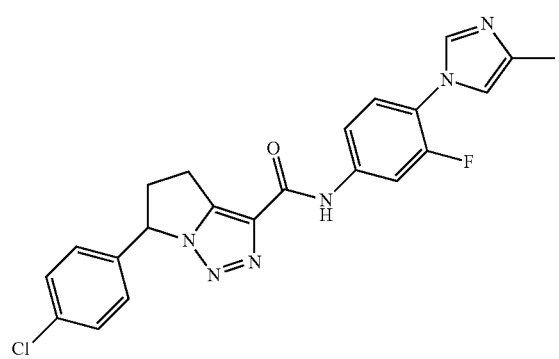 [SMILES: Cc1cn(-c2ccc(NC(=O)c3nnn4c3CCC4c3ccc(Cl)cc3)cc2F)cn1]<br>6-(4-chlorophenyl)-N-(3-fluoro-4-(4-methyl-1H-imidazol-1-yl)phenyl)-5,6-dihydro-4H-pyrrolo[1,2-c][1,2,3]triazole-3-carboxamide<br>Off white solid | 3.84$^a$ | 437 | $^1$H NMR δ (ppm)(CHCl$_3$-d): 9.03 (1 H, s), 7.93 (1 H, dd, J = 12.60, 2.23 Hz), 7.70 (1 H, s), 7.42-7.30 (4 H, m), 7.11 (2 H, d, J = 8.20 Hz), 6.96 (1 H, s), 5.71 (1 H, t, J = 6.76 Hz), 3.41-3.23 (3 H, m), 2.86-2.78 (1 H, m), 2.31 (3 H, s). |

| Ex | Structure | Rt | MS | NMR |
|---|---|---|---|---|
| 27 | 6-(4-chlorophenyl)-N-(3-cyano-4-(4-methyl-1H-imidazol-1-yl)phenyl)-5,6-dihydro-4H-pyrrolo[1,2-c][1,2,3]triazole-3-carboxamide<br>Off white solid | 9.89[c] | 444 | $^1$H NMR δ (ppm)(CHCl$_3$-d): 9.13 (1 H, s), 8.35 (1 H, d, J = 2.50 Hz), 7.91 (1 H, dd, J = 8.78, 2.54 Hz), 7.73 (1 H, d, J = 1.49 Hz), 7.40 (3 H, t, J = 7.90 Hz), 7.12 (2 H, d, J = 8.20 Hz), 7.05 (1 H, s), 5.72 (1 H, t, J = 6.81 Hz), 3.43-3.22 (3 H, m), 2.88-2.77 (1 H, m), 2.32 (3 H, s). |
| 28 | 6-(4-chlorophenyl)-N-(3-methoxy-4-(4-methyl-1H-imidazol-1-yl)phenyl)-5,6-dihydro-4H-pyrrolo[1,2-c][1,2,3]triazole-3-carboxamide<br>Yellow solid | 2.76[b] | 449 | $^1$H NMR δ (ppm)(CHCl$_3$-d): 9.02 (1 H, s), 7.77 (1 H, d, J = 2.24 Hz), 7.66 (1 H, s), 7.39 (2 H, d, J = 8.17 Hz), 7.23 (1 H, d, J = 8.61 Hz), 7.16-7.09 (3 H, m), 6.90 (1 H, s), 5.71 (1 H, t, J = 6.65 Hz), 3.89 (3 H, s), 3.42-3.24 (3 H, m), 2.86-2.77 (1 H, m), 2.30 (3 H, s). |
| 29 | 6-(4-chlorophenyl)-N-(6-methoxy-5-(4-methyl-1H-imidazol-1-yl)pyridin-2-yl)- | 9.9[e] | 450 | $^1$H NMR δ (ppm)(CHCl$_3$-d): 9.43 (1 H, s), 7.96 (1 H, d, J = 8.26 Hz), 7.70 (1 H, s), 7.59 (1 H, d, J = 8.25 Hz), 7.39 (2 H, d, J = 8.18 Hz), 7.11 (2 H, d, J = 8.16 Hz), 6.93 (1 H, s), 5.72 (1 H, t, J = 6.71 Hz), 3.97 (3 H, s), 3.42-3.26 (3 H, m), 2.85-2.77 (1 H, m), 2.30 (3 H, s). |

| Ex | Structure | Rt | MS | NMR |
|---|---|---|---|---|
| | 5,6-dihydro-4H-pyrrolo[1,2-c][1,2,3]triazole-3-carboxamide<br>Yellow solid | | | |
| 30 | (R)-6-(4-chlorophenyl)-N-(3-methoxy-4-(4-methyl-1H-imidazol-1-yl)phenyl)-5,6-dihydro-4H-pyrrolo[1,2-c][1,2,3]triazole-3-carboxamide<br>White solid | 9.80[e]<br>11.81[g] | 449 | $^1$H NMR δ (ppm)(CHCl$_3$-d): 9.02 (1 H, s), 7.78 (1 H, d, J = 2.20 Hz), 7.69 (1 H, d, J = 1.35 Hz), 7.41-7.37 (2 H, m), 7.23 (1 H, d, J = 8.46 Hz), 7.16-7.09 (3 H, m), 6.90 (1 H, s), 5.71 (1 H, t, J = 6.76 Hz), 3.90 (3 H, s), 3.42-3.23 (3 H, m), 2.86-2.75 (1 H, m), 2.31 (3 H, s). |
| 31 | (S)-6-(4-chlorophenyl)-N-(3-methoxy-4-(4-methyl-1H-imidazol-1-yl)phenyl)-5,6-dihydro-4H-pyrrolo[1,2-c][1,2,3]triazole-3-carboxamide<br>White solid | 9.77[e]<br>9.17[g] | 449 | $^1$H NMR δ (ppm)(CHCl$_3$-d): 9.02 (1 H, s), 7.78 (1 H, d, J = 2.20 Hz), 7.69 (1 H, d, J = 1.35 Hz), 7.41-7.37 (2 H, m), 7.23 (1 H, d, J = 8.46 Hz), 7.16-7.09 (3 H, m), 6.90 (1 H, s), 5.71 (1 H, t, J = 6.76 Hz), 3.90 (3 H, s), 3.42-3.23 (3 H, m), 2.86-2.75 (1 H, m), 2.31 (3 H, s). |
| 32 | 6-(2-chlorophenyl)-N-(3-methoxy-4-(4-methyl-1H-imidazol-1-yl)phenyl)-5,6-dihydro-4H-pyrrolo[1,2-c][1,2,3]triazole-3-carboxamide<br>Off white solid | 3.76[a] | 449 | $^1$H NMR δ (ppm)(DMSOd$_6$): 10.64 (1H, s), 7.90 (1H, s), 7.72 1H, s), 7.62-7.58 (2H, m), 7.46-7.36 (2H, m), 7.32 (1H, d), 7.09 (1H, s), 6.99 (1H, d), 6.21-6.17 (1H, m), 3.81 (3H, s), 3.40-3.33 (1H, m), 3.24-3.20 (2H, m), 2.51 (1H, m), 2.15 (3H, s) |

| Ex | Structure | Rt | MS | NMR |
|---|---|---|---|---|
| 33 | 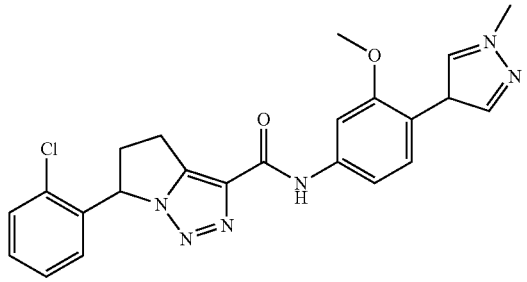<br>6-(2-chlorophenyl)-N-(3-methoxy-4-(1-methyl-1H-pyrazol-4-yl)phenyl)-5,6-dihydro-4H-pyrrolo[1,2-c][1,2,3]triazole-3-carboxamide<br>Pale pink solid | 3.79$^a$ | 449 | $^1$H NMR δ (ppm)(DMSOd$_6$): 10.44 (1H, s), 8.06 (1H, s), 7.86 (1H, s), 7.75 (1H, s), 5.98 (1H, d), 7.55 (2H, m), 7.45-7.36 (2H, m), 6.97, (1H, d), 6.2-6.16 (1H, q), 3.87 (6H, s), 3.31 (1H, m), 3.24-3.19 (2H, m), 2.68 (1H, m) |
| 34 | 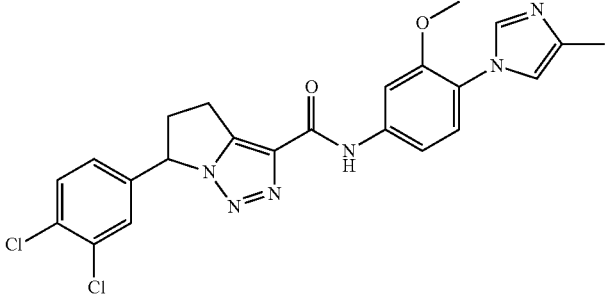 [SMILES: COc1cc(NC(=O)c2nnn3c2CCC3c2ccc(Cl)c(Cl)c2)ccc1-n1cnc(C)c1]<br>6-(3,4-dichlorophenyl)-N-(3-methoxy-4-(4-methyl-1H-imidazol-1-yl)phenyl)-5,6-dihydro-4H-pyrrolo[1,2-c][1,2,3]triazole-3-carboxamide<br>Brown solid | 3.94$^a$ | 483 | $^1$H NMR δ (ppm)(CHCl$_3$-d): 9.01 (1 H, s), 7.77 (1 H, d, J = 2.19 Hz), 7.66 (1 H, s), 7.54-7.46 (1 H, m), 7.28 (1 H, d, J = 2.32 Hz), 7.23 (1 H, d, J = 8.44 Hz), 7.13 (1 H, dd, J = 8.45, 2.24 Hz), 7.05-6.99 (1 H, m), 6.90 (1 H, s), 5.68 (1 H, t, J = 6.86 Hz), 3.90 (3 H, s), 3.44-3.23 (3 H, m), 2.86-2.75 (1 H, m), 2.30 (3 H, s) |
| 35 | 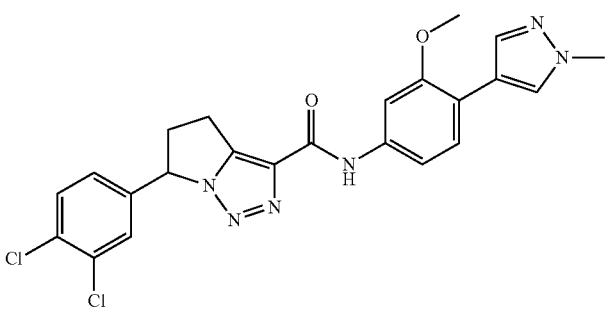 [SMILES: COc1cc(NC(=O)c2nnn3c2CCC3c2ccc(Cl)c(Cl)c2)ccc1-c1cnn(C)c1]<br>6-(3,4-dichlorophenyl)-N-(3-methoxy-4-(1-methyl-1H-pyrazol-4-yl)phenyl)-5,6-dihydro-4H-pyrrolo[1,2-c][1,2,3]triazole-3-carboxamide<br>Brown solid | 3.98$^a$ | 483 | $^1$H NMR δ (ppm)(CHCl$_3$-d): 8.95 (1 H, s), 7.84 (2 H, d, J = 11.47 Hz), 7.67 (1 H, d, J = 2.07 Hz), 7.51-7.46 (2 H, m), 7.28 (1 H, d, J = 2.22 Hz), 7.11 (1 H, dd, J = 8.28, 2.09 Hz), 7.01 (1 H, dd, J = 8.32, 2.20 Hz), 5.67 (1 H, t, J = 6.77 Hz), 3.96 (3 H, s), 3.95 (3 H, s), 3.43-3.23 (3 H, m), 2.85-2.74 (1 H, m) |

| Ex | Structure | Rt | MS | NMR |
|---|---|---|---|---|
| 36 | 6-(4-fluorophenyl)-N-(3-methoxy-4-(4-methyl-1H-imidazol-1-yl)phenyl)-5,6-dihydro-4H-pyrrolo[1,2-c][1,2,3]triazole-3-carboxamide<br>Off white solid | 3.46$^a$ | 433 | $^1$H NMR δ (ppm)(DMSOd$_6$): 10.61 (1H, s), 7.90 (1H, d), 7.71 (1H, d), 7.60 (1H, d), 7.41-7.36 (1H, m), 7.32-7.24 (3H, m), 7.08 (1H, t), 5.90 (1H, q), 3.81 (3H, s), 3.24-3.14 (3H, m), 2.76-2.71 (1H, m), 2.15 (3H, s) |
| 37 | 6-(4-fluorophenyl)-N-(3-methoxy-4-(1-methyl-1H-pyrazol-4-yl)phenyl)-5,6-dihydro-4H-pyrrolo[1,2-c][1,2,3]triazole-3-carboxamide<br>Off white solid | 3.82$^b$ | 433 | $^1$H NMR δ (ppm)(DMSOd$_6$): 10.41 (1H, s), 8.06 (1H, s), 7.86 (1H, s), 7.75-7.50 (2H, m), 7.39-7.36 (2H, m), 7.28-7.24 (2H, m), 5.89 (1H, q), 3.87 (6H, s), 3.27-3.16 (3H, m), 2.71 (1H, m) |

The following compound was prepared from intermediate W

| Ex | Structure | Rt | MS | NMR |
|---|---|---|---|---|
| 38 | 7-(4-chlorophenyl)-N-(3-methoxy-4-(4-methyl-1H-imidazol-1-yl)phenyl)-6,7-dihydro-4H-[1,2,3]triazolo[5,1-c][1,4]oxazine-3-carboxamide<br>White gum | 3.42$^h$ | 465 | $^1$H NMR (CDCl$_3$, 300 MHz) δ 8.94-8.89 (m, 1H), 7.66-7.58 (m, 2H), 7.35 (d, J = 7 Hz, 2H), 7.20-7.05 (m, 4H), 6.84 (s, 1H), 5.59 (t, J = 7 Hz, 1H), 5.27 (dd, J = 10, 3 Hz, 2H), 4.23 (dd, J = 6, 1.5 Hz, 1H), 4.03 (dd, J = 6, 1.5 Hz, 1H), 3.83 (s, 3H), 2.74 (s, 3H). |

General Method D:

To a suitably substituted triazolo amine (0.247 mmol) in DMF (1 mL) was added a suitably substituted carboxylic acid (0.247 mmol), HATU (O-(7-Azabenzotriazol-1-yl)-N,N,N',N'-tetramethyluronium hexafluorophosphate) (0.272 mmol) followed by diisopropylethylamine (0.742 mmol) and stirred at 25° C. for 18 hours. The reaction mixture was purified directly by preparative HPLC to afford pure amide.

The following compounds were prepared from intermediate J

| Ex | Structure | Rt | MS | NMR |
|---|---|---|---|---|
| 39 | 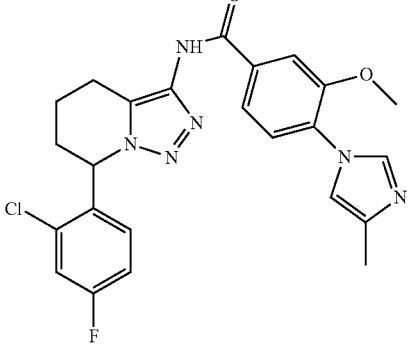<br>N-(7-(2-chloro-4-fluorophenyl)-4,5,6,7-tetrahydro-[1,2,3]triazolo[1,5-a]pyridin-3-yl)-3-methoxy-4-(4-methyl-1H-imidazol-1-yl)benzamide<br>Pale yellow gum | 3.6$^a$ | 481 | $^1$H NMR δ (ppm)(CHCl$_3$-d): 10.63 (1 H, s), 7.99 (1 H, s), 7.78-7.72 (2 H, m), 7.29 (1 H, d, J = 8.40 Hz), 7.20 (1 H, dd, J = 8.21, 2.61 Hz), 6.99-6.86 (2 H, m), 6.57 (1 H, dd, J = 8.75, 5.71 Hz), 6.06 (1 H, t, J = 5.70 Hz), 3.85 (3 H, s), 3.15 (1 H, dt, J = 17.46, 6.01 Hz), 3.04-2.94 (1 H, m), 2.48-2.37 (1 H, m), 2.34 (3 H, s), 2.27-2.18 (1 H, m), 1.90 (2 H, t, J = 6.65 Hz). |
| 40 | 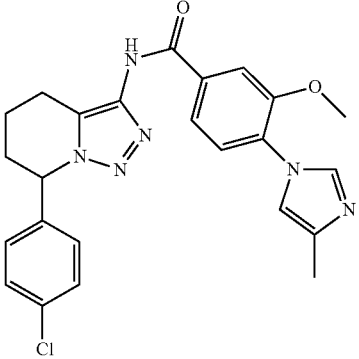 [SMILES: COc1cc(C(=O)Nc2nnn3c2CCCC3c2ccc(Cl)cc2)ccc1-n1cnc(C)c1]<br>N-(7-(4-chlorophenyl)-4,5,6,7-tetrahydro-[1,2,3]triazolo[1,5-a]pyridin-3-yl)-3-methoxy-4-(4-methyl-1H-imidazol-1-yl)benzamide<br>Beige solid | 2.64$^b$ | 463 | $^1$H NMR δ (ppm)(DMSO-d$_6$): 10.77 (1 H, s), 7.94-7.84 (2 H, m), 7.74 (1 H, dd, J = 8.22, 1.81 Hz), 7.56 (1 H, d, J = 8.18 Hz), 7.45 (2 H, t, J = 8.32 Hz), 7.25 (1 H, s), 7.08 (2 H, d, J = 8.26 Hz), 5.86 (1 H, t, J = 5.74 Hz), 3.95 (3 H, s), 2.93-2.74 (2 H, m), 2.40-2.31 (1 H, m), 2.17 (3 H, s), 2.12-2.04 (1 H, m), 1.77 (2 H, s). |
| 41 | 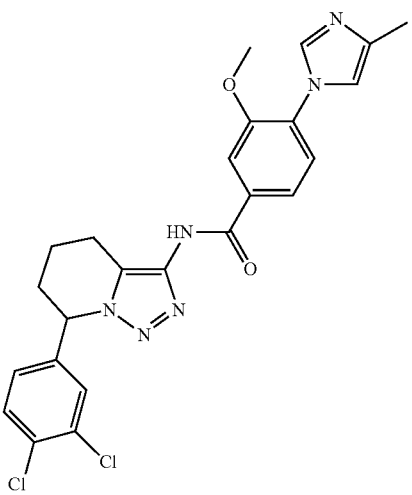 [SMILES: COc1cc(C(=O)Nc2nnn3c2CCCC3c2ccc(Cl)c(Cl)c2)ccc1-n1cnc(C)c1]<br>N-(7-(3,4-dichlorophenyl)-4,5,6,7-tetrahydro- | 2.76$^b$ | 497 | $^1$H NMR δ (ppm)(CHCl$_3$-d): 10.10 (1 H, s), 7.78 (1 H, d, J = 1.34 Hz), 7.72-7.65 (2 H, m), 7.43 (1 H, d, J = 8.30 Hz), 7.29 (1 H, d, J = 8.11 Hz), 7.16 (1 H, d, J = 2.15 Hz), 6.95 (1 H, s), 6.89 (1 H, dd, J = 8.33, 2.19 Hz), 5.62 (1 H, t, J = 5.98 Hz), 3.86 (3 H, s), 3.17-2.99 (2 H, m), 2.48-2.39 (1 H, m), 2.31 (3 H, s), 2.21-2.11 (1 H, m), 1.97-1.84 (2 H, m). |

-continued

| Ex | Structure | Rt | MS | NMR |
|---|---|---|---|---|
| | [1,2,3]triazolo[1,5-a]pyridin-3-yl)-3-methoxy-4-(4-methyl-1H-imidazol-1-yl)benzamide<br>Pale yellow solid | | | |
| 42 | 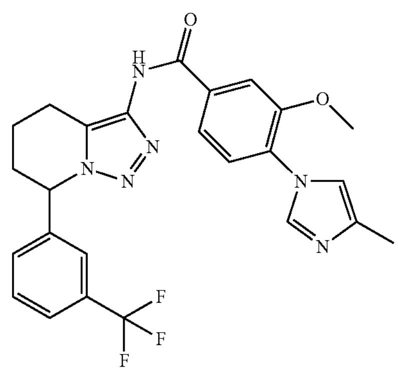 [SMILES: COc1cc(C(=O)Nc2nnn3c2CCCC3c2cccc(C(F)(F)F)c2)ccc1-n1cnc(C)c1] | 2.71[b] | 497 | $^1$H NMR (400 MHz, CHCl$_3$-d): δ 10.15 (s, 1 H); 8.09 (s, 1 H); 7.72 (d, J = 10.46 Hz, 2 H); 7.59 (d, J = 7.88 Hz, 1 H); 7.53-7.45 (m, 1 H); 7.39 (s, 1 H); 7.30 (d, J = 8.03 Hz, 1 H); 7.20 (d, J = 7.86 Hz, 1 H); 7.00 (s, 1 H); 5.73 (t, J = 6.03 Hz, 1 H); 3.85 (s, 3 H); 3.17-2.99 (m, 2 H); 2.52-2.44 (m, 1 H); 2.34 (s, 3 H); 2.24-2.14 (m, 1 H); 2.00-1.87 (m, 2 H). |
| | 3-methoxy-4-(4-methyl-1H-imidazol-1-yl)-N-(7-(3-(trifluoromethyl)phenyl)-4,5,6,7-tetrahydro-[1,2,3]triazolo[1,5-a]pyridin-3-yl)benzamide<br>Off white solid | | | |
| 43 | 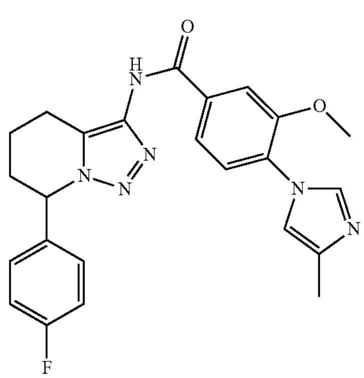 [SMILES: COc1cc(C(=O)Nc2nnn3c2CCCC3c2ccc(F)cc2)ccc1-n1cnc(C)c1] | 2.63[a] | 447 | $^1$H NMR (400 MHz, DMSO-d$^6$): δ 10.77 (s, 1 H); 8.04 (s, 1 H); 7.88 (s, 1 H); 7.74 (d, J = 8.23 Hz, 1 H); 7.57 (d, J = 8.16 Hz, 1 H); 7.30 (s, 1 H); 7.23 (t, J = 8.63 Hz, 2 H); 7.11 (t, J = 6.52 Hz, 2 H); 5.84 (t, J = 5.75 Hz, 1 H); 3.95 (s, 3 H); 2.92-2.73 (m, 2 H); 2.36 (d, J = 14.45 Hz, 1 H); 2.19 (s, 3 H); 2.13-2.04 (m, 1 H); 1.78 (s, 2 H). |
| | N-(7-(4-fluorophenyl)-4,5,6,7-tetrahydro-[1,2,3]triazolo[1,5-a]pyridin-3-yl)-3-methoxy-4-(4-methyl-1H-imidazol-1-yl)benzamide<br>Beige solid | | | |

The following compounds were prepared from intermediate R

| Ex | Structure | Rt | MS | NMR |
|---|---|---|---|---|
| 44 | N-(6-(4-chlorophenyl)-5,6-dihydro-4H-pyrrolo[1,2-c][1,2,3]triazol-3-yl)-3-methoxy-4-(4-methyl-1H-imidazol-1-yl)benzamide<br>White solid | 3.07$^a$ | 449 | $^1$H NMR δ (ppm)(CH$_3$OH-d$^6$): 8.36 (1 H, s), 7.87 (1 H, d, J = 1.80 Hz), 7.76 (1 H, dd, J = 8.18, 1.85 Hz), 7.61 (1 H, d, J = 8.19 Hz), 7.46-7.42 (2 H, m), 7.35 (1 H, s), 7.32-7.24 (2 H, m), 5.79 (1 H, dd, J = 7.93, 5.50 Hz), 4.03 (3 H, s), 3.39-3.26 (3 H, m), 2.76-2.66 (1 H, m), 2.34 (3 H, d, J = 1.07 Hz). |
| 45 | N-(6-(3,4-dichlorophenyl)-5,6-dihydro-4H-pyrrolo[1,2-c][1,2,3]triazol-3-yl)-3-methoxy-4-(4-methyl-1H-imidazol-1-yl)benzamide<br>White solid | 2.83$^a$ | 483 | $^1$H NMR (400 MHz, CHCl$_3$-d): δ 9.51 (s, 1 H); 7.83 (s, 1 H); 7.69 (d, J = 1.80 Hz); 7.62 (dd, J = 8.17, 1.85 Hz, 1 H); 7.47 (d, J = 8.30 Hz, 1 H); 7.36 (d, J = 8.12 Hz, 1 H); 7.31 (d, J = 2.20 Hz, 1 H); 7.05 (dd, J = 8.31, 2.18 Hz, 1 H); 6.98 (s, 1 H); 5.62 (dd, J = 8.23, 5.86 Hz, 1 H); 3.95 (s, 3 H); 3.51-3.42 (m, 2 H); 3.28-3.22 (m, 1 H); 2.72-2.66 (m, 1 H); 2.32 (s, 3 H). |
| 46 | N-(6-(4-fluorophenyl)-5,6-dihydro-4H-pyrrolo[1,2-c][1,2,3]triazol-3-yl)-3-methoxy-4-(4-methyl-1H-imidazol-1-yl)benzamide<br>Beige solid | 2.56$^b$ | 433 | $^1$H NMR δ (ppm)(DMSOd$_6$): 11.24 (1H, bs), 7.91 (2H, s), 7.78 (1H, d), 7.21-7.37 (5H, m), 5.83 (1H, q), 3.96 (3H, s), 3.30-3.12 (3H, m), 2.66-2.54 (1H, m), 2.17 (3H, s) |
| 47 | N-(6-(4-fluorophenyl)-5,-dihydro-4H-pyrrolo[1,2-c][1,2,3]triazol-3-yl)-3-methoxy-4-(2-methylpyridin-4-yl)benzamide<br>brown solid | 9.17$^e$ | 444 | $^1$H NMR δ (ppm)(DMSOd$_6$): 11.23 (1H, bs), 8.49 (1H, d), 7.75 (1H, d), 7.50 (1H, d), 7.41 (1H, s), 7.48-7.20 (6H, m), 5.91 (1H, q), 3.89 (3H, s), 3.36-3.10 (3H, m), 2.65-2.55 (1H, m), 2.50 (3H, s) |

General Method E:

To a suitably substituted amide (0.422 mmol) in THF (4 ml) was added NaH (0.422 mmol, 60% in oil) and the reaction was stirred at 25° C. for 1 hour. This was then treated with methyl iodide (0.422 mol) with stirring at 25° C. for 24 hours in a sealed tube. The reaction was partitioned between DCM and water. The combined organic extracts were dried (MgSO$_4$), filtered, and evaporated to dryness under vacuum. The crude residue was dissolved in DMSO and purified by preparative HPLC.

For example, 7-(4-chlorophenyl)-N-(3-methoxy-4-(4-methyl-1H-imidazol-1-yl)phenyl)-N-methyl-4,5,6,7-tetrahydro-[1,2,3]triazolo[1,5-a]pyridine-3-carboxamide was isolated in 19% yield. $^1$H NMR δ (ppm) (CHCl$_3$-d): 7.71 (1H, s), 7.28 (2H, m), 7.21 (1H, d), 6.97 (1H, s), 6.87 (4H, m), 5.63 (1H, t), 3.81 (3H, s), 3.67 (3H, bs), 3.22-3.12 (2H, m), 2.4-2.33 (1H m), 2.30 (3H, s), 2.16-2.08 (1H, m), 1.91-1.83 (2H, m). LC/MS (M+H)$^+$ 477

Both types of salts may be formed or interconverted using ion-exchange resin techniques.

Depending on the conditions used, the reaction times are generally between a few minutes and 14 days. The reaction temperature is between about −30° C. and about 140° C., normally between −10° C. and 90° C., in particular between about 0° C. and 70° C.

Compounds of the formula (I) and related formulae can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in

| Ex | Structure | Rt | MS | NMR |
|---|---|---|---|---|
| 48 | 7-(4-chlorophenyl)-N-(3-methoxy-4-(4-methyl-1H-imidazol-1-yl)phenyl)-N-methyl-4,5,6,7-tetrahydro-[1,2,3]triazolo[1,5-a]pyridine-3-carboxamide<br>White solid | 9.56$^c$ | 477 | $^1$H NMR δ (ppm) (CHCl$_3$-d): 7.71 (1H, s), 7.28 (2H, m), 7.21 (1H, d), 6.97 (1H, s), 6.87 (4H, m), 5.63 (1H, t), 3.81 (3H, s), 3.67 (3H, bs), 3.22-3.12 (2H, m), 2.4-2.33 (1H m), 2.30 (3H, s), 2.16-2.08 (1H, m), 1.91-1.83 (2H, m) |

Compounds of this invention can be isolated in association with solvent molecules by crystallization from an appropriate solvent or by evaporation of an appropriate solvent.

The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of an alkali or earth alkali salt (such as sodium ethylhexanoate, magnesium oleate), employing a solvent in which the desired alkali or earth alkali salt of the compounds of formula (I) precipitates, or can be otherwise isolated by concentration and addition of a non-solvent.

which R* denotes an amino-protecting group, instead of an HN group, and/or those which carry a hydroxyl-protecting group instead of the H atom of a hydroxyl group, for example those which conform to the formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-icarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-icarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, further- more CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl- formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, H2SO4, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called pro- drug compounds.

The term "prodrug derivatives" is taken to mean compounds of the formula I which have been modified with, for example, alkyl or acyl groups, sugars or oligopeptides and which are rapidly cleaved in the organism to form the active compounds. Preferably "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995).

The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I), and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I), and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

Example 49

In Vitro Assays

Amyloidβ Peptide Release (Aβ42 & AβTotal) Assay to Determine $IC_{50}$ Values.

Amyloidβ peptide release (Aβ42 & AβTotal) assay are performed in 384 well microtiter plates (Perkin Elmer AlphaPlate #6008350) in a final volume of 20 μl, using supernatant coming from APPswe-HEK cells exposed to test compounds. Compounds are dissolved in and diluted in 100% DMSO and incubated with APPswe-HEK cells for 24 hours a 37° C. in 5% $CO_2$. The supernatant from APPswe-HEK cells are mixed with antibodies: for Aβ42 detection: AlphaLisa Amyloid β 1-42 Kit (Perkin Elmer AL203L) Anti-Amyloid β1-42-specific antibody acceptor beads, biotinylated anti-Amyloid "β1-42" antibody and streptavidin (SA) donor beads diluted in AlphaLisa buffer (to the instructions of the supplier). For Aβ total detection: Custom Anti-Amyloid βtotal acceptor beads (6E10 acceptor beads), biotinylated anti-Amyloid "β1-42" antibody (Perkin Elmer AL203L) and streptavidin (SA) donor beads diluted in AlphaLisa buffer (to the instructions of the supplier). After addition of supernatant to the antibody mix, the assay is incubated 4 h and 30 minutes. AmyloidP peptide release (Aβ42 & AβTotal) is measured with a Pherastar FS (BMG) multimode reader using the alphascreen module.

Cell Viability Assay to Determine $IC_{50}$ Values.

Cell viability assay are performed in 384 well microtiter plates (Corning #3712) in a final volume of 30 μl, using plates containing APPswe-HEK cells exposed to test compounds for 24 hours. After addition of equal volume of CellTiter-Glo (Promega) to the cells, the assay is incubated 10 minutes. Cell viability is measured with a Pherastar FS (BMG) multimode reader using the Luminescence plus module.

Immunoprecipitation and MALDI-TOF Mass Spectrometry

Human embryonic kidney cells overexpressing APP Swedish Variant$^{K595N/M596L}$ (HEK-APPsw) were grown in the presence of 0.5% dimethylsulfoxide (DMSO) or compound for 16 h. Aβ peptides were immunoprecipitated from conditioned medium with monoclonal mouse antibodies 6E10 and 4G8 (both Covance, Princeton, N.J., USA) at room temperature for 3 h. All samples were spiked with a 60 ng isotopically labeled $^{13}$C $^{15}$N Beta-Amyloid (1-40) (Anaspec, Fremont, Calif., USA) internal calibrant prior to immunoprecipitation. Immunocomplexes were captured with goat anti-mouse IgG magnetic dynabeads (Invitrogen, Paisley, UK) overnight at 4° C. followed by repeated washing of the beads according to (Beher, 2002, J. Neurochem. 82: 563-575). Peptides were eluted from the beads with 0.1% trifluoroacetic acid. Samples were spotted on a MALDI TOF plate and an equivalent 1:1 volume of α-cyano-4-hydroxycinnamic acid matrix in 0.1% trifluoroacetic acid, 50% acetonitrile was also spotted on the plate.

Matrix-assisted laser desorption/ionization time of flight (MALDI-TOF) mass spectrometry of the Aβ peptides was subsequently performed on a Voyager-DE™ PRO mass spectrometer (Applied Biosystems, Foster City, Calif., USA) in linear positive ion mode averaging 5 time 100 shots for each sample. For data analysis the individual peak intensities were normalized to the internal calibrant by calculating the ratio of peptide versus calibrant peak intensity. Changes after compound treatment were expressed relative to the individual ratios obtained for the DMSO control.

| Example No | Structure | Ab42 IC50 Ranges | Abtot/Ab42 selectivity ranges |
|---|---|---|---|
| 1 | 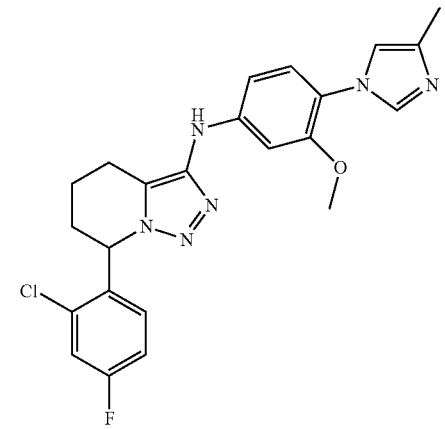 [SMILES: COc1cc(Nc2nnn3c2CCCC3c2ccc(F)cc2Cl)ccc1-n1cnc(C)c1] | b | b |
| 2 | 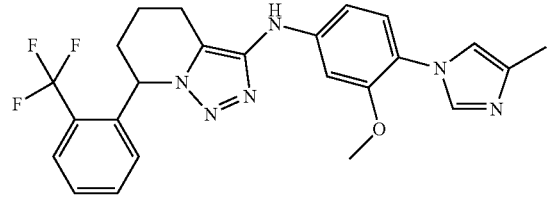 [SMILES: COc1cc(Nc2nnn3c2CCCC3c2ccccc2C(F)(F)F)ccc1-n1cnc(C)c1] | b | a |
| 3 | 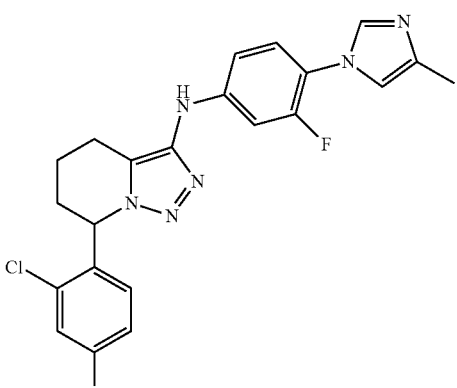 | b | b |

-continued
| Example No | Structure | Ab42 IC50 Ranges | Abtot/Ab42 selectivity ranges |
|---|---|---|---|
| 4 | 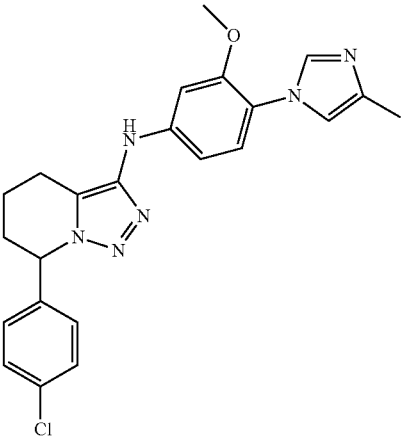 [SMILES: COc1cc(Nc2nnn3c2CCCC3c2ccc(Cl)cc2)ccc1-n1cnc(C)c1] | b | b |
| 5 | 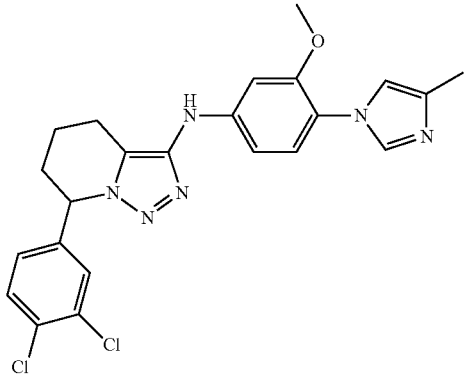 [SMILES: COc1cc(Nc2nnn3c2CCCC3c2ccc(Cl)c(Cl)c2)ccc1-n1cnc(C)c1] | b | b |
| 6 | 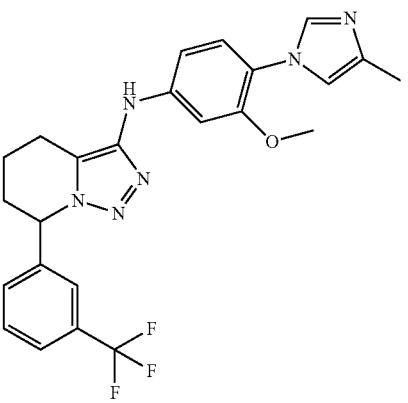 [SMILES: COc1cc(Nc2nnn3c2CCCC3c2cccc(C(F)(F)F)c2)ccc1-n1cnc(C)c1] | b | b |

-continued

| Example No | Structure | Ab42 IC50 Ranges | Abtot/Ab42 selectivity ranges |
|---|---|---|---|
| 7 | 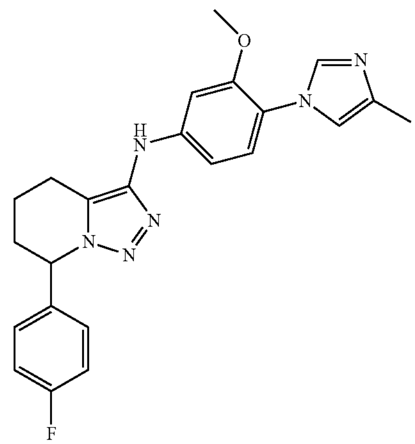 [SMILES: COc1cc(Nc2nnn3c2CCCC3c2ccc(F)cc2)ccc1-n1cnc(C)c1] | b | b |
| 8 | 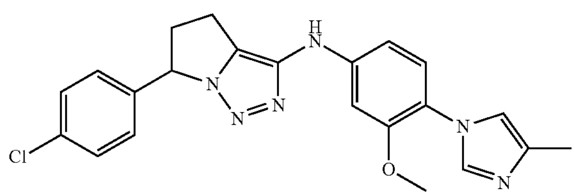 [SMILES: COc1cc(Nc2nnn3c2CCC3c2ccc(Cl)cc2)ccc1-n1cnc(C)c1] | b | a |
| 9 | 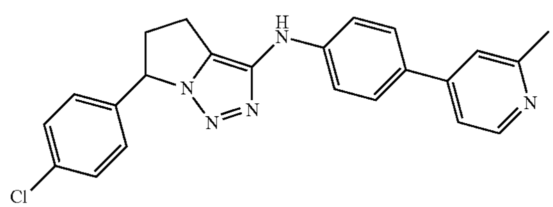 [SMILES: Cc1cc(-c2ccc(Nc3nnn4c3CCC4c3ccc(Cl)cc3)cc2)ccn1] | b | a |
| 10 | 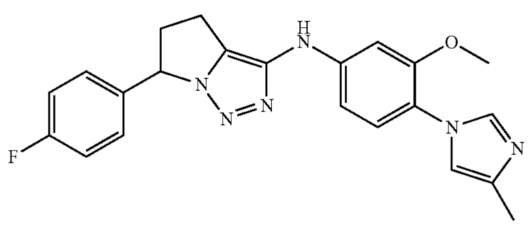 [SMILES: COc1cc(Nc2nnn3c2CCC3c2ccc(F)cc2)ccc1-n1cnc(C)c1] | b | a |
| 11 | 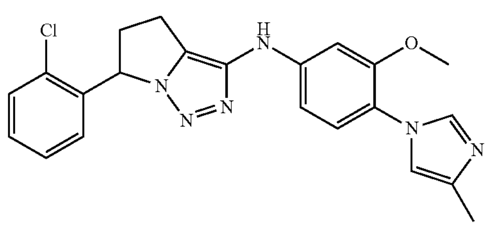 [SMILES: COc1cc(Nc2nnn3c2CCC3c2ccccc2Cl)ccc1-n1cnc(C)c1] | b | b |

-continued

| Example No | Structure | Ab42 IC50 Ranges | Abtot/Ab42 selectivity ranges |
|---|---|---|---|
| 12 | 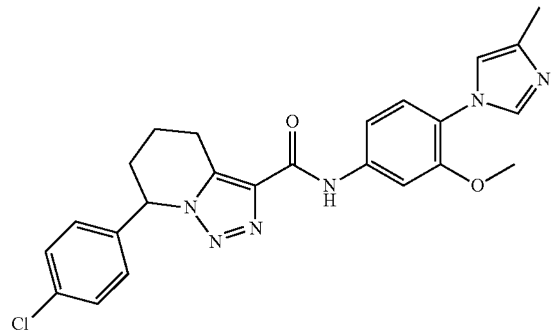 [SMILES: COc1cc(NC(=O)c2nnn3c2CCCC3c2ccc(Cl)cc2)ccc1-n1cnc(C)c1] | a | b |
| 13 | 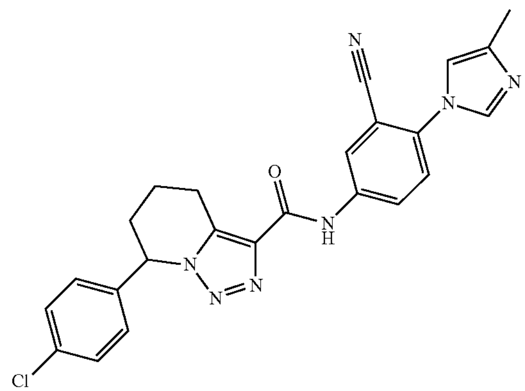 [SMILES: Cc1cn(-c2ccc(NC(=O)c3nnn4c3CCCC4c3ccc(Cl)cc3)cc2C#N)cn1] | b | c |
| 14 | 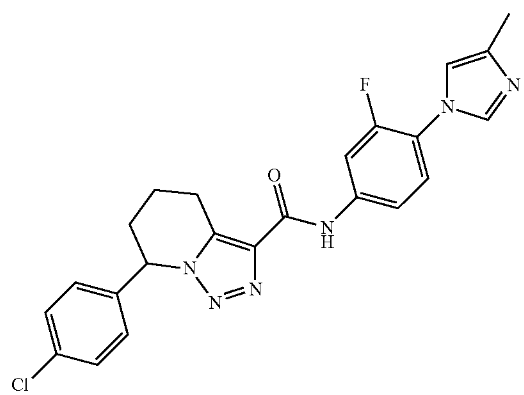 [SMILES: Cc1cn(-c2ccc(NC(=O)c3nnn4c3CCCC4c3ccc(Cl)cc3)cc2F)cn1] | b | c |
| 15 | 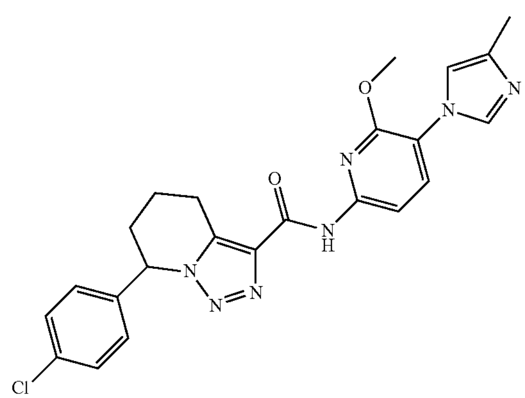 [SMILES: COc1nc(NC(=O)c2nnn3c2CCCC3c2ccc(Cl)cc2)ccc1-n1cnc(C)c1] | c | c |

| Example No | Structure | Ab42 IC50 Ranges | Abtot/Ab42 selectivity ranges |
|---|---|---|---|
| 16 | 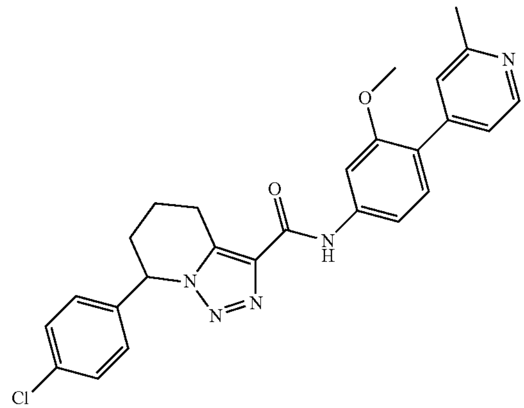 [SMILES: COc1cc(NC(=O)c2nnn3c2CCCC3c2ccc(Cl)cc2)ccc1-c1ccnc(C)c1] | b | c |
| 17 | 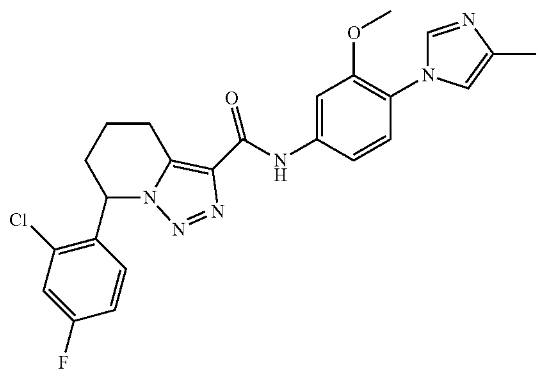 [SMILES: COc1cc(NC(=O)c2nnn3c2CCCC3c2ccc(F)cc2Cl)ccc1-n1cnc(C)c1] | b | c |
| 18 | 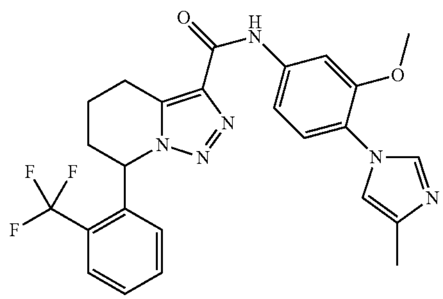 [SMILES: COc1cc(NC(=O)c2nnn3c2CCCC3c2ccccc2C(F)(F)F)ccc1-n1cnc(C)c1] | b | c |
| 19 | 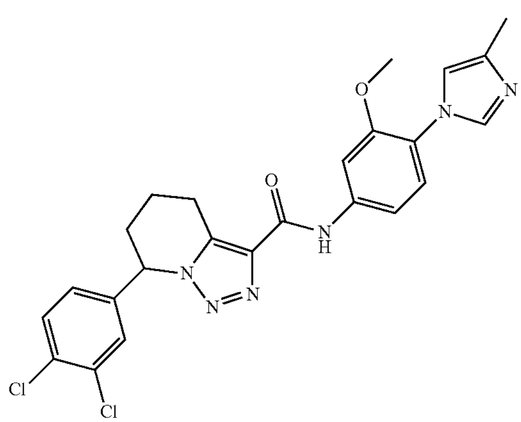 [SMILES: COc1cc(NC(=O)c2nnn3c2CCCC3c2ccc(Cl)c(Cl)c2)ccc1-n1cnc(C)c1] | a | b |

-continued

| Example No | Structure | Ab42 IC50 Ranges | Abtot/Ab42 selectivity ranges |
|---|---|---|---|
| 20 | 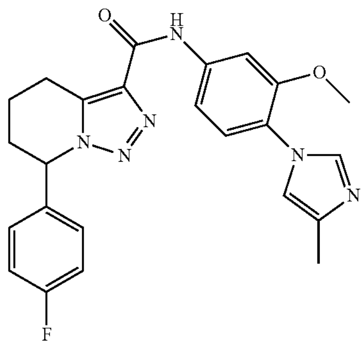 [SMILES: COc1cc(NC(=O)c2nnn3c2CCCC3c2ccc(F)cc2)ccc1-n1cnc(C)c1] | b | b |
| 21 | 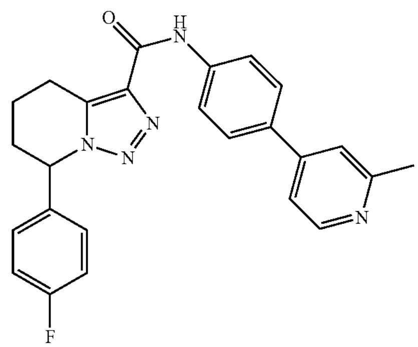 [SMILES: Cc1cc(-c2ccc(NC(=O)c3nnn4c3CCCC4c3ccc(F)cc3)cc2)ccn1] | d | d |
| 22 | 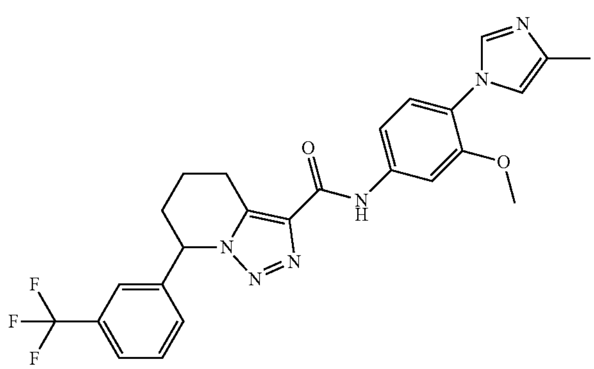 [SMILES: COc1cc(NC(=O)c2nnn3c2CCCC3c2cccc(C(F)(F)F)c2)ccc1-n1cnc(C)c1] | b | b |
| 23 | 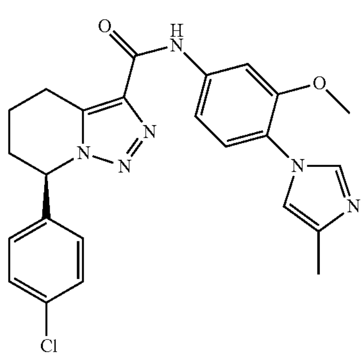 [SMILES: COc1cc(NC(=O)c2nnn3c2CCC[C@@H]3c2ccc(Cl)cc2)ccc1-n1cnc(C)c1] | a | b |

-continued
| Example No | Structure | Ab42 IC50 Ranges | Abtot/Ab42 selectivity ranges |
|---|---|---|---|
| 24 | 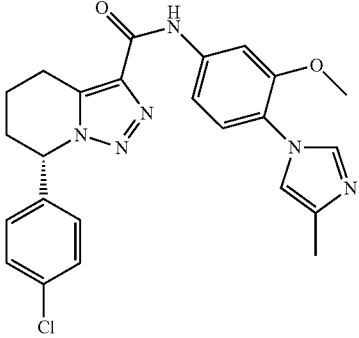 [SMILES: COc1cc(NC(=O)c2nnn3c2CCC[C@H]3c2ccc(Cl)cc2)ccc1-n1cnc(C)c1] | b | b |
| 25 | 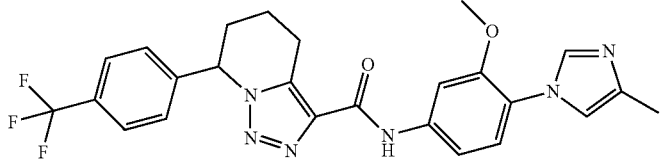 [SMILES: COc1cc(NC(=O)c2nnn3c2CCCC3c2ccc(C(F)(F)F)cc2)ccc1-n1cnc(C)c1] | a | c |
| 26 | 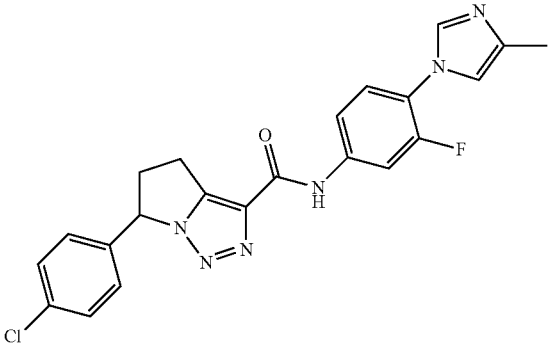 [SMILES: Cc1cn(-c2ccc(NC(=O)c3nnn4c3CCC4c3ccc(Cl)cc3)cc2F)cn1] | b | b |
| 27 | 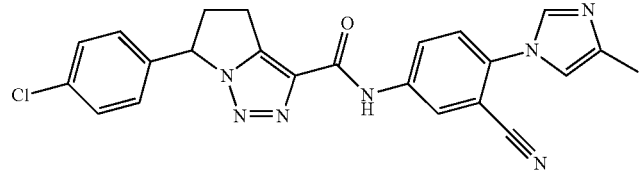 [SMILES: Cc1cn(-c2ccc(NC(=O)c3nnn4c3CCC4c3ccc(Cl)cc3)cc2C#N)cn1] | b | c |
| 28 | 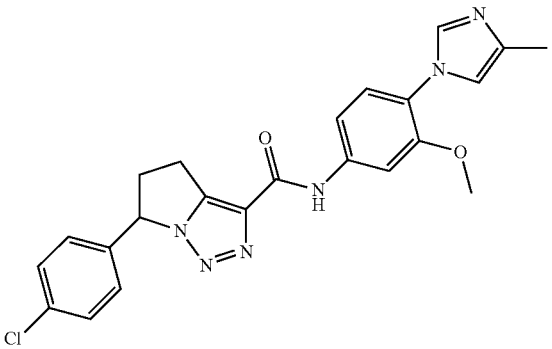 [SMILES: COc1cc(NC(=O)c2nnn3c2CCC3c2ccc(Cl)cc2)ccc1-n1cnc(C)c1] | a | b |

-continued

| Example No | Structure | Ab42 IC50 Ranges | Abtot/Ab42 selectivity ranges |
|---|---|---|---|
| 29 | 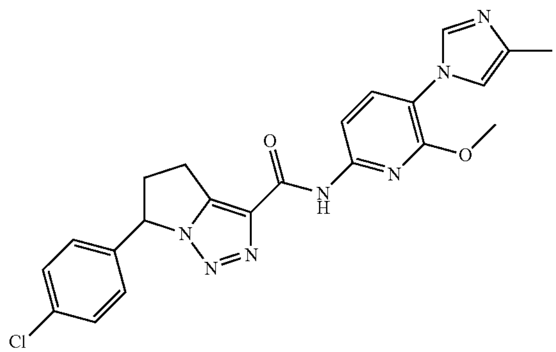 [SMILES: COc1nc(NC(=O)c2nnn3c2CCC3c2ccc(Cl)cc2)ccc1-n1cnc(C)c1] | d | a |
| 30 | 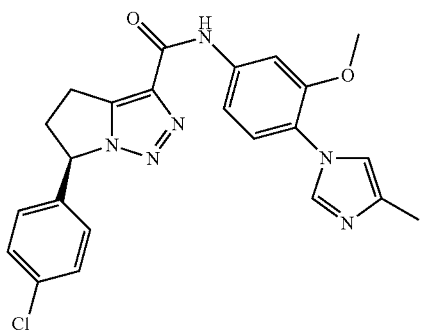 [SMILES: COc1cc(NC(=O)c2nnn3c2CC[C@@H]3c2ccc(Cl)cc2)ccc1-n1cnc(C)c1] | a | b |
| 31 | 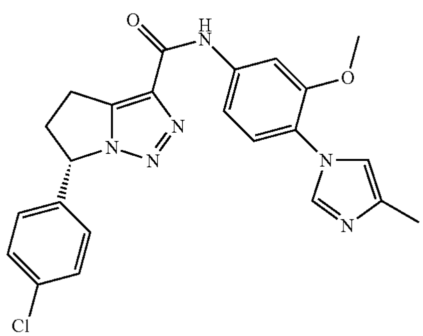 [SMILES: COc1cc(NC(=O)c2nnn3c2CC[C@H]3c2ccc(Cl)cc2)ccc1-n1cnc(C)c1] | b | c |
| 32 | 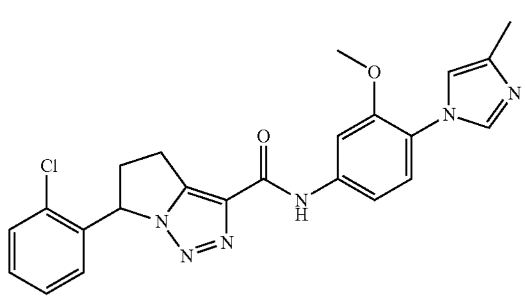 [SMILES: COc1cc(NC(=O)c2nnn3c2CCC3c2ccccc2Cl)ccc1-n1cnc(C)c1] | a | b |

-continued

| Example No | Structure | Ab42 IC50 Ranges | Abtot/Ab42 selectivity ranges |
|---|---|---|---|
| 33 | 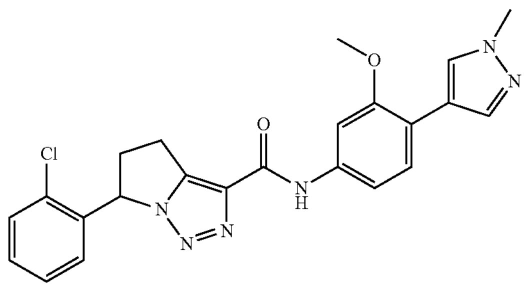 [SMILES: COc1cc(NC(=O)c2nnn3c2CCC3c2ccccc2Cl)ccc1-c1cnn(C)c1] | c | c |
| 34 | 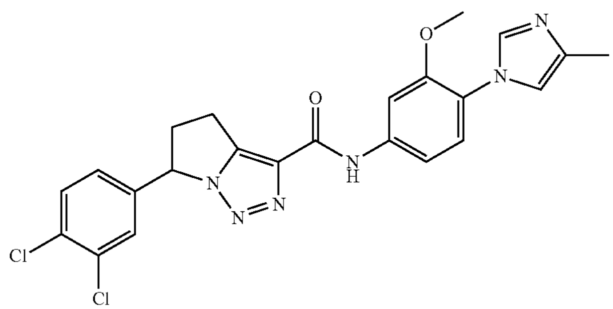 [SMILES: COc1cc(NC(=O)c2nnn3c2CCC3c2ccc(Cl)c(Cl)c2)ccc1-n1cnc(C)c1] | a | a |
| 35 | 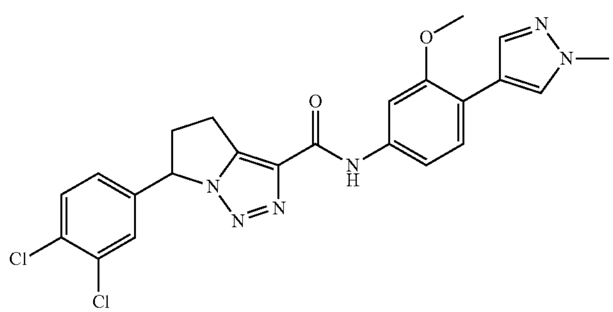 [SMILES: COc1cc(NC(=O)c2nnn3c2CCC3c2ccc(Cl)c(Cl)c2)ccc1-c1cnn(C)c1] | b | c |
| 36 | 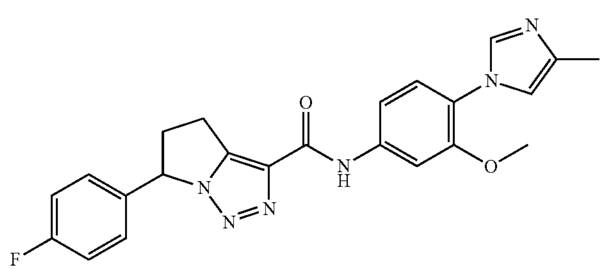 [SMILES: COc1cc(NC(=O)c2nnn3c2CCC3c2ccc(F)cc2)ccc1-n1cnc(C)c1] | b | b |
| 37 | 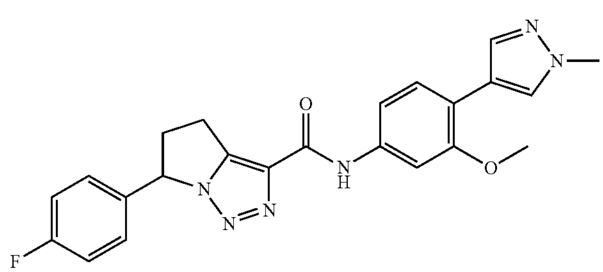 [SMILES: COc1cc(NC(=O)c2nnn3c2CCC3c2ccc(F)cc2)ccc1-c1cnn(C)c1] | d | c |

-continued

| Example No | Structure | Ab42 IC50 Ranges | Abtot/Ab42 selectivity ranges |
|---|---|---|---|
| 38 | 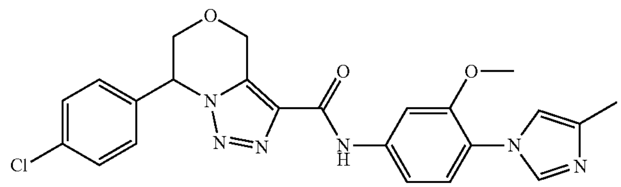 [SMILES: COc1cc(NC(=O)c2nnn3c2COCC3c2ccc(Cl)cc2)ccc1-n1cnc(C)c1] | b | b |
| 39 | 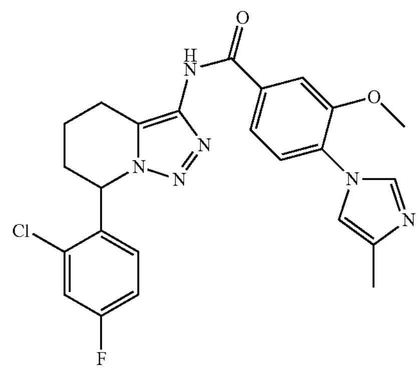 [SMILES: COc1cc(C(=O)Nc2nnn3c2CCCC3c2ccc(F)cc2Cl)ccc1-n1cnc(C)c1] | b | b |
| 40 | 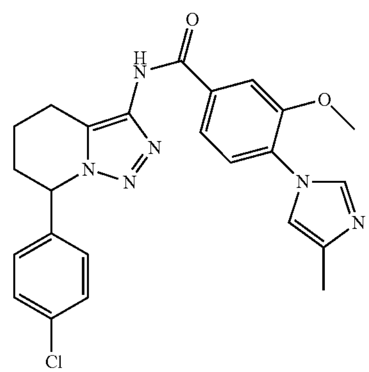 [SMILES: COc1cc(C(=O)Nc2nnn3c2CCCC3c2ccc(Cl)cc2)ccc1-n1cnc(C)c1] | b | b |
| 41 | 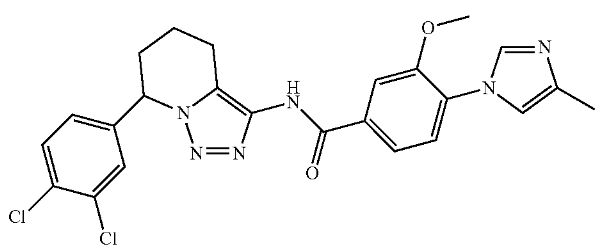 [SMILES: COc1cc(C(=O)Nc2nnn3c2CCCC3c2ccc(Cl)c(Cl)c2)ccc1-n1cnc(C)c1] | b | b |
| 42 | 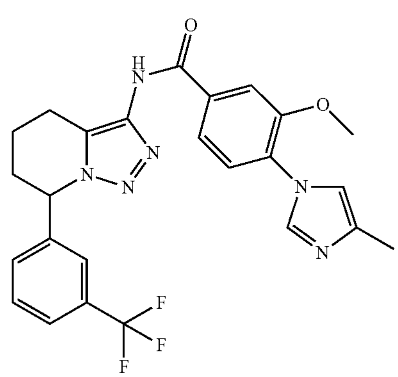 [SMILES: COc1cc(C(=O)Nc2nnn3c2CCCC3c2cccc(C(F)(F)F)c2)ccc1-n1cnc(C)c1] | c | c |

-continued

| Example No | Structure | Ab42 IC50 Ranges | Abtot/Ab42 selectivity ranges |
|---|---|---|---|
| 43 | 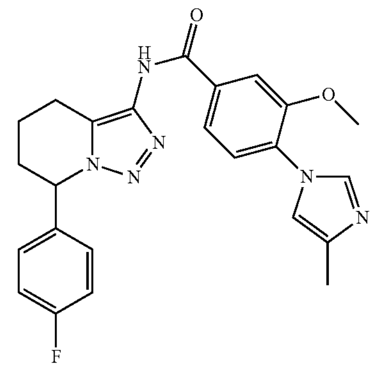 [SMILES: COc1cc(C(=O)Nc2nnn3c2CCCC3c2ccc(F)cc2)ccc1-n1cnc(C)c1] | d | a |
| 44 | 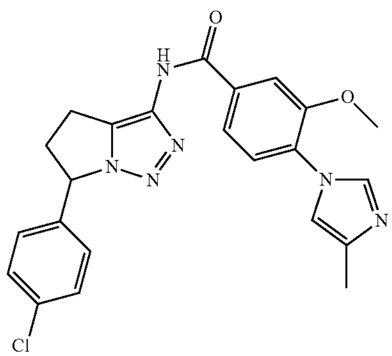 [SMILES: COc1cc(C(=O)Nc2nnn3c2CCC3c2ccc(Cl)cc2)ccc1-n1cnc(C)c1] | b | c |
| 45 | 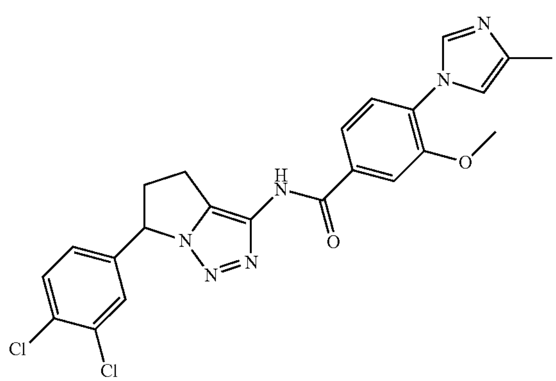 [SMILES: COc1cc(C(=O)Nc2nnn3c2CCC3c2ccc(Cl)c(Cl)c2)ccc1-n1cnc(C)c1] | b | c |
| 46 | 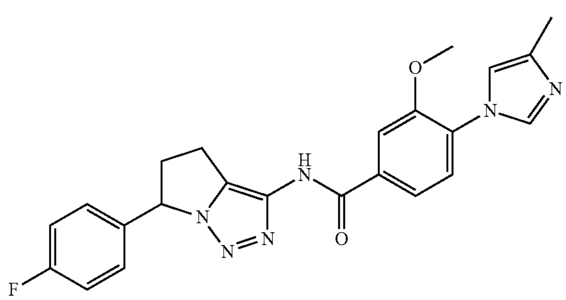 [SMILES: COc1cc(C(=O)Nc2nnn3c2CCC3c2ccc(F)cc2)ccc1-n1cnc(C)c1] | c | c |

-continued

| Example No | Structure | Ab42 IC50 Ranges | Abtot/Ab42 selectivity ranges |
|---|---|---|---|
| 47 | (structure) | d | d |
| 48 | (structure) | d | a |

| Ranges IC50 | a: IC50 ≤ 150 nM |
| | b: 150 nM < IC50 ≤ 500 nM |
| | c: 500 nM < IC50 ≤ 1000 nM |
| | d: IC50 < 1000 nM |
| Ranges Selectivity | a: selectivity ≥ 100 fold |
| | b: 100 fold > selectivity ≥ 50 fold |
| | c: 50 fold > selectivity ≥ 10 fold |
| | d: 10 fold > selectivity |

Example 49

In Vivo Assays

Measurement of Aβ Peptides in Brain

Rat brains were homogenized in 0.2% diethylamine (Thermo Fischer Scientific Inc., Waltham, Mass., USA) in 50 mM NaCl, pH 10 (10% v/w) and centrifuged for 35 min at 355,000×g. The supernatant was removed and neutralised with 0.5 M Tris HCl pH 6.8 (10% v/v). DEA brain extracts were assayed for Aβ40 using a sensitive immunoassay employing a biotinylated mid-region Aβ antibody, 4G8 (Covance, Princeton, N.J., USA) and a ruthenylated C-terminal Aβ40 antibody G2-10 (Millipore, Billerica, Mass., USA). Plates were analysed on a SECTOR® Imager 6000 (Meso Scale Discovery, Gaithersburg, Md., USA). Brain extracts were assayed for Aβ42 using a Human/Rat Beta Amyloid (42) ELISA Kit (Wako Chemicals, GmbH, Neuss, Germany).

The invention claimed is:

1. A compound of Formula (I)

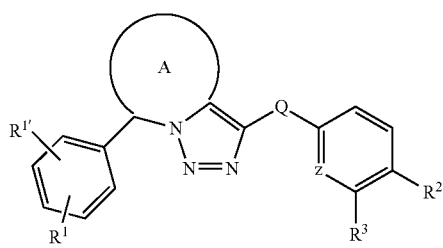

(I)

wherein

A denotes a 5- to 7-membered saturated carbocyclic ring wherein 1 —$CH_2$— group is optionally replaced by an oxygen atom;

$R^1$ and $R^{1'}$ are each independently selected from halogen, $CF_3$, and $C_1$-$C_6$-alkyl which is optionally substituted with one to 3 Hal, $C_1$-$C_6$-alkoxy, CN, $C_1$-$C_6$-alkyl sulfonyl and amine;

Q is selected from a —$NR^4$—, —$(CH_2)NR^4CO$—, —$NR^4CO$—, and —$CONR^4$—;

Z is CH or N, $R^2$ is a 5- to 6-membered unsaturated or aromatic heterocyclic ring containing 1 to 3 heteroatoms independently selected from O, N or S, and which is optionally substituted with 1 to 3 groups independently selected from $C_1$-$C_6$-alkyl, and $C_1$-$C_6$ alkoxy, $R^3$ is H, $C_1$-$C_6$-alkoxy, CN, or halogen; and each $R^4$ is independently H or $C_1$-$C_6$-alkyl;

and pharmaceutically acceptable solvates, tautomers, salts, hydrates and stereoisomers thereof, including mixtures thereof in all ratios.

2. The compound according to claim 1 wherein the group
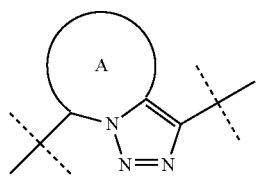
is selected from the following groups:
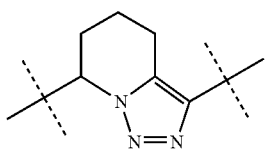
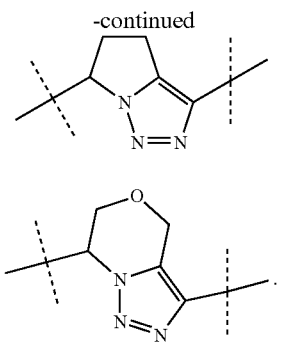
3. The compound according to claim 1, wherein $R^2$ is selected from methylpyridine, methylimidazole and methylpyrazole.
4. The compound according to claim 1 wherein the compound is selected from the following group:
| Example No | Structure |
|---|---|
| 1 | 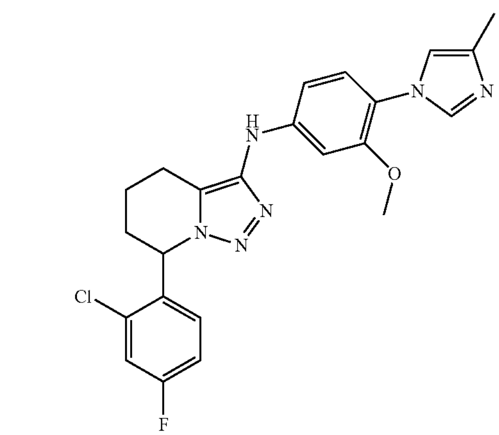 [SMILES: COc1cc(Nc2nnn3c2CCCC3c2ccc(F)cc2Cl)ccc1-n1cnc(C)c1] |
| 2 | 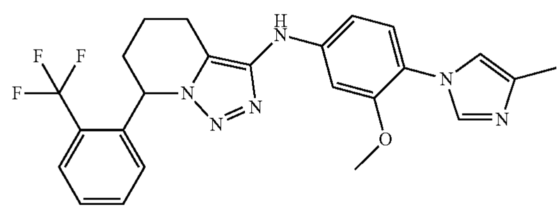 [SMILES: COc1cc(Nc2nnn3c2CCCC3c2ccccc2C(F)(F)F)ccc1-n1cnc(C)c1] |
| 3 | 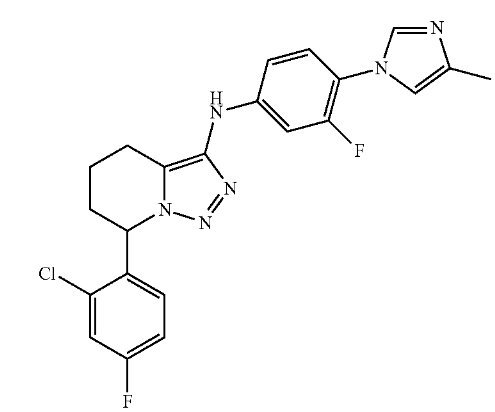 [SMILES: Cc1cn(-c2ccc(Nc3nnn4c3CCCC4c3ccc(F)cc3Cl)cc2F)cn1] |

-continued
| Example No | Structure |
|---|---|
| 4 | 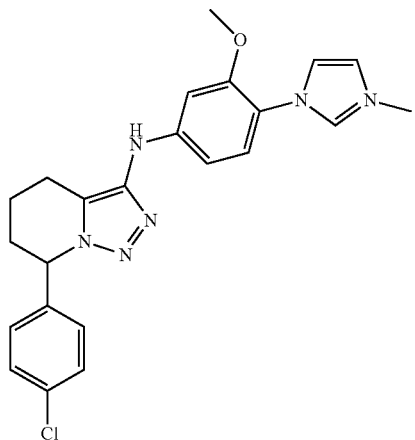 |
| 5 | 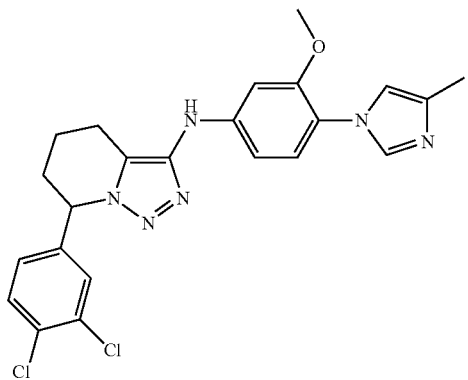 [SMILES: COc1cc(Nc2nnn3c2CCCC3c2ccc(Cl)c(Cl)c2)ccc1-n1cnc(C)c1] |
| 6 | 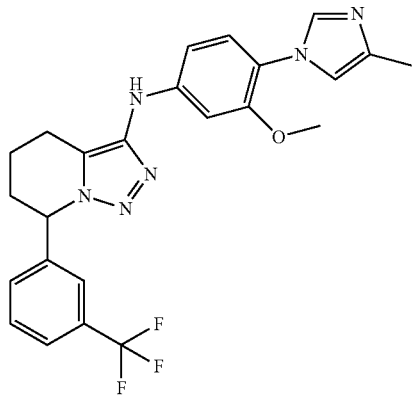 [SMILES: COc1cc(Nc2nnn3c2CCCC3c2cccc(C(F)(F)F)c2)ccc1-n1cnc(C)c1] |

-continued
| Example No | Structure |
|---|---|
| 7 | 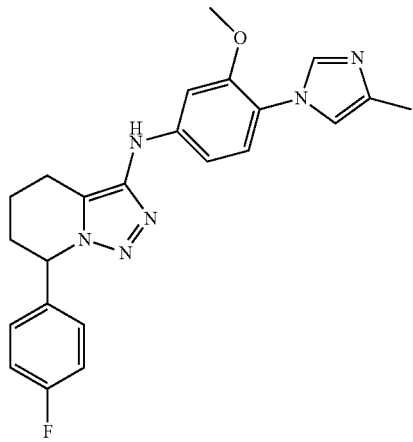 [SMILES: COc1cc(Nc2nnn3c2CCCC3c2ccc(F)cc2)ccc1-n1cnc(C)c1] |
| 8 | 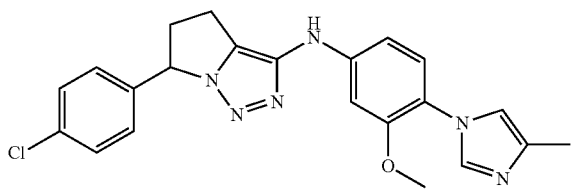 [SMILES: COc1cc(Nc2nnn3c2CCC3c2ccc(Cl)cc2)ccc1-n1cnc(C)c1] |
| 9 | 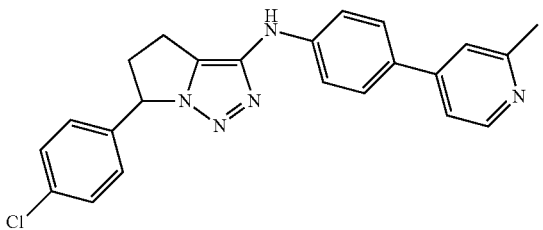 [SMILES: Cc1cc(-c2ccc(Nc3nnn4c3CCC4c3ccc(Cl)cc3)cc2)ccn1] |
| 10 | 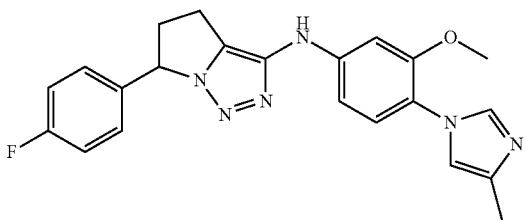 [SMILES: COc1cc(Nc2nnn3c2CCC3c2ccc(F)cc2)ccc1-n1cnc(C)c1] |
| 11 | 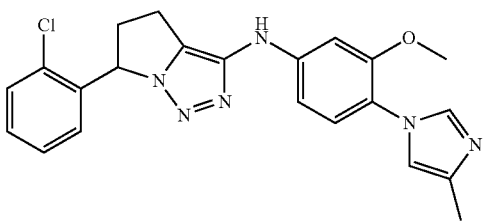 [SMILES: COc1cc(Nc2nnn3c2CCC3c2ccccc2Cl)ccc1-n1cnc(C)c1] |

-continued
| Example No | Structure |
|---|---|
| 12 | 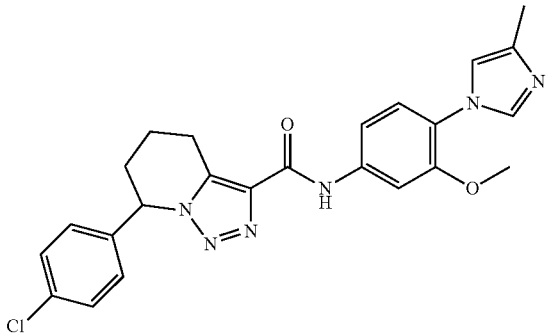 [SMILES: COc1cc(NC(=O)c2nnn3c2CCCC3c2ccc(Cl)cc2)ccc1-n1cnc(C)c1] |
| 13 | 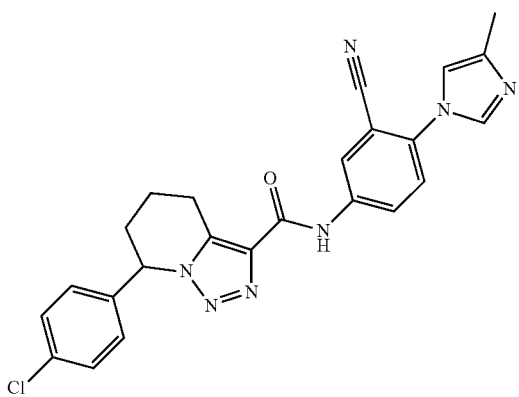 [SMILES: Cc1cn(-c2ccc(NC(=O)c3nnn4c3CCCC4c3ccc(Cl)cc3)cc2C#N)cn1] |
| 14 | 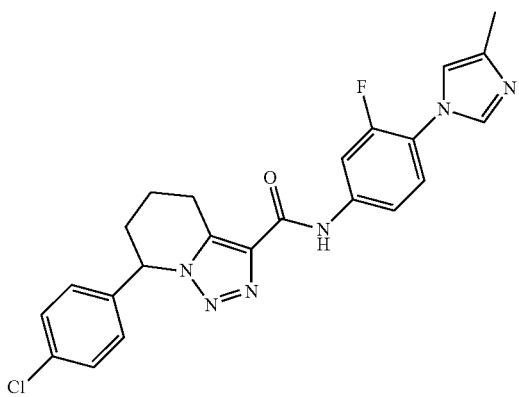 [SMILES: Cc1cn(-c2ccc(NC(=O)c3nnn4c3CCCC4c3ccc(Cl)cc3)cc2F)cn1] |
| 15 | 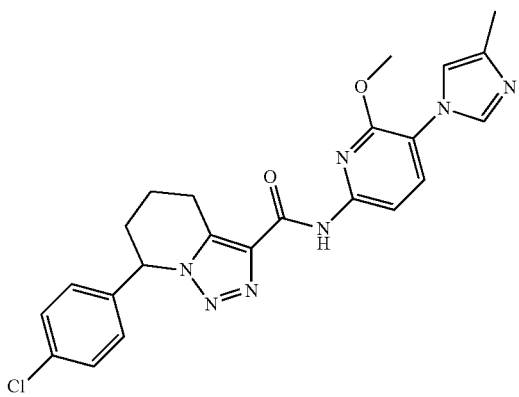 [SMILES: COc1nc(NC(=O)c2nnn3c2CCCC3c2ccc(Cl)cc2)ccc1-n1cnc(C)c1] |

-continued
| Example No | Structure |
|---|---|
| 16 | 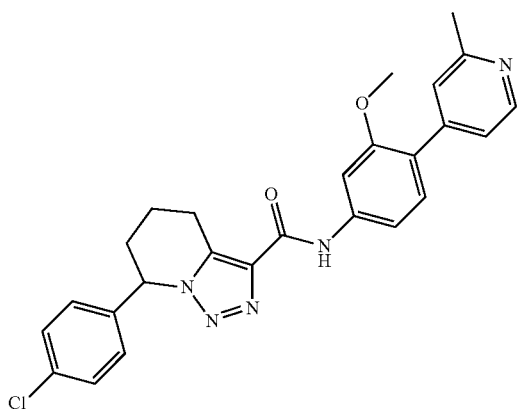 [SMILES: COc1cc(NC(=O)c2nnn3c2CCCC3c2ccc(Cl)cc2)ccc1-c1ccnc(C)c1] |
| 17 | 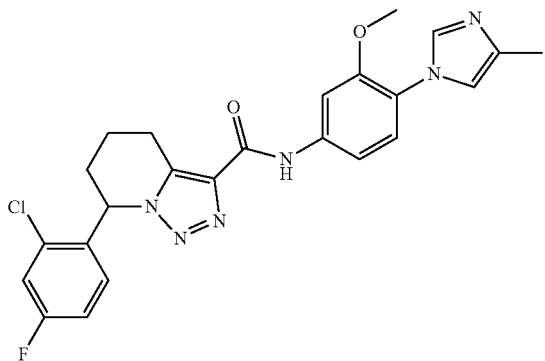 [SMILES: COc1cc(NC(=O)c2nnn3c2CCCC3c2ccc(F)cc2Cl)ccc1-n1cnc(C)c1] |
| 18 | 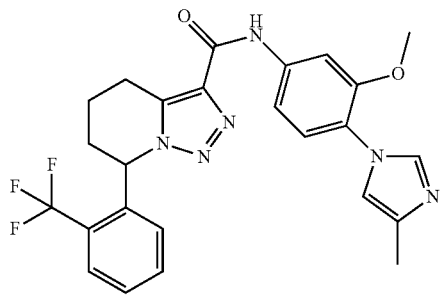 [SMILES: COc1cc(NC(=O)c2nnn3c2CCCC3c2ccccc2C(F)(F)F)ccc1-n1cnc(C)c1] |
| 19 | 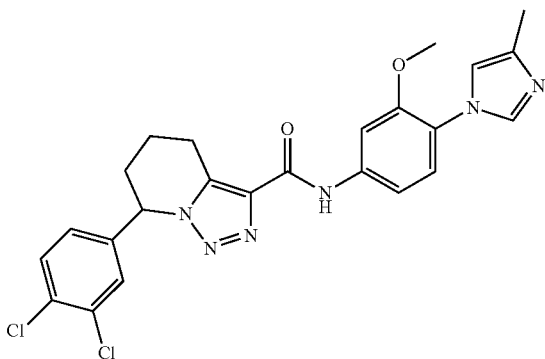 [SMILES: COc1cc(NC(=O)c2nnn3c2CCCC3c2ccc(Cl)c(Cl)c2)ccc1-n1cnc(C)c1] |

-continued
| Example No | Structure |
|---|---|
| 20 | 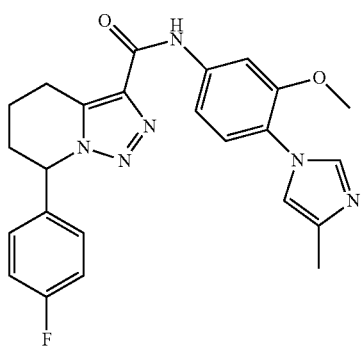 [SMILES: COc1cc(NC(=O)c2nnn3c2CCCC3c2ccc(F)cc2)ccc1-n1cnc(C)c1] |
| 21 | 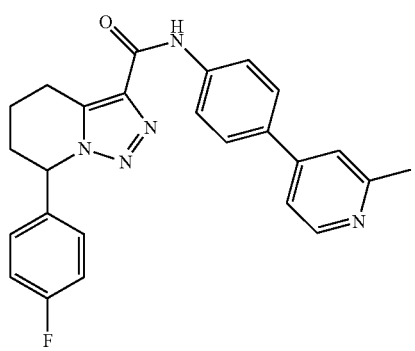 [SMILES: Cc1cc(-c2ccc(NC(=O)c3nnn4c3CCCC4c3ccc(F)cc3)cc2)ccn1] |
| 22 | 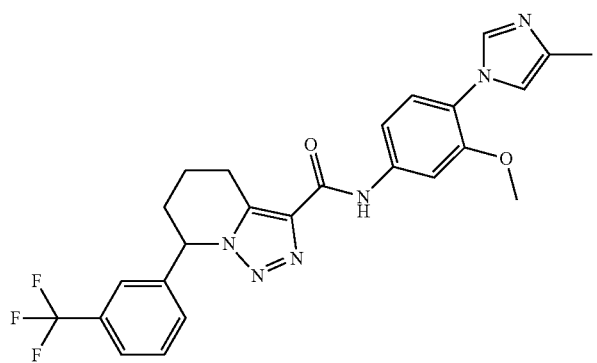 [SMILES: COc1cc(NC(=O)c2nnn3c2CCCC3c2cccc(C(F)(F)F)c2)ccc1-n1cnc(C)c1] |
| 23 | 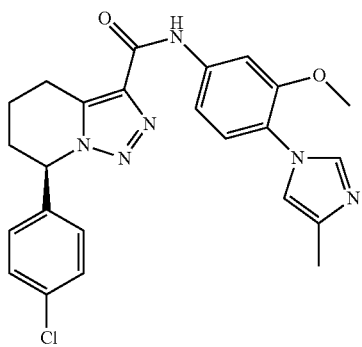 [SMILES: COc1cc(NC(=O)c2nnn3c2CCC[C@@H]3c2ccc(Cl)cc2)ccc1-n1cnc(C)c1] |

| Example No | Structure |
|---|---|
| 24 | 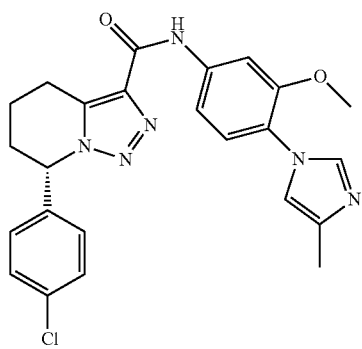 [SMILES: COc1cc(NC(=O)c2nnn3c2CCC[C@H]3c2ccc(Cl)cc2)ccc1-n1cnc(C)c1] |
| 25 | 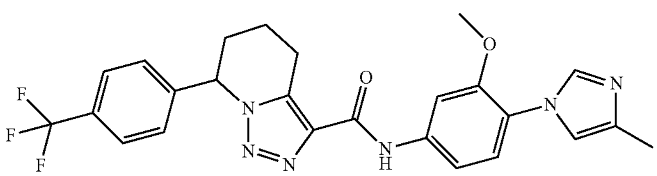 [SMILES: COc1cc(NC(=O)c2nnn3c2CCCC3c2ccc(C(F)(F)F)cc2)ccc1-n1cnc(C)c1] |
| 26 | 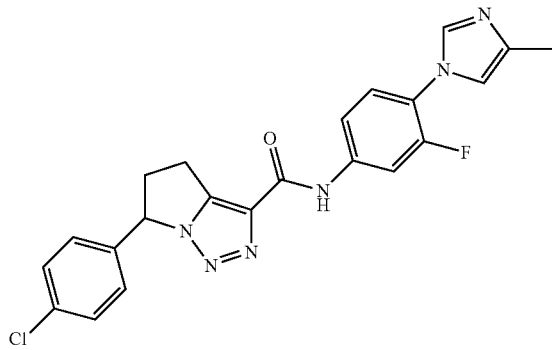 [SMILES: Cc1cn(-c2ccc(NC(=O)c3nnn4c3CCC4c3ccc(Cl)cc3)cc2F)cn1] |
| 27 | 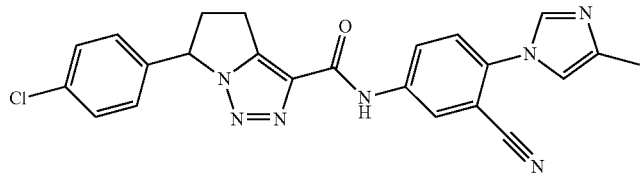 [SMILES: Cc1cn(-c2ccc(NC(=O)c3nnn4c3CCC4c3ccc(Cl)cc3)cc2C#N)cn1] |
| 28 | 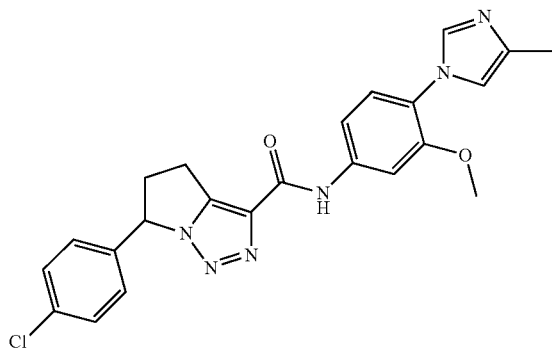 [SMILES: COc1cc(NC(=O)c2nnn3c2CCC3c2ccc(Cl)cc2)ccc1-n1cnc(C)c1] |

-continued
| Example No | Structure |
|---|---|
| 29 | 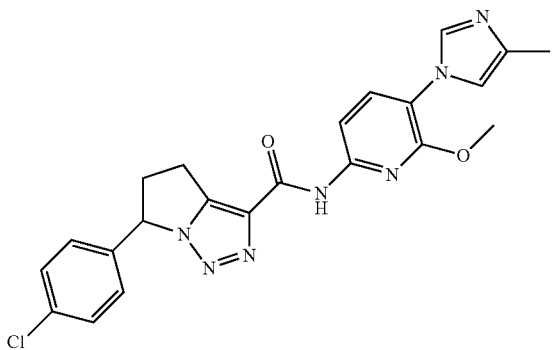 [SMILES: COc1nc(NC(=O)c2nnn3c2CCC3c2ccc(Cl)cc2)ccc1-n1cnc(C)c1] |
| 30 | 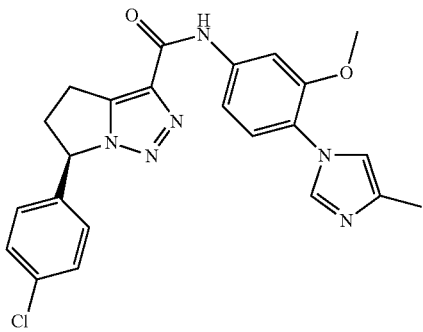 [SMILES: COc1cc(NC(=O)c2nnn3c2CC[C@@H]3c2ccc(Cl)cc2)ccc1-n1cnc(C)c1] |
| 31 | 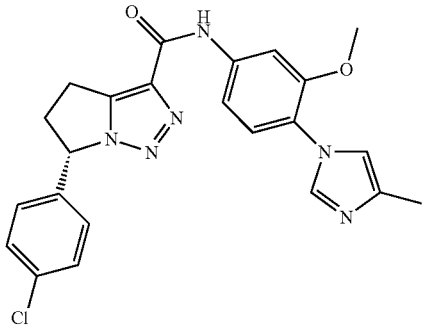 [SMILES: COc1cc(NC(=O)c2nnn3c2CC[C@H]3c2ccc(Cl)cc2)ccc1-n1cnc(C)c1] |
| 32 | 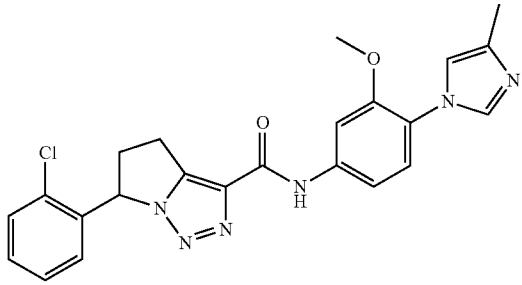 [SMILES: COc1cc(NC(=O)c2nnn3c2CCC3c2ccccc2Cl)ccc1-n1cnc(C)c1] |

-continued
| Example No | Structure |
|---|---|
| 33 | 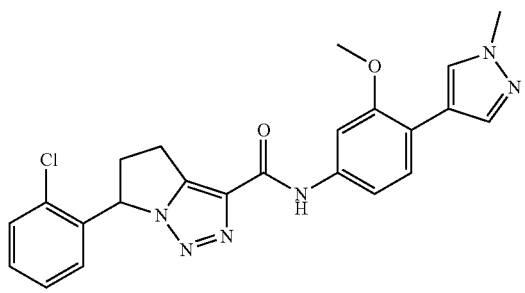 [SMILES: COc1cc(NC(=O)c2nnn3c2CCC3c2ccccc2Cl)ccc1-c1cnn(C)c1] |
| 34 | 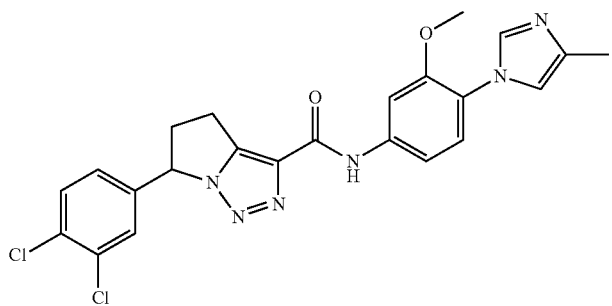 [SMILES: COc1cc(NC(=O)c2nnn3c2CCC3c2ccc(Cl)c(Cl)c2)ccc1-n1cnc(C)c1] |
| 35 | 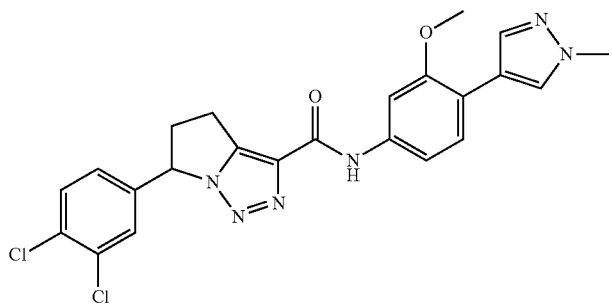 [SMILES: COc1cc(NC(=O)c2nnn3c2CCC3c2ccc(Cl)c(Cl)c2)ccc1-c1cnn(C)c1] |
| 36 | 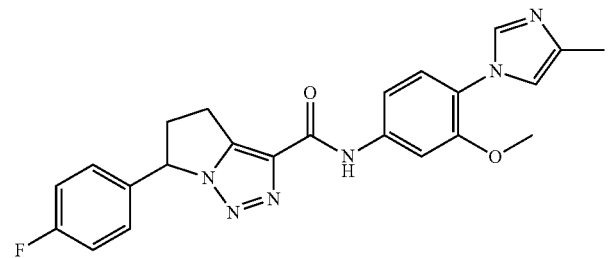 |
| 37 | 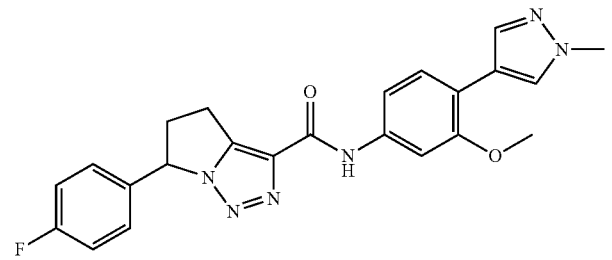 [SMILES: COc1cc(NC(=O)c2nnn3c2CCC3c2ccc(F)cc2)ccc1-c1cnn(C)c1] |

-continued
| Example No | Structure |
|---|---|
| 38 | 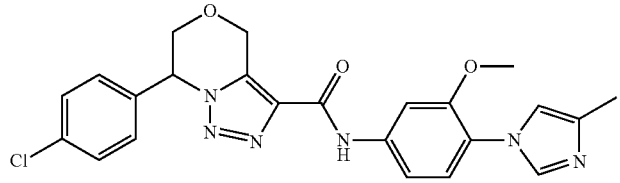 [SMILES: COc1cc(NC(=O)c2nnn3c2COCC3c2ccc(Cl)cc2)ccc1-n1cnc(C)c1] |
| 39 | 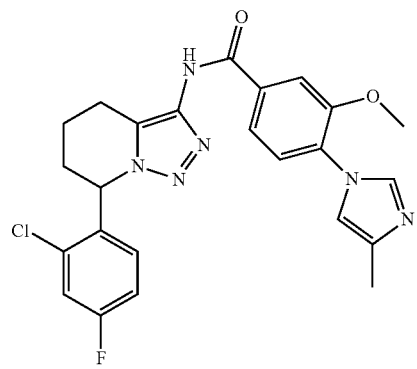 [SMILES: COc1cc(C(=O)Nc2nnn3c2CCCC3c2ccc(F)cc2Cl)ccc1-n1cnc(C)c1] |
| 40 | 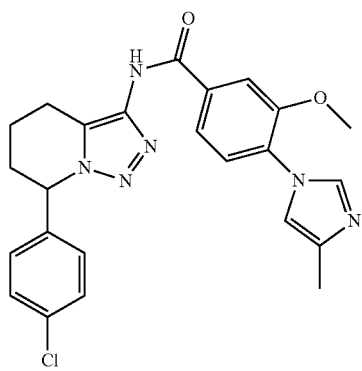 [SMILES: COc1cc(C(=O)Nc2nnn3c2CCCC3c2ccc(Cl)cc2)ccc1-n1cnc(C)c1] |
| 41 | 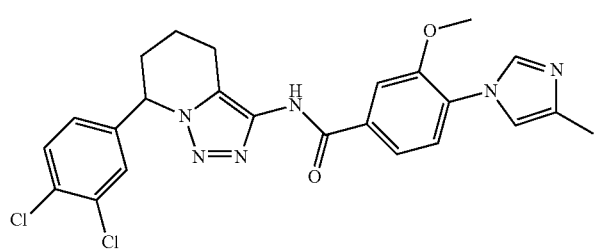 [SMILES: COc1cc(C(=O)Nc2nnn3c2CCCC3c2ccc(Cl)c(Cl)c2)ccc1-n1cnc(C)c1] |
| 42 | 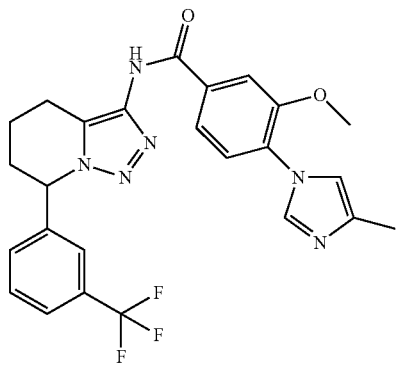 [SMILES: COc1cc(C(=O)Nc2nnn3c2CCCC3c2cccc(C(F)(F)F)c2)ccc1-n1cnc(C)c1] |

-continued
| Example No | Structure |
|---|---|
| 43 | 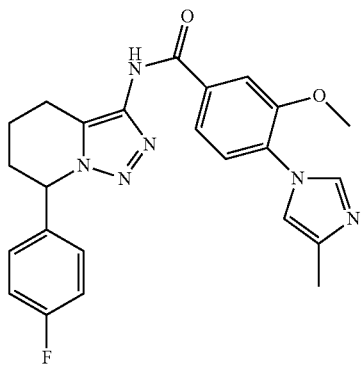 [SMILES: COc1cc(C(=O)Nc2nnn3c2CCCC3c2ccc(F)cc2)ccc1-n1cnc(C)c1] |
| 44 | 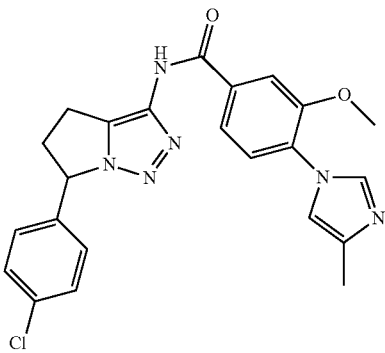 [SMILES: COc1cc(C(=O)Nc2nnn3c2CCC3c2ccc(Cl)cc2)ccc1-n1cnc(C)c1] |
| 45 | 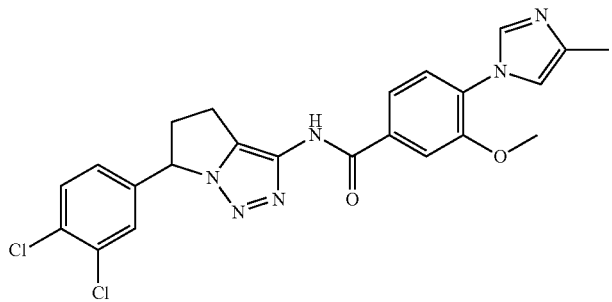 [SMILES: COc1cc(C(=O)Nc2nnn3c2CCC3c2ccc(Cl)c(Cl)c2)ccc1-n1cnc(C)c1] |
| 46 | 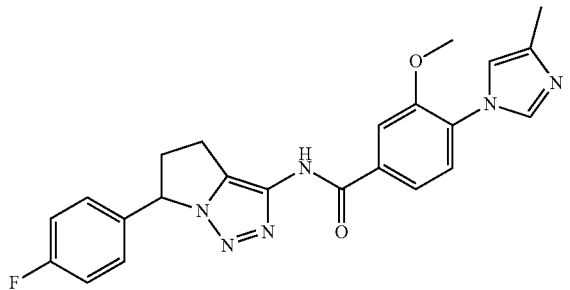 [SMILES: COc1cc(C(=O)Nc2nnn3c2CCC3c2ccc(F)cc2)ccc1-n1cnc(C)c1] |

| Example No | Structure |
|---|---|
| 47 | 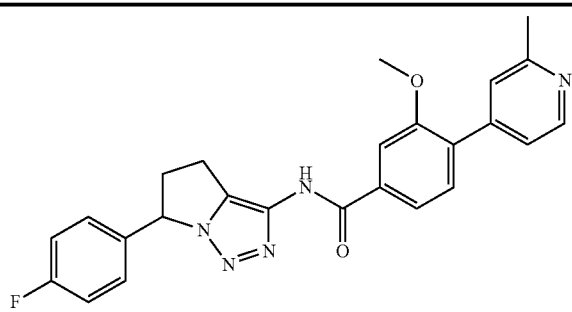 |
| 48 | 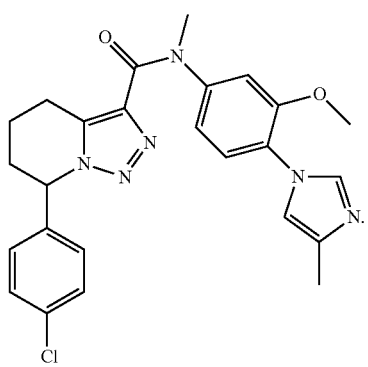 [SMILES: COc1cc(N(C)C(=O)c2nnn3c2CCCC3c2ccc(Cl)cc2)ccc1-n1cnc(C)c1] |

5. A kit consisting of separate packs of:

(a) an effective amount of a compound of claim 1, and/or pharmaceutically usable solvates, salts, hydrates and stereoisomers thereof, including mixtures thereof in all ratios, and (b) an effective amount of a further pharmaceutically active ingredient.

6. A pharmaceutical composition comprising at least one compound of claim 1.

7. The compound of claim 1, wherein Q is selected from —NH—, —(CH$_2$)NHCO—, —NHCO— or —CONH—, and —CONH—.

8. The compound of claim 1, wherein R$^1$ denotes Hal or CF$_3$.

9. The compound of claim 1, wherein R$^{1'}$ is H or Hal.

10. The compound of claim 1, of formula (I'):

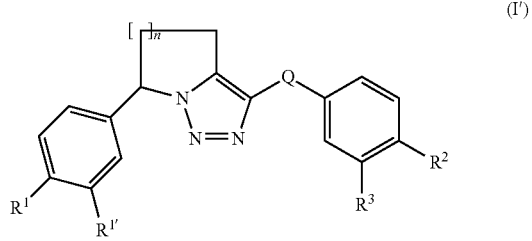

(I')

wherein n is 1 or 2.

11. The compound of claim 10, wherein R$^1$ denotes Hal or CF$_3$, and R$^{1'}$ is H or Hal.

12. The compound of claim 10, wherein Q denotes NH, —CONH—, CON(CH$_3$)— or —NHCO—.

* * * * *